(12) United States Patent
Ding et al.

(10) Patent No.: US 7,105,670 B2
(45) Date of Patent: Sep. 12, 2006

(54) INTERMEDIATES USEFUL IN THE PREPARATION OF DIAMINOTHIAZOLES

(75) Inventors: Qingjie Ding, Bridgewater, NJ (US); Paul Gillespie, Westfield, NJ (US); Kyungjin Kim, Livingston, NJ (US); Warren William McComas, Denville, NJ (US); Agostino Perrotta, Bloomfield, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 132 days.

(21) Appl. No.: 10/685,267

(22) Filed: Oct. 14, 2003

(65) Prior Publication Data

US 2004/0082595 A1    Apr. 29, 2004

Related U.S. Application Data

(62) Division of application No. 10/042,619, filed on Jan. 9, 2002, now Pat. No. 6,756,374.

(60) Provisional application No. 60/326,807, filed on Oct. 3, 2001, provisional application No. 60/263,315, filed on Jan. 22, 2001.

(51) Int. Cl.
*C07D 239/02* (2006.01)
*C07D 413/00* (2006.01)
*C07D 417/00* (2006.01)
*C07D 419/00* (2006.01)

(52) U.S. Cl. ............................... 544/304; 544/367
(58) Field of Classification Search ............... 544/304, 544/367
See application file for complete search history.

(56) References Cited

FOREIGN PATENT DOCUMENTS

| WO | WO97/16447 | 5/1997 |
|---|---|---|
| WO | WO98/33798 | 8/1998 |
| WO | WO99/09030 | 2/1999 |
| WO | WO00/12485 | 3/1999 |
| WO | WO99/24416 | 3/1999 |
| WO | WO99/21845 | 5/1999 |
| WO | WO-9921845 | * 5/1999 |
| WO | WO99/43675 | 9/1999 |
| WO | WO99/43676 | 9/1999 |
| WO | WO 00/26202 | 5/2000 |
| WO | WO00/39101 | 7/2000 |
| WO | WO00/75120 | 12/2000 |
| WO | WO 01/56567 | 8/2001 |
| WO | WO 01/60816 | 8/2001 |
| WO | WO 01/79198 | 12/2001 |
| WO | WO 02/12250 | 2/2002 |

OTHER PUBLICATIONS

Senderowicz, A.M., et al. J. Nat'l. Cancer Inst. 2000 vol. 92 pp. 376-387.
Chong, Wesley, K. M., Presentation at Gordon Conference on Medicinal Chemistry, Colby Sawyer College, New London, NH "Novel ATP Site Inhibitors of the Cyclin Dependent Kinases", Aug. 2, 1999 (Copy of Conference Handout Enclosed).
Fischer et al., Expert Opin. Investig. Drugs 12(6) pp. 955-970 (2003).
Grant et al., Drug Resistance vol. 6, pp. 15-26 (2003).

* cited by examiner

*Primary Examiner*—Alton Pryor
(74) *Attorney, Agent, or Firm*—George W. Johnston; Patricia S. Rocha-Tramaloni; Brian C. Remy

(57) ABSTRACT

Disclosed are novel diaminothiazoles that are selective inhibitors of Cdk4. These compounds and their pharmaceutically acceptable salts and esters are anti-proliferative agents useful in the treatment or control of solid tumors, in particular breast, colon, lung and prostate tumors. Also disclosed are pharmaceutical compositions containing these compounds as well as intermediates useful in the preparation of the compounds.

3 Claims, No Drawings

INTERMEDIATES USEFUL IN THE PREPARATION OF DIAMINOTHIAZOLES

PRIORITY TO RELATED APPLICATIONS

This application is a division of Ser. No. 10/042,619, filed Jan. 9, 2002, which is now U.S. Pat. No. 6,756,374. This application claims the benefit of U.S. Provisional Applications Ser. No. 60/263,315, filed Jan. 22, 2001, and 60/326,807, filed Oct. 3, 2001.

FIELD OF THE INVENTION

The present invention is directed to novel diaminothiazoles of formula

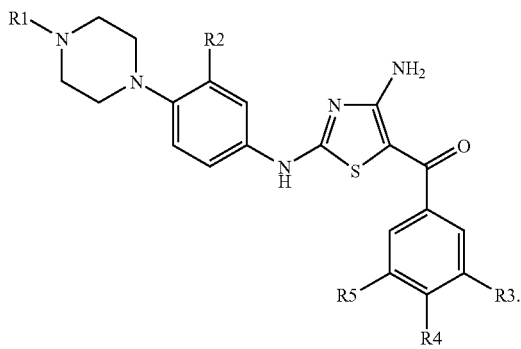

I

These compounds inhibit cyclin-dependent kinase 4 (Cdk4) and are selective against Cdk2 and Cdk1. These compounds and their pharmaceutically acceptable salts and esters have antiproliferative activity and are useful in the treatment or control of cancer, in particular solid tumors. This invention is also directed to pharmaceutical compositions containing such compounds and to methods of treating or controlling cancer, most particularly the treatment or control of breast, lung and colon and prostate tumors. Finally, this invention is also directed to novel intermediate compounds useful in the preparation of a compound of formula I.

BACKGROUND OF THE INVENTION

Uncontrolled cell proliferation is the hallmark of cancer. Cancerous tumor cells typically have some form of damage to the genes that directly or indirectly regulate the cell-division cycle.

The progression of cells through the various phases of the cell cycle is regulated by a series of multienzyme complexes consisting of a regulatory protein, a cyclin, and a kinase. These kinases are called cyclin-dependent kinases (Cdks). The Cdks are expressed throughout the cell cycle, while the levels of the cyclins vary depending on the stage of the cell cycle.

The transition from $G_1$ phase into S phase is regulated by the complex of Cdk4 with cyclin D. This complex phosphorylates the tumor supressor protein Retinoblastoma (pRb), releasing the transcription factor E2F and allowing the expression of genes required in S phase (Nevins, J. R. Science 1992, 258, 424–429). Blocking the activity of the Cdk4/cyclin D complex arrests the cell cycle in $G_1$ phase. For example the proteins of the INK4 family, including $p16^{INK4a}$, which block the kinase activity of the Cdk4/cyclin D complex, cause arrest in $G_1$ (Sherr, C. J. Science 1996, 274, 1672–1677).

Recent experiments show that the complex of Cdk4 with cyclin D3 also plays a role in cell cycle progression through $G_2$ phase. Inhibition of this complex, either by p16 or using a dominant negative Cdk4, results in arrest in $G_2$ phase in cells that do not express pRb (Gabrielli B. G. et al. J. Biol. Chem. 1999, 274, 13961–13969).

Numerous defects in the pRb pathway have been shown to be involved in various cancers. For example, overexpression of Cdk4 has been observed in cases of hereditary melanoma (Webster, K. R. Exp. Opin. Invest. Drugs 1998, 7, 865–887); cyclin D is overexpressed in many human cancers (Sherr, C. J. Science 1996, 274, 1672–1677); p16 is mutated or deleted in many tumors (Webster, K. R. Exp. Opin. Invest. Drugs 1998, 7, 865–887); and pRb function is lost through mutation or deletion in many human cancers (Weinberg, R. A. Cell 1995, 81, 323–330). Defects in this pathway have also been shown to have an effect on prognosis. For example, loss of p16 is correlated with poor prognosis in non-small-cell lung carcinoma (NSCLC) and malignant melanoma. (Tsihlias, J. et al. Annu. Rev. Med. 1999, 50, 401–423).

Because of the involvement of the Cdk4/cyclin D/pRb pathway in human cancer through its role in regulating progression of the cell cycle from $G_1$ to S phase, and the potential therapeutic benefit from modulating this pathway, there has been considerable interest in agents that inhibit or promote elements of this pathway. For example, effects on cancer cells have been shown using antibodies, antisense oligonucleotides and overexpression or addition of proteins involved in the pathway. See, e.g., Lukas, J. et al. Nature 1995, 79, 573–582, Nevins, J. R. Science. 1992, 258, 424–429; Lim, I. K. et al. Molecular Carcinogenesis 1998, 23, 25–35; Tam, S. W. et al. Oncogene 1994, 9, 2663–2674; Driscoll, B. et al. Am. J. Physiol. 1997, 273 (Lung Cell. Mol. Physiol.), L941–L949; and Sang, J. et al. Chin. Sci. Bull. 1999, 44, 541–544). There is thus an extensive body of literature validating the use of compounds inhibiting targets in the Cdk4 pathway as anti-proliferative therapeutic agents.

It is thus desirable to identify chemical inhibitors of Cdk4 kinase activity. It is particularly desirable to identify small molecule compounds that may be readily synthesized and are effective in inhibiting Cdk4 or Cdk4/cyclin complexes, for treating one or more types of tumors.

There are several examples of small molecule inhibitors of the cyclin-dependent kinases; including Cdk4 (Rosania, G. R. et al. Exp. Opin. Ther. Patents 2000, 10, 215–230). Several of these compounds inhibit multiple targets.

For example, Flavopiridol (Aventis)

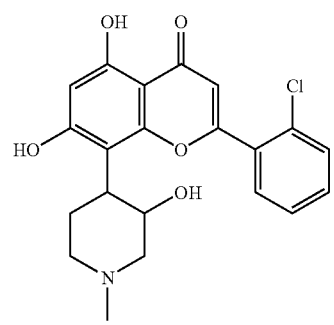

is in Phase II clinical trials for lymphoma and multiple myeloma and also for the treatment of solid tumors. It inhibits Cdk1, Cdk2 and Cdk4 and it blocks cells in both G1 and G2 phases. It is also a weaker inhibitor of PKC and EGFR (Senderowicz, A. M. et al. *J. Natl. Cancer Inst.* 2000, 92, 376–387).

WO9716447 (Mitotix) discloses the following compounds related to, flavopiridol

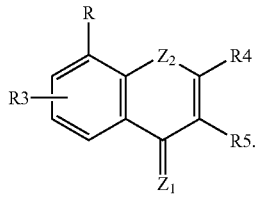

Some of these compounds are stated to inhibit Cdk4.

WO9943675 and WO9943676 (Hoechst) disclose the following purine derivatives

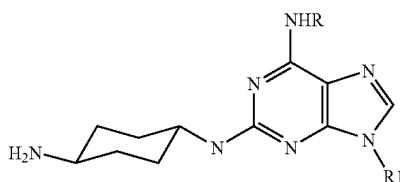

which are stated to inhibit Cdk2 and Cdk4.

WO9833798 (Warner-Lambert) discloses the following pyridopyrimidines

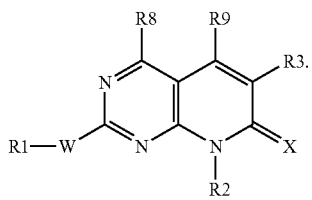

These compounds are stated to inhibit the cyclin dependent kinases Cdk1, Cdk2, and Cdk4. Some of these compounds also inhibit the receptor tyrosine kinases PDGFR and EGFR, and the cellular Src protein kinase, c-Src.

WO9909030 (Warner-Lambert) discloses naphthyridinones

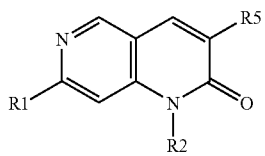

that inhibit PDGFR, FGFR, c-Src, and the cyclin dependent kinases Cdk1, Cdk2, and Cdk4.

WO0039101 (AstraZeneca) discloses diaminopyrimidines

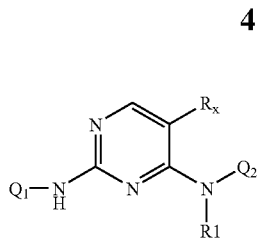

that inhibit Cdk4 and FAK3.

WO0012485 (Zeneca) discloses diaminopyrimidines

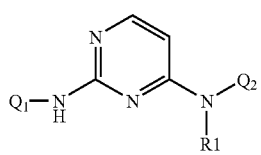

that inhibit Cdk4 and FAK3.

WO9924416 (Bristol-Myers Squibb) discloses aminothiazole inhibitors of formula

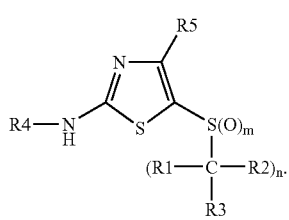

The compounds inhibit Cdk1, Cdk2 and Cdk4.

WO9921845 (Agouron) discloses diaminothiazole inhibitors of Cdk1, Cdk2 and Cdk4, having the following structure

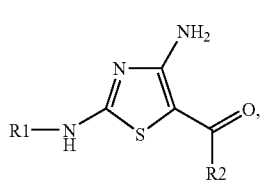

where R1 and R2 are ring systems. This, patent application indicates that in cases where the $R^2$ ring system does not bear an ortho substituent, the compounds lack potency and selectivity as inhibitors of Cdk4.

Finally, WO0075120 (Agouron) discloses diaminothiazole inhibitors of protein kinases including VEGF-R, FGF-R, CDK complexes, TEK, CHK1, LCK, and FAK, having the following structure

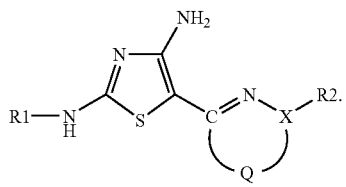

It is desirable to provide small molecule inhibitors of Cdk4 that are selective against other Cdks. That is, the small molecule is significantly more inhibitory (at least 10 times, preferably 100 times) of Cdk4 than Cdk1 and Cdk2. This parameter is desirable because of the potential concomitant toxicity and other undesirable complications that may follow from inhibiting multiple targets. Thus, for purposes of this invention, the inhibition of Cdk2 and Cdk1 are monitored to determine the selectivity of the inhibition of Cdk4. A compound that exhibits selectivity against Cdk2 and Cdk1 is expected to have a better safety profile than a compound that is not selective between Cdk4, Cdk2 and Cdk1.

There continues to be a need for easily synthesized, small molecule compounds that are specific inhibitors of Cdk4 for the treatment or control of one or more types of solid tumors. It is an object of this invention to provide such compounds, compositions containing such compounds, and methods of using such compounds in the treatment or control of breast, colon, lung and prostate tumors.

SUMMARY OF THE INVENTION

The present invention is directed to novel diaminothiazoles capable of selectively inhibiting the activity of Cdk4. These compounds are useful in the treatment or control of cancer, in particular the treatment or control of solid tumors. In particular this invention is directed to a compound of formula

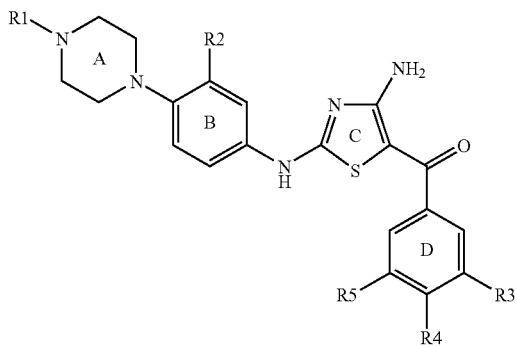

I or the pharmaceutically acceptable salts or esters thereof, wherein $R^1$ is selected from the group consisting of
H,
lower alkyl that optionally may be substituted with a group selected from $OR^6$, cycloalkyl, and $NR^7R^8$,
cycloalkyl,
$COR^9$, and
$SO_2R^{10}$;

$R^2$ is selected from the group consisting of H,
F,
Cl, and
$CH_3$;

$R^3$, $R^4$ and $R^5$ are each independently selected from the group consisting of H;
lower alkyl, which optionally may be substituted with a group selected from $OR^6$ and $NR^7R^8$,
$OR^{11}$,
$NR^{12}R^{13}$,
halogen,
$NO_2$,
$CONR^6R^9$,
$NHSO_2R^{14}$,
CN,
S-lower alkyl,
$OCF_3$, and
$OCHF_2$,
or alternatively, $R^3$ and $R^4$ taken together with the two carbons and the bond between them from the benzene ring (D) to which $R^3$ and $R^4$ are attached can form a ring system having up to two additional rings, each of said rings having 5–7 atoms, and the ring attached to the benzene ring (D) optionally including one or more hetero atoms and being optionally substituted by lower alkyl,
provided that $R^3$ and $R^4$ are not simultaneously —$OCH_3$, and provided further that $R^4$ is not —Cl when $R^3$ is —$NO_2$;

$R^6$ and $R^9$ are independently selected from the group consisting of
H, and
lower alkyl that optionally may be substituted by OH and halogen;

$R^7$ and $R^8$ are independently selected from the group consisting of
H, and
lower alkyl that optionally may be substituted by $OR^6$,
or, alternatively, $R^7$ is H and $R^8$ is OH,
or, alternatively, $NR^7R^8$ can optionally form a ring having 5–6 atoms, said ring optionally including one or more additional hetero atoms and being optionally substituted by the group consisting of one or more of $OR^6$ and lower alkyl which itself may be optionally substituted by OH;

$R^{10}$ is selected from the group consisting of
lower alkyl which optionally may be substituted by one or more chlorine or fluorine, and
$NH_2$;

$R^{11}$ is selected from the group consisting of H, and
lower alkyl that optionally may be substituted by $OR^6$, COOH, halogen and $NR^{15}R^{16}$;

$R^{12}$ and $R^{13}$ are independently selected from the group consisting of H;
lower alkyl that optionally may be substituted with a group selected from $OR^6$, COOH and $NR^{15}R^{16}$,
$COR^{17}$, and
$SO_2R^{18}$,
provided that only one of $R^{12}$ and $R^{13}$ is $COR^{17}$ or $SO_2R^{18}$,
or alternatively $NR^{12}R^{13}$ can optionally form a ring having 5–6 atoms, said ring optionally including one or more additional hetero atoms and being optionally substituted by the group consisting of one or more of $OR^6$ and lower alkyl which itself may be optionally substituted by OH;

$R^{14}$ is lower alkyl;

$R^{15}$ and $R^{16}$ are independently selected from the group consisting of H, and
lower alkyl that optionally may be substituted by OH,
or alternatively $NR^{15}R^{16}$ can optionally form a ring having 5–6 atoms, said ring optionally including one or more additional hetero atoms and being optionally substituted by the group consisting of one or more of $OR^6$ and lower alkyl which itself may be optionally substituted by OH;

$R^{17}$ is selected from the group consisting of H, and
lower alkyl which optionally may be substituted by OH, COOH and $NR^{15}R^{16}$; and $R^{18}$ is lower alkyl:

The present invention is also directed to pharmaceutical compositions comprising a therapeutically effective amount of one or more compounds of formula I and a pharmaceutically acceptable carrier or excipient.

The present invention is further directed to a method for treating solid tumor, in particular breast or colon tumors, by administering to a human patient in need of such therapy an effective amount of a compound of formula I, its salt and/or ester.

The present invention is also directed to novel intermediate compounds useful in the preparation of compounds of formula I.

DETAILED DESCRIPTION OF THE INVENTION

Definitions

As used herein, the following terms shall have the following definitions.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine.

"Hetero atom" means an atom selected from N, O and S.

"$IC_{50}$" refers to the concentration of a particular compound according to the invention required to inhibit 50% of a specific measured activity. $IC_{50}$ can be measured, inter alia, as is described in Example 125, infra.

"Lower alkyl" denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids ($R^{24}C(=O)OH$) are lower alkyl esters which may be substituted with $NR^{25}R^{26}$ where $R^{25}$ and $R^{26}$ are lower alkyl, or where $NR^{25}R^{26}$ taken together form a monocyclic aliphatic heterocycle, such as pyrrolidine, piperidine, morpholine, N-methylpiperazine, etc.; acyloxyalkyl esters of the formula $R^{24}C(=O)OCHR^{27}OC(=O)R^{28}$ where $R^{27}$ is hydrogen or methyl, and $R^{28}$ is lower alkyl or cycloalkyl; carbonate esters of the formula $R^{24}C(=O)OCHR^{27}OC(=O)OR^{29}$ where $R^{27}$ is hydrogen or methyl, and $R^{29}$ is lower alkyl or cycloalkyl; or aminocarbonylmethyl esters of the formula $R^{24}C(=O)OCH_2C(=O)NR^{25}R^{26}$ where $R^{25}$ and $R^{26}$ are hydrogen or lower alkyl, or where $NR^{25}R^{26}$ taken together form a monocyclic aliphatic heterocycle, such as pyrrolidine, piperidine, morpholine, N-methylpiperazine, etc.

Examples of lower alkyl esters are the methyl, ethyl, and n-propyl esters, and the like. Examples of lower alkyl esters substituted with $NR^{19}R^{20}$ are the diethylaminoethyl, 2-(4-morpholinyl)ethyl, 2-(4-methylpiperazin-1-yl)ethyl esters, and the like. Examples of acyloxyalkyl esters are the pivaloxymethyl, 1-acetoxyethyl, and acetoxymethyl esters. Examples of carbonate esters are the 1-(ethoxycarbonyloxy)ethyl and 1-(cyclohexyloxycarbonyloxy)ethyl esters.

Examples of aminocarbonylmethyl esters are the N,N-dimethylcarbamoylmethyl and carbamoylmethyl esters.

Further information concerning examples of and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid; fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

In one embodiment, the invention is directed to a compound of formula

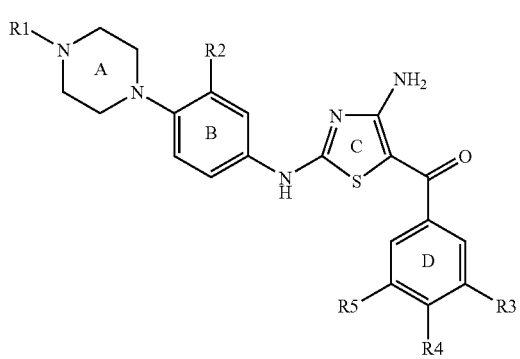

I or the pharmaceutically acceptable salts or esters thereof, wherein $R^1$ is selected from the group consisting of H, lower alkyl that optionally may be substituted from the group selected from $OR^6$, cycloalkyl, and $NR^7R^8$,
cycloalkyl,
$COR^9$, and
$SO_2R^{10}$;
$R^2$ is selected from the group consisting of H,
F,
Cl, and
$CH_3$;
$R^3$, $R^4$ and $R^5$ are each independently selected from the group consisting of H,
lower alkyl, which optionally may be substituted with a group selected from $OR^6$ and $NR^7R^8$,
$OR^{11}$,
$NR^{12}R^{13}$,
halogen,
$NO_2$,
$CONR^6R^9$,
$NHSO_2R^{14}$,
CN,
S-lower alkyl,
$OCF_3$, and
$OCHF_2$,
or alternatively, $R^3$ and $R^4$ taken together with the two carbons and the bond between them from the benzene ring (D) to which $R^3$ and $R^4$ are attached can form a ring system having up to two additional rings, each of said rings having 5–7 atoms, and the ring attached to the benzene ring (D) optionally including one or more hetero atoms and being optionally substituted by lower alkyl,
provided that $R^3$ and $R^4$ are not simultaneously —$OCH_3$, and provided further that $R^4$ is not —Cl when $R^3$ is —$NO_2$;
$R^6$ and $R^9$ are independently selected from the group consisting of
H, and
lower alkyl that optionally may be substituted by OH and halogen;
$R^7$ and $R^8$ are independently selected from the group consisting of
H, and
lower alkyl that optionally may be substituted by $OR^6$,
or, alternatively, $R^7$ is H and $R^8$ is OH,
or, alternatively, $NR^7R^8$ can optionally form a ring having 5–6 atoms, said ring optionally including one or more additional hetero atoms and being optionally substituted by the group consisting of one or more of $OR^6$ and lower alkyl which itself may be optionally substituted by OH;
$R^{10}$ is selected from the group consisting of
lower alkyl which optionally may be substituted by one or more chlorine or fluorine, and
$NH_2$;
$R^{11}$ is selected from the group consisting of H, and
lower alkyl that optionally may be substituted by a group selected from $OR^6$, COOH, halogen and $NR^{15}R^{16}$;
$R^{12}$ and $R^{13}$ are independently selected from the group consisting of
H,
lower alkyl that optionally may be substituted with a group selected from $OR^6$, COOH and $NR^{15}R^{16}$,
$COR^{17}$, and
$SO_2R^{18}$,
provided that only one of $R^{12}$ and $R^{13}$ is $COR^{17}$ or $SO_2R^{18}$,
or alternatively $NR^{12}R^{13}$ can optionally form a ring having 5–6 atoms, said ring optionally including one or more additional hetero atoms and being optionally substituted by the group consisting of one or more of $OR^6$ and lower alkyl which itself may be optionally substituted by OH;
$R^{14}$ is lower alkyl;
$R^{15}$ and $R^{16}$ are independently selected from the group consisting of
H, and
lower alkyl that optionally may be substituted by OH,
or alternatively $NR^{15}R^{16}$ can optionally form a ring having 5–6 atoms, said ring optionally including one or more additional hetero atoms and being optionally substituted by the group consisting of one or more of $OR^6$ and lower alkyl which itself may be optionally substituted by OH;
$R^{17}$ is selected from the group consisting of H, and
lower alkyl which optionally may be substituted by OH, COOH and $NR^{15}R^{16}$; and
$R^{18}$ is lower alkyl.
In a preferred embodiment of the compounds of formula I, $R^1$ is selected from the group consisting of H, $CH_2CH_2OH$, $CH_2CH_2CH_2OH$, $CH_3CO$—, $CH(CH_3)_2$, $CH_2CH(CH_3)_2$, cyclopropylmethyl and $CH_3$. More preferably, $R^1$ is H, methyl, $CH_2CH_2CH_2OH$, or $CH(CH_3)_2$.
In another preferred embodiment of the compounds of formula I, $R^2$ is selected from the group consisting of H and fluorine, most preferably H.
In another preferred embodiment of the compounds of formula I, $R^3$ is selected from the group $OR^{11}$, lower alkyl, $NH_2$, Cl, F, H, $OCHF_2$, and $NO_2$. More preferably, $R^3$ is $OCH_3$, F, lower alkyl or $OCHF_2$. Most preferably, $R^3$ is F, $OCH_3$ or $CH_2CH_3$.
In another preferred embodiment of the compounds of formula I, $R^4$ is selected from the group consisting of acetamido, chloro, diethylamino, hydrogen, hydroxy, hydroxyethylamino, [1-(hydroxymethyl)-3-methylbutyl]amino, 1-(3-hydroxymethyl)piperidinyl, 4-hydroxy-1-piperidinyl, methoxy, 2-methoxy-ethylamino, 2-methyl-1-pyrrolidinyl, morpholino, piperidinyl, pyrrolidinyl. More preferably, $R^4$ is selected from the group consisting of H and $CH_3O$—.
When $R^3$ and $R^4$ taken together with the benzene ring to which they are attached form a ring system, preferred ring systems are 2-dibenzofuranyl, 1,3-benzodioxol-5-yl, 2,3-dihydro-1,4-benzodioxin-6-yl, or 3,4-dihydro-2H-1,5-benzodioxepin-7-yl, more preferably 2,3-dihydro-1,4-benzodioxin-6-yl.
In another preferred embodiment of the compounds of formula I, $R^5$ is selected from the group consisting of H, $OR^{11}$ and F, most preferably H.
In another preferred embodiment of the compounds of formula I,
$R^1$ is selected from the group consisting of H, and
lower alkyl that optionally may be substituted by $OR^6$;
$R^2$ is selected from the group consisting of H and F;
$R^3$ is selected from the group consisting of H,
lower alkyl
halogen,
$NR^{12}R^{13}$,
$NO_2$,
$OCHF_2$, and
$OR^{11}$;
$R^4$ is selected from the group consisting of H,
lower alkyl that optionally may be may be substituted by $OR^6$,
halogen, and
$NR^{12}R^{13}$,
or alternatively, $R^3$ and $R^4$ taken together with the two carbons and the bond between them from the benzene ring (D) to which $R^3$ and $R^4$ are attached can form a ring system having up to two additional rings, each of said rings having 5–7 atoms, and the ring attached to the benzene ring (D) optionally including one or more hetero atoms and being optionally substituted by lower alkyl, provided that $R^4$ is not —Cl when $R^3$ is —$NO_2$;

$R^6$ is selected from the group consisting of H, and methyl;

$R^{11}$ is selected from the group consisting of H, and, lower alkyl that optionally may be substituted by a group selected from $OR^6$, COOH, halogen and $NR^{15}R^{16}$;

$R^{12}$ and $R^{13}$ are independently selected from the group consisting of

H, lower alkyl that optionally may be substituted with a group selected from $OR^6$, COOH and $NR^{15}R^{16}$, or alternatively $NR^{12}R^{13}$ can optionally form a ring having 5–6 atoms, said ring optionally including one or more additional hetero atoms and being optionally substituted by the group consisting of one or more of $OR^6$ and lower alkyl which itself may be optionally substituted by OH; and $R^{15}$ and $R^{16}$ are independently selected from the group consisting of H, and lower alkyl that optionally may be substituted by OH, or alternatively $NR^{15}R^{16}$ can optionally form a ring having 5–6 atoms, said ring optionally including one or more additional hetero atoms and being optionally substituted by the group consisting of one or more of $OR^6$ and lower alkyl which itself may be optionally substituted by OH.

In a most preferred embodiment of the compounds of formula I, $R^1$ is selected from the group consisting of H, $CH_2CH_2OH$, $CH_2CH_2CH_2OH$, $CH_3CO$—, $CH(CH_3)_2$, $CH_2CH(CH_3)_2$, cyclopropylmethyl, and $CH_3$;

$R^2$ s selected from the group consisting of H and F;

$R^3$ is selected from the group consisting of $OR^{11}$, lower alkyl, $NH_2$,

Cl,

F,

H, $OCHF_2$, and $NO_2$;

$R^4$ is selected from the group consisting of H, and diethylamino;

$R^5$ is H; and $R^{11}$ is unsubstituted lower alkyl.

In another most preferred embodiment of the compounds of formula I, $R^1$ is selected from the group consisting of H, $CH_2CH_2CH_2OH$, $CH(CH_3)_2$, $CH_3$, and cyclopropylmethyl;

$R^2$, $R^4$ and $R^5$ are H; and $R^3$ is selected from the group consisting of $OCH_3$, F, and $CH_2CH_3$.

The following are examples of preferred compounds of formula I:

[4-Amino-2-[[4-(4-methyl-1-piperazinyl)phenyl]amino]-5-thiazolyl](2,3-dihydro-1,4-benzodioxin-6-yl)methanone (Example 24),

[4-Amino-2-[[4-(4-methyl-1-piperazinyl)phenyl]amino]-5-thiazolyl](1,3-benzodioxol-5-yl)methanone (Example 25),

[4-Amino-2-[[4-(4-methyl-1-piperazinyl)phenyl]amino]-5-thiazolyl][4-(1-pyrrolidinyl)phenyl]methanone (Example 26),

[4-Amino-2-[[4-(4-methyl-1-piperazinyl)phenyl]amino]-5-thiazolyl][4-(1-piperidinyl)phenyl]methanone (Example 27),

[4-Amino-2-[[4-(4-methyl-1-piperazinyl)phenyl]amino]-5-thiazolyl][4-(4-morpholinyl)phenyl]methanone, acetate salt (Example 28),

[4-Amino-2-[[4-(4-methyl-1-piperazinyl)phenyl]amino]-5-thiazolyl](3,4-dihydro-2H-1,5-benzodioxepin-7-yl) methanone (Example 29),

[4-Amino-2-[[4-(4-methyl-1-piperazinyl)phenyl]amino]-5-thiazolyl]-(4-hydroxyphenyl)methanone (Example 30),

[4-Amino-2-[[4-(4-methyl-1-piperazinyl)phenyl]amino]-5-thiazolyl](3-nitrophenyl)methanone (Example 31),

[4-Amino-2-[[4-(4-methyl-1-piperazinyl)phenyl]amino]-5-thiazolyl](4-methoxyphenyl)methanone (Example 32),

[4-Amino-2-[[4-(4-methyl-1-piperazinyl)phenyl]amino]-5-thiazolyl][4-(diethylamino)phenyl]methanone (Example 33),

[4-Amino-2-[[4-(4-methyl-1-piperazinyl)phenyl]amino]-5-thiazolyl](2-dibenzofuranyl)methanone (Example 34),

[4-Amino-2-[[4-(4-methyl-1-piperazinyl)phenyl]amino]-5-thiazolyl](3-fluoro-4-methoxyphenyl)methanone (Example 35),

[4-Amino-2-[[4-(4-methyl-1-piperazinyl)phenyl]amino]-5-thiazolyl](3-methoxyphenyl)methanone (Example 36),

[4-Amino-2-[[4-(4-methyl-1-piperazinyl)phenyl]amino]-5-thiazolyl](3,4-dichlorophenyl)methanone (Example 37),

[4-Amino-2-[[3-fluoro-4-(4-methyl-1-piperazinyl)phenyl]amino]-5-thiazolyl](1,3-benzodioxol-5-yl)methanone (Example 38),

[4-Amino-2-[[3-fluoro-4-(4-methyl-1-piperazinyl)phenyl]amino]-5-thiazolyl](3,5-dimethoxyphenyl)methanone (Example, 39),

[4-Amino-2-[[3-fluoro-4-(4-methyl-1-piperazinyl)phenyl]amino]-5-thiazolyl](3-methoxyphenyl)methanone (Example 40),

[4-Amino-2-[[4-[4-(1-methylethyl)-1-piperazinyl]phenyl]amino]-5-thiazolyl](2,3-dihydro-1,4-benzodioxin-6-yl) methanone (Example 41),

[4-Amino-2-[[4-[4-(1-methylethyl)-1-piperazinyl]phenyl]amino]-5-thiazolyl](1,3-benzodioxol-5-yl)methanone (Example 42),

[4-Amino-2-[[4-[4-(1-methylethyl)-1-piperazinyl]phenyl]amino]-5-thiazolyl](3-methoxyphenyl)methanone (Example 43),

[4-Amino-2-[[4-[4-(1-methylethyl)-1-piperazinyl]phenyl]amino]-5-thiazolyl](3,5-dimethoxyphenyl)methanone (Example 44), N-[4-[[4-Amino-2-[[4-[4-(1-methylethyl)-1-piperazinyl] phenyl]amino]-5-thiazolyl]carbonyl]phenyl]acetamide (Example 45),

[4-Amino-2-[[4-[4-(1-methylethyl)-1-piperazinyl]phenyl]amino]-5-thiazolyl][4-(diethylamino)phenyl]methanone (Example 46), 1-Acetyl-4-[4-[[4-amino-5-[(1,3-benzodioxol-5-yl)carbonyl]-2-thiazolyl]amino]phenyl]piperazine (Example 47), 1-Acetyl-4-[4-[[4-amino-5-[4-(diethylamino)benzoyl]-2-thiazolyl]amino]phenyl]piperazine, trifluoroacetate salt (Example 48),

[4-Amino-2-[[4-[4-(2-hydroxyethyl)-1-piperazinyl]phenyl]amino]-5-thiazolyl](2,3-dihydro-1,4-benzodioxin-6-yl)methanone (Example 49),

[4-Amino-2-[[4-[4-(2-hydroxyethyl)-1-piperazinyl]phenyl]amino]-5-thiazolyl][4-(1-pyrrolidinyl)phenyl]methanone (Example 50),

[4-Amino-2-[[4-[4-(2-hydroxyethyl)-1-piperazinyl]phenyl]amino]-5-thiazolyl](3-fluorophenyl)methanone (Example 51),

[4-Amino-2-[[4-[4-(2-hydroxyethyl)-1-piperazinyl]phenyl]amino]-5-thiazolyl](3,5-difluorophenyl)methanone (Example 52),

[4-Amino-2-[[4-[4-(2-hydroxyethyl)-1-piperazinyl]phenyl]amino]-5-thiazolyl](3-methoxyphenyl)methanone (Example 53),

[4-Amino-2-[[4-(1-piperazinyl)phenyl]amino]-5-thiazolyl](3-fluorophenyl)methanone (Example 54),

[4-Amino-2-[[4-(1-piperazinyl)phenyl]amino)-5-thiazolyl][4-(1-pyrrolidinyl)phenyl]methanone (Example 55),

[4-Amino-2-[[4-(1-piperazinyl)phenyl]amino)-5-thiazolyl](3-fluoro-4-methoxyphenyl)methanone (Example 56),

[4-Amino-2-[[4-(4-methyl-1-piperazinyl)phenyl]amino]-5-thiazolyl][4-(2-hydroxyethyl)amino-3-nitrophenyl]methanone (Example 57),

[4-Amino-2-[[4-(4-methyl-1-piperazinyl)phenyl]amino]-5-thiazolyl][3-nitro-4-(1-pyrrolidinyl)phenyl]methanone (Example 58),

[4-Amino-2-[[4-(4-methyl-1-piperazinyl)phenyl]amino]-5-thiazolyl][3-nitro-4-(4-morpholinyl)phenyl]methanone (Example 59),

[4-Amino-2-[[4-(4-methyl-1-piperazinyl)phenyl]amino]-5-thiazolyl][3-nitro-4-[(2-methoxyethyl)amino]phenyl]methanone (Example 60), racemic [4-Amino-2-[[4-(4-methyl-1-piperazinyl)phenyl]amino]-5-thiazolyl][3-nitro-4-[3-(hydroxymethyl)-1-piperidinyl]phenyl]methanone (Example 61), racemic [4-Amino-2-[[4-(4-methyl-1-piperazinyl)phenyl]amino]-5-thiazolyl][3-nitro-4-(2-methyl-1-pyrrolidinyl)phenyl]methanone (Example 62), (R)-[4-Amino-2-[[4-(4-methyl-1-piperazinyl)phenyl]amino]-5-thiazolyl][3-nitro-4-[[1-(hydroxymethyl)-3-methylbutyl]amino]phenyl]methanone (Example 63),

[4-Amino-2-[[4-(4-methyl-1-piperazinyl)phenyl]amino]-5-thiazolyl][3-nitro-4-(4-hydroxy-1-piperidinyl)phenyl]methanone (Example 64),

[4-Amino-2-[[4-(4-methyl-1-piperazinyl)phenyl]amino]-5-thiazolyl][3-amino-4-(4-pyrrolidinyl)phenyl]methanone (Example 65), (R)-[3-Amino-4-[[1-(hydroxymethyl)-3-methylbutyl]amino]phenyl][4-amino-2-[[4-(4-methyl-1-piperazinyl)phenyl]amino]-5-thiazolyl]methanone (Example 66),

[4-Amino-2-[[3-fluoro-4-(4-methyl-1-piperazinyl)phenyl]amino]-5-thiazolyl](2,3-dihydro-1,4-benzodioxin-5-yl)methanone (Example 67),

[4-Amino-2-[[3-fluoro-4-(4-methyl-1-piperazinyl)phenyl]amino]-5-thiazolyl][4-(1-pyrrolidinyl)phenyl]methanone (Example 68), {4-Amino-2-[4-(4-isopropyl-piperazin-1-yl)-phenylamino]-thiazol-5-yl}-(3-methoxy-phenyl)-methanone, phosphoric acid (Example 69), {4-Amino-2-[4-(4-methyl-piperazin-1-yl)-phenylamino]-thiazol-5-yl}(3-methylsulfanyl-phenyl)-methanone (Example 70).

(4-Amino-2-{4-[4-(3-hydroxy-propyl)-piperazin-1-yl]-phenylamino}-thiazol-5-yl)-(3-fluoro-phenyl)-methanone (Example 71), (4-Amino-2-{4-[4-(3-hydroxy-propyl)-piperazin-1-yl]-phenylamino}-thiazol-5-yl)-(3-methoxy-phenyl)-methanone (Example 72), 3-(4-Amino-2-{4-[4-(3-hydroxy-propyl)-piperazin-1-yl]-phenylamino}-thiazole-5-carbonyl)-benzonitrile (Example 73), (4-Amino-2-{4-[4-(3-hydroxy-propyl)-piperazin-1-yl]-phenylamino}-thiazol-5-yl)-(3-nitro-phenyl)-methanone (Example 74), (4-Amino-2-{4-[4-(3-hydroxy-propyl)-piperazin-1-yl]-phenylamino}-thiazol-5-yl)-m-tolyl-methanone (Example 75), (4-Amino-2-{4-[4-(3-hydroxy-propyl)-piperazin-1-yl]-phenylamino}-thiazol-5-yl)-(3-ethyl-phenyl)-methanone (Example 76), {4-Amino-2-[4-(4-methyl-piperazin-1-yl)-phenylamino]-thiazol-5-yl)(3-ethyl-phenyl)-methanone (Example 77), {4-Amino-2-[4-(4-methyl-piperazin-1-yl)-phenylamino]-thiazol-5-yl}-m-tolyl-methanone (Example 78), 3-{4-Amino-2-[4-(4-isopropyl-piperazin-1-yl)-phenylamino]-thiazole-5-carbonyl}-benzonitrile (Example 79).

{4-Amino-2-[4-(4-isopropyl-piperazin-1-yl)-phenylamino]-thiazol-5-yl}-(3-fluoro-phenyl)-methanone, with hydrogen bromide (Example 80), {4-Amino-2-[4-(4-isopropyl-piperazin-1-yl)-phenylamino]-thiazol-5-yl}-(3,4,5-trifluoro-phenyl)-methanone, with hydrogen bromide (Example 81), {4-Amino-2-[4-(4-isopropyl-piperazin-1-yl)-phenylamino]-thiazol-5-yl}-(3,5-difluoro-phenyl)-methanone, with hydrogen bromide (Example 82), 4-Amino-2-{4-[4-(2-methoxy-ethyl)-piperazin-1-yl]-phenylamino}-thiazol-5-yl)-(3-fluoro-4-methoxy-phenyl)-methanone, hydrogen bromide (Example 83), {4-Amino-2-[4-(4-isopropyl-piperazin-1-yl)-phenylamino]-thiazol-5-yl}-(4-fluoro-3-methoxy-phenyl)-methanone, with hydrogen bromide (Example 84), {4-Amino-2-[4-(4-isopropyl-piperazin-1-yl)-phenylamino]-thiazol-5-yl}-(3-fluoro-4-methoxy-phenyl)-methanone, with hydrogen bromide (Example 85), {4-Amino-2-[4-(4-isopropyl-piperazin-1-yl)-phenylamino]-thiazol-5-yl}-(4-difluoromethoxy-phenyl)-methanone, with hydrogen bromide (Example 86), {4-Amino-2-[4-(4-isopropyl-piperazin-1-yl)-phenylamino]-thiazol-5-yl}(3-trifluoromethoxy-phenyl)-methanone, with hydrogen bromide (Example 87), {4-Amino-2-[4-(4-isopropyl-piperazin-1-yl)-phenylamino]-thiazol-5-yl}-(4-piperidin-1-yl-phenyl]-methanone, with hydrogen bromide (Example 88), {4-Amino-2-[4-(4-isopropyl-piperazin-1-yl)-phenylamino]-thiazol-5-yl}-(4-morpholin-4-yl-phenyl)-methanone, with hydrogen bromide (Example 89), (4-Amino-2-{4-[4-(2-methoxy-ethyl)-piperazin-1-yl]-phenylamino}-thiazol-5-yl)-(3,5-difluoro-phenyl)-methanone, with hydrogen bromide (Example 90), (4-Amino-2-{4-[4-(2-methoxy-ethyl)-piperazin-1-yl]-phenylamino}-thiazol-5-yl)-(3,4-difluoro-phenyl)-methanone, with hydrogen bromide (Example 91), (4-Amino-2-{4-[4-(2-methoxy-ethyl)-piperazin-1-yl]-phenylamino}-thiazol-5-yl)-(3-methoxy-phenyl)-methanone, with hydrogen bromide (Example 92), (4-Amino-2-{4-[4-(2-methoxy-ethyl)-piperazin-1-yl]-phenylamino}-thiazol-5-yl)-benzo[1,3]dioxol-5-yl-methanone, with hydrogen bromide (Example 93), 4-Amino-2-{4-[4-(2-methoxy-ethyl)-piperazin-1-yl]-phenylamino}-thiazol-5-yl)-(2,3-dihydro-benzo[1,4]dioxin-6-yl)-methanone, with hydrogen bromide (Example 94), {4-Amino-2-[4-(4-methyl-piperazin-1-yl)-phenylamino]-thiazol-5-yl}-(3,5-difluoro-phenyl)-methanone, with hydrogen bromide (Example 95), {4-Amino-2-[4-(4-methyl-piperazin-1-yl)-phenylamino]-thiazol-5-yl}-(3,5-difluoro-4-methoxy-phenyl)-methanone, with hydrogen bromide (Example 96), {4-Amino-2-[4-(4-methyl-piperazin-1-yl)-phenylamino]-thiazol-5-yl}-(4-fluoro-3-methoxy-phenyl)-methanone, with hydrogen bromide (Example 97), {4-Amino-2-[4-(4-methyl-piperazin-1-yl)-phenylamino]-thiazol-5-yl}-(3-trifluoromethoxy-phenyl)-methanone, with hydrogen bromide (Example 98), (4-Amino-2-{4-[4-(2-hydroxy-ethyl)-piperazin-1-yl]-phenylamino}-thiazol-5-yl)-(3-fluoro-phenyl)-methanone, with acetic acid (Example 99),

[4-Amino-2-(4-piperazin-1-yl-phenylamino)-thiazol-5-yl]-(3,4,5-trifluoro-phenyl)-methanone, with acetic acid (Example 100),

[4-Amino-2-(4-piperazin-1-yl-phenylamino)-thiazol-5-yl]-(3,5-difluoro-4-methoxy-phenyl)-methanone, with acetic acid (Example 101),

[4-Amino-2-(4-piperazin-1-yl-phenylamino)-thiazol-5-yl]-(4-fluoro-3-methoxy-phenyl)-methanone, with acetic acid (Example 102),

[4-Amino-2-(4-piperazin-1-yl-phenylamino)-thiazol-5-yl]-(3-trifluoromethoxy-phenyl)-methanone, with acetic acid (Example 103), {4-Amino-2-[4-(4-sec-butyl-piperazin-1-yl)-phenylamino]-thiazol-5-yl}-(3-fluoro-phenyl)-methanone (Example 104), {4-Amino-2-[4-(4-sec-butyl-piperazin-1-yl)-phenylamino]-thiazol-5-yl}-benzo[1,3]dioxol-5-yl-methanone (Example 105), {4-Amino-2-[4-(4-sec-butyl-piperazin-1-yl)-phenylamino]-thiazol-5-yl}-(2,3-dihydro-benzo[1,4]dioxin-6-yl)-methanone (Example 106), {4-Amino-2-[4-(4-cyclopentyl-piperazin-1-yl)-phenylamino]-thiazol-5-yl}-benzo[1,3]dioxol-5-yl-methanone (Example 107), {4-Amino-2-[4-(4-cyclopentyl-piperazin-1-yl)-phenylamino]-thiazol-5-yl}-(2,3-dihydro-benzo[1,4]dioxin-6-yl)-methanone (Example 108), {4-Amino-2-[4-(4-isopropyl-piperazin-1-yl)-phenylamino]-thiazol-5-yl}-(3-trifluoromethoxy-phenyl)-methanone (Example 109), {4-Amino-2-[4-(4-isopropyl-piperazin-1-yl)-phenylamino]-thiazol-5-yl}-(3-fluoro-phenyl)-methanone (Example 110), {4-Amino-2-[4-(4-isopropyl-piperazin-1-yl)-phenylamino]-thiazol-5-yl}-(3-difluoromethoxy-phenyl)-methanone (Example 111), {4-Amino-2-[4-(4-isopropyl-piperazin-1-yl)-phenylamino]-thiazol-5-yl}-(3-hydroxy-phenyl)-methanone, with acetic acid (Example 112), {4-Amino-2-[4-(4-isobutyl-piperazin-1-yl)-phenylamino]-thiazol-5-yl}-(3-hydroxy-phenyl)-methanone, with acetic acid (Example 113),

[4-Amino-2-(4-piperazin-1-yl-phenylamino)-thiazol-5-yl]-(3-difluoromethoxy-phenyl)-methanone (Example 114), {4-Amino-2-[4-(4-cyclopropylmethyl-piperazin-1-yl)-phenylamino]-thiazol-5-yl}-(3-difluoromethoxy-phenyl)-methanone (Example 115), {4-Amino-2-[4-(4-cyclopropylmethyl-piperazin-1-yl)-phenylamino]-thiazol-5-yl}-(3-methoxy-phenyl)-methanone (Example 116), {4-Amino-2-[4-(4-cyclopropylmethyl-piperazin-1-yl)-phenylamino]-thiazol-5-yl}-benzo[1,3]dioxol-5-yl-methanone (Example 117), {4-Amino-2-[4-(4-cyclopropylmethyl-piperazin-1-yl)-phenylamino]-thiazol-5-yl}-(2,3-dihydro-benzo[1,4]dioxin-6-yl)-methanone (Example 118), {4-Amino-2-[4-(4-cyclopropylmethyl-piperazin-1-yl)-phenylamino]-thiazol-5-yl}-(3-fluoro-4-hydroxy-phenyl)-methanone (Example 119), {4-Amino-2-[4-(4-methyl-piperazin-1-yl)-phenylamino]-thiazol-5-yl}-(3-difluoromethoxy-phenyl)-methanone (Example 120), {4-Amino-2-[4-(4-cyclopropylmethyl-piperazin-1-yl)-phenylamino]-thiazol-5-yl}-(3-fluoro-phenyl)-methanone (Example 121), {4-Amino-2-[4-(4-cyclopropylmethyl-piperazin-1-yl)-phenylamino]-thiazol-5-yl}-(3-fluoro-4-methoxy-phenyl)-methanone (Example 122), {4-Amino-2-[4-(4-methyl-piperazin-1-yl)-phenylamino]-thiazol-5-yl}-(3-hydroxy-phenyl)-methanone (Example 123), and {4-Amino-2-[4-(4-methyl-piperazin-1-yl)-phenylamino]-thiazole-5-carbonyl}-benzonitrile (Example 124).

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to one of the below described synthetic routes.

A. Ring Formation

Compounds of the invention can be prepared by the alkylation and cyclization of a number of thiourea derivatives, as shown in Scheme I, using reactions that are known. Among the thiourea derivatives that can be used are nitroamidinothioureas (Binu, R. et al. *Org. Prep. Proced. Int.* 1998, 30, 93–96); 1-[(arylthiocarbamoyl)amino]-3,5-dimethylpyrazoles (Jenardanan, G. C. et al. *Synth. Commun.* 1997, 27, 3457–3462); and N-(aminoiminomethyl)-N'-phenylthioureas (Rajasekharan, K. N. et al. *Synthesis* 1986, 353–355).

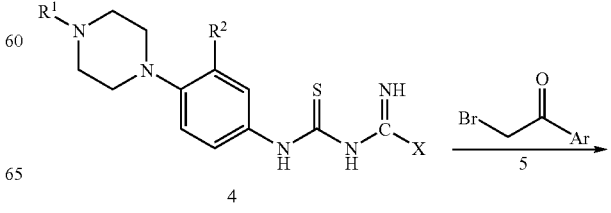

Scheme I

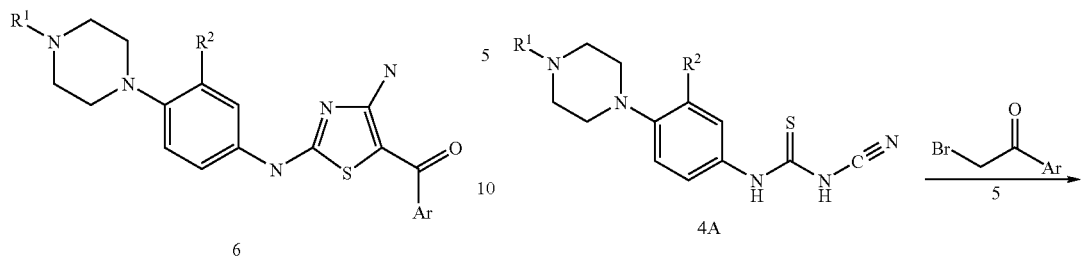

Another thiourea derivative that can be used for the preparation of compounds of the invention by alkylation and cyclization is N-cyanothiourea (Gewald, K. et al. *J. Prakt. Chem.* 1967, 97–104). For example, pursuant to Scheme IA below, an N-cyanothiourea of formula 4A can be reacted with a halomethylketone, such as a bromomethylketone of formula 5, at a temperature between around room temperature and around 65° C., to give a compound of formula 6.

Scheme IA

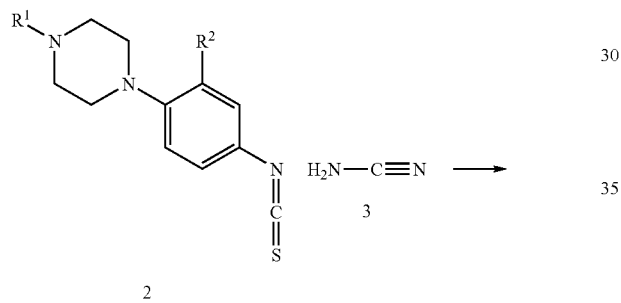

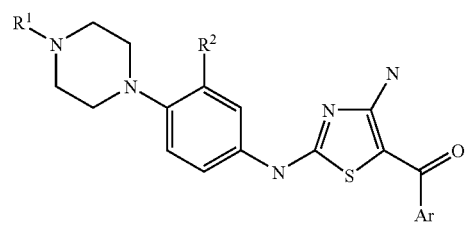

Alternatively, the compounds of the invention are also conveniently prepared by reaction of a resin-bound substituted (aminothioxomethyl) carbamimidothioic acid methyl ester of formula 8 with a bromomethyl aryl ketone of formula 5 as shown in Scheme II below.

Scheme II

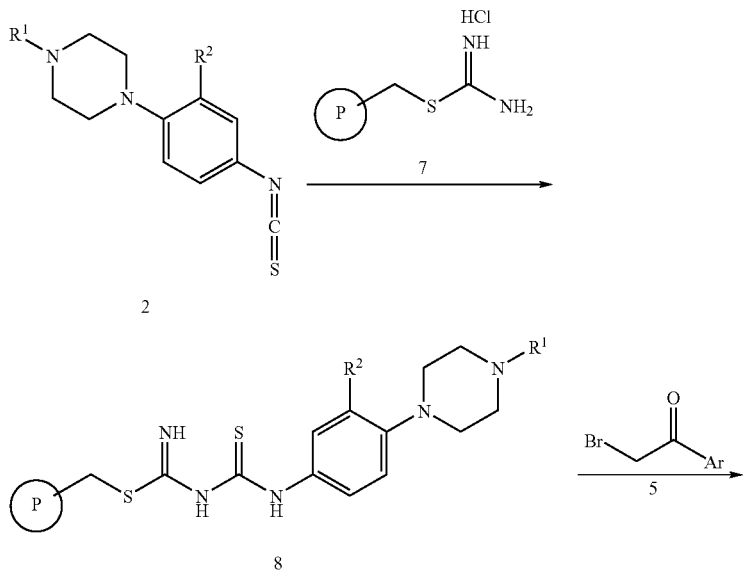

-continued

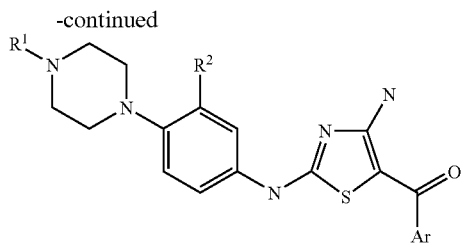

6

The resin-bound thiourea derivative of formula 8 can be made by any conventional procedure known to one skilled in the art of organic synthesis. For example, it can be conveniently prepared by the reaction of a resin-bound thiouronium salt of formula 7 with an isothiocyanate of formula 2 in the presence of a base, such as a tertiary amine (e.g., triethylamine or diisopropylethylamine) in an inert solvent, such as a polar aprotic solvent (e.g., N,N-dimethylformamide). The reaction is conveniently carried out at a temperature around room temperature. The resin-bound thiourea derivative of formula 8 is then converted to the product of formula 6 by treatment with a halomethylketone (for example, a bromomethylketone of formula 5) in a suitable inert solvent such as a polar aprotic solvent (e.g., N,N-dimethylformamide) at a temperature around room temperature.

B. Nucleophilic Aromatic Substitution $R^{20}$ and $R^{21}$ are independently selected from H and lower alkyl which itself can be substituted by OH, or alternatively, $NR^{20}R^{21}$ can optionally form a ring having 5–6 atoms, said ring including one or more additional hetero atoms and being optionally substituted by OH and lower alkyl which itself maybe substituted by OH) and $R^5$ represents hydrogen (that is to say, compounds of formula 10), can be conveniently prepared by treating a compound of formula 9, with an amine of formula $HNR^{21}R^{20}$, in the optional presence of an additional base, such as a tertiary amine (e.g., triethylamine or diisopropylethylamine) in an inert solvent, such as a lower alcohol (e.g., ethanol, isopropanol, n-butanol, or the like) or a polar aprotic solvent (e.g., N,N-dimethylformamide). The reaction is conveniently carried out a temperature between about 70 degrees and about 110 degrees, preferably at about the reflux temperature of the solvent or about 100 degrees, whichever is lower.

C. Removal of Protective Groups

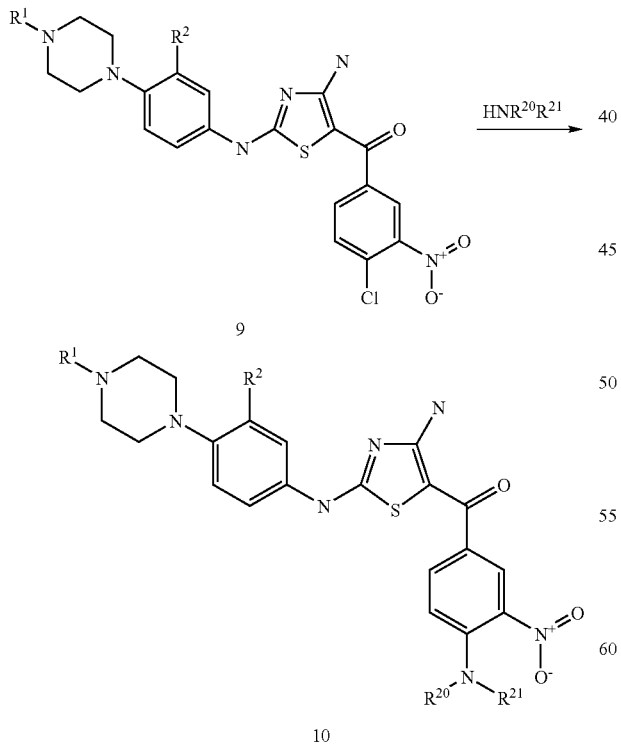

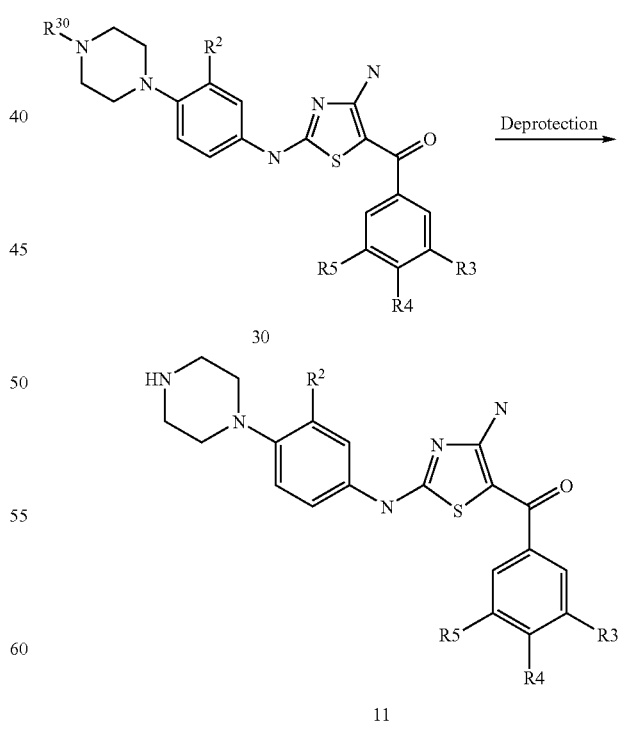

As shown in Scheme III above, compounds of formula 1 where $R^3$ represents nitro, $R^4$ represents $NR^{20}R^{21}$ (wherein As shown in Scheme IV, compounds of formula I where $R^1$ represents H (that is, compounds of formula 11) can be prepared by removal of a protective group from compounds of formula 30 where $R^{30}$ represents a protective group commonly used for the protection of a secondary amine. Many such protective groups are known to those of skill in the art of organic synthesis. For example, several suitable protective groups are enumerated in "protective Groups in Organic Synthesis" (Greene, T. W. and Wuts, P. G. M., $2^{nd}$ Edition, John Wiley & Sons, N.Y. 1991). Preferred protective groups are those compatible with the reaction conditions used to prepare compounds of the invention. One such protective group is the tert-butoxycarbonyl (t-BOC) group. The tert-butoxy carbonyl group can be conveniently removed by treatment of a compound of formula 30 in which $R^{30}$ represents

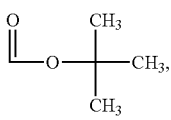

with an acid to give a compound of formula I in which $R^1$ represents H. Examples of acids that can be used to effect this transformation are well known, and include trifluoroacetic acid, hydrochloric acid, hydrofluoric acid, and aluminum chloride. For example, the t-BOC group may be conveniently removed by treating a compound of formula 30 in which $R^{30}$ represents

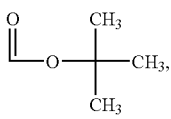

with trifluoroacetic acid, in an inert solvent, such as a halogenated hydrocarbon (e.g., dichloromethane). The reaction can be carried out at a temperature between about 0 degrees and about room temperature, preferably at about room temperature.

D. Separating a Mixture of Stereoisomers into the Optically Pure Stereoisomers (When Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, NY, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87–124).

E. Converting a Compound of Formula I that Bears a Basic Nitrogen into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluenesulfonic acid, or the like.

F. Converting a Compound of Formula I that Bears a Carboxylic Acid Group into a Pharmaceutically Acceptable Alkali Metal Salt The optional conversion of a compound of formula I that bears a carboxylic acid group into a pharmaceutically acceptable alkali metal salt can be effected by conventional means. For example, the compound can be treated with an inorganic base such as lithium hydroxide, sodium hydroxide, potassium hydroxide, or the like.

G. Converting a Compound of Formula I that Bears a Carboxylic Acid Group into a Pharmaceutically Acceptable Ester The optional conversion of a compound of formula I that bears a carboxylic acid group into a pharmaceutically acceptable ester can be effected by conventional means. The conditions for the formation of the ester will depend on the stability of the other functional groups in the molecule to the reaction conditions. If the other moieties in the molecule are stable to acidic conditions, the ester may be conveniently prepared by heating in a solution of a mineral acid (e.g., sulfuric acid) in an alcohol. Other methods of preparing the ester, which may be convenient if the molecule is not stable to acidic conditions include treating the compound with an alcohol in the presence of a coupling agent and in the optional presence of additional agents that may accelerate the reaction. Many such coupling agents are known to one skilled in the art of organic chemistry. Two examples are dicyclohexylcarbodiimide and triphenylphosphine/diethyl azodicarboxylate. In the case where dicyclohexylcarbodiimide is used as the coupling agent, the reaction is conveniently carried out by treating the acid with the alcohol, dicyclohexylcarbodiimide, and the optional presence of a catalytic amount (0–10 mole %) of N,N-dimethylaminopyridine, in an inert solvent such as a halogenated hydrocarbon (e.g., dichloromethane) at a temperature between about 0 degrees and about room temperature, preferably at about room temperature. In the case where triphenylphosphine/diethyl azodicarboxylate is used as the coupling agent, the reaction is conveniently carried out by treating the acid with the alcohol, triphenylphosphine and diethyl azodicarboxylate, in an inert solvent such as an ether (e.g., tetrahydrofuran) or an aromatic hydrocarbon (e.g., benzene) at a temperature between about 0 degrees and about room temperature, preferably at about 0 degrees.

Turning to the intermediates, isothiocyanate intermediates of formula 2 used to make compounds of the invention can be made by any conventional means. For example, they may be made by the route shown in Scheme V below.

Scheme V

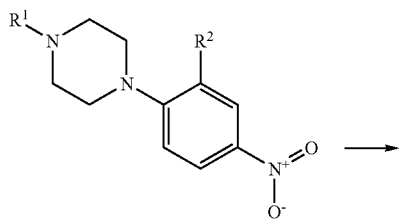

12

-continued

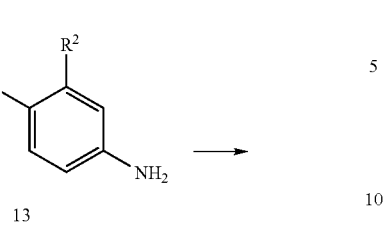

13

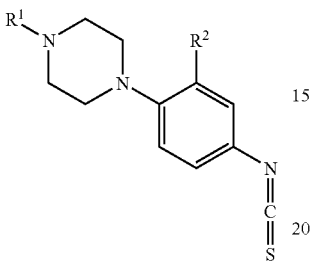

2

The nitro group in a compound of formula 12 can be reduced to give an aniline of formula 13 using a number of methods familiar to one skilled in the art. These methods include (1) treatment of the nitro compound of formula 12 with iron/acetic acid, with tin(II) chloride/hydrochloric acid, or with zinc and ammonium chloride; and (2) hydrogenation in the presence of a noble metal catalyst such as palladium-on-carbon.

The isothiocyanates of formula 2 may be made from anilines of formula 13 using any one of a number of reagents known to those skilled in organic synthesis to be useful for the transformation of an aniline of formula 13 into an isothiocyanate of formula 2. Among these reagents are carbon disulfide, thiophosgene, 1,1'-thiocarbonylbis(2-pyridone), and thiocarbonyl diimidazole. The reaction can be carried out by treating an aniline of formula 13 with thiocarbonyl diimidazole in a suitable inert solvent such as a polar aprotic solvent (e.g., N,N-dimethylformamide) at a temperature between about −20 degrees and about 0 degrees, preferably at about −15 degrees.

Nitro compounds of formula 12 can be made by a variety of methods that are known in the field of organic synthesis. For example, they may be made by the nucleophilic substitution of a nitrobenzene derivative that bears a leaving group at the position para to the nitro group in accordance with Scheme VI below:

Scheme VI

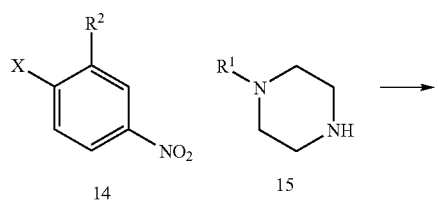

-continued

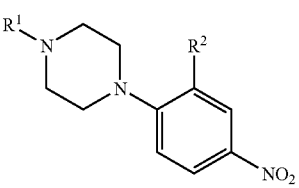

12

The nucleophilic substitution reaction between an amine of formula 15 and a nitrobenzene of formula 14 (wherein X is a leaving group) to give the substituted product of formula 12 can be conveniently carried out by heating these materials together at a temperature between about 50 and about 100 degrees, preferably at about 80 degrees, in the optional presence of an inert solvent such as acetonitrile (Scheme VI). Suitable leaving groups of formula X include chloride and fluoride. By way of example and not as a limitation, the following compounds of formula 14 are available commercially from the noted vendors:

| Structure | Supplier |
|---|---|
| 4-chloronitrobenzene | Aldrich |
| 3,4-dichloronitrobenzene | Aldrich |
| 3,4-difluoronitrobenzene | Aldrich |
| 3-chloro-4-methylnitrobenzene | Lancaster Synthesis |
| 3-fluoro-4-methylnitrobenzene | Aldrich |

Alternatively, nitro compounds of formula 12 may be synthesized according to Scheme VII below.

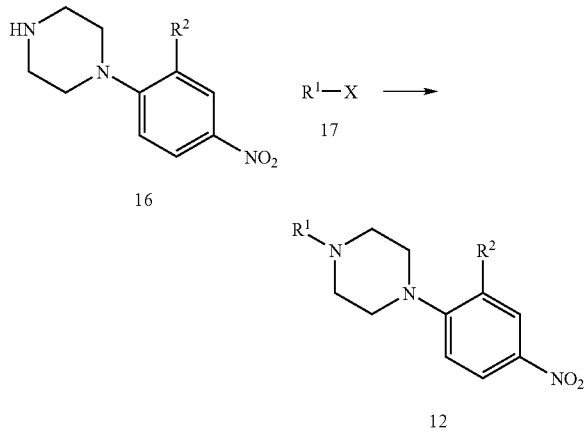

The alkylation of compounds of formula 16 to give compounds of formula 12, in which $R^1$ represents an alkyl group can be achieved by treating the compound with an alkylating agent of formula 17, in which X represents one of a number of leaving groups well known to those with knowledge of organic synthesis, such as a halide (e.g., chloride, bromide, iodide) or a sulfonate (e.g., mesylate, tosylate, triflate), or the like, in an inert solvent, such as acetonitrile, a lower alkyl ketone (e.g., acetone or 2-butanone), a polar aprotic solvent (e.g., N,N-dimethylformamide), or an aromatic hydrocarbon (e.g., benzene or toluene), in the presence of a base, such as sodium carbonate or potassium carbonate, and in the optional presence of a catalyst such as potassium iodide. Except where the leaving group is triflate, the reaction can be conveniently carried out at a temperature between about 50 degrees and about 110 degrees, preferably at about 80 degrees. Where the leaving group is triflate, the reaction is conveniently carried out at a temperature between about 0 degrees and room temperature, preferably at about room temperature.

Compounds of formula 12 where, $R^1$ represents an acyl group may be, prepared by acylation of compounds of formula 16. The reaction can be effected using known methods. For example, the compound of formula 16 can be treated with a carboxylic acid of formula 17, in which X represents OH, in the presence of a coupling agent, many examples of which are well known per se in peptide chemistry, and in the optional presence of a substance that increases the rate of the reaction, such as 1-hydroxybenzotriazole or 1-hydroxy-7-azabenzotriazole; or by reaction of the compound of formula 16 with a reactive derivative of carboxylic acids such as the corresponding acid halides (for example, the acid chloride), acid anhydride, mixed anhydride, activated ester, etc. The reaction is conveniently carried out by treating the compound of formula 16 with an acid chloride in the presence of a base such as pyridine, or a tertiary amine (e.g., diisopropylethylamine) or an inorganic base such as sodium or potassium carbonate, in an inert solvent such as a halogenated hydrocarbon (e.g., dichloromethane) at a temperature between about 0 degrees and about room temperature, preferably at about room temperature.

Compounds of formula 12 where $R^1$ represents an alkoxycarbonyl group may be prepared by the alkoxycarbonylation of compounds of formula 16 to give compounds of formula 12, in which $R^1$ represents an alkoxycarbonyl group. This synthesis can be effected using reactions that are well known in the fields of organic chemistry and peptide chemistry. Conditions for many of these reactions are given in "Protective Groups in Organic Synthesis" (Greene, T. W. and Wuts, P. G. M., $2^{nd}$ Edition, John Wiley & Sons, N.Y. 1991). In the case of the preferred alkoxycarbonyl protective group, namely the tert-butoxycarbonyl (t-BOC) group, the protective group can be introduced by reacting the amine of formula 16 with di-tert-butyl dicarbonate in an inert solvent such as a mixture of water and an ether such as dioxane, or in a halogenated solvent (such as dichloromethane), or in acetonitrile, in the optional presence of a base or of a catalyst, such as N,N-dimethylamino-pyridine. As an alternative to di-tert-butyl dicarbonate, the following reagents could also be used: 2-(tert-butoxycarbonyloximino)-2-phenylacetonitrile, or tert-butyl azidoformate.

Compounds of formula 12 where $R^1$ represents a sulfonyl group may be prepared by the sulfonylation of compounds of formula 16 to give compounds of formula 12, in which $R^1$ represents a sulfonyl group. This synthesis can be effected using reactions that are well known in the field of organic chemistry. For example, compounds of formula 12 in which $R^1$ represents a sulfonyl group can be prepared by reaction of compounds of formula 16 with a sulfonyl chloride in the presence of an appropriate base for example pyridine that can also be used as solvent. The reaction may also be performed by using a tertiary amine as the base, in the presence of an inert solvent such as tetrahydrofuran or dichloro-methane; or in aqueous solution using an alkali metal hydroxide such as sodium hydroxide as the base. The reaction is conveniently carried out at a temperature of between about room temperature and about 80 degrees, preferably at about room temperature.

Sample compounds of formula 16 may be obtained as indicated below.

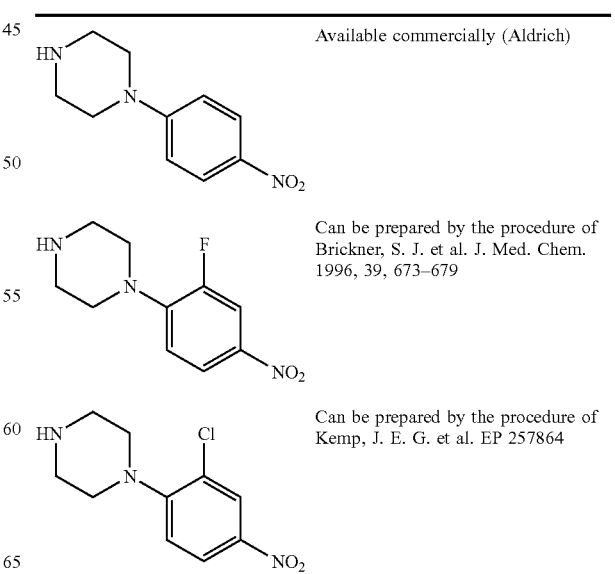

| | |
|---|---|
| 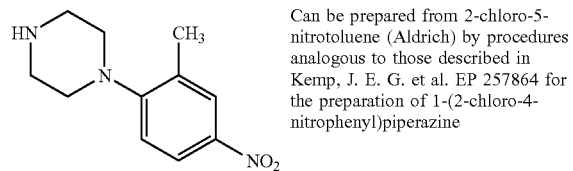 | Can be prepared from 2-chloro-5-nitrotoluene (Aldrich) by procedures analogous to those described in Kemp, J. E. G. et al. EP 257864 for the preparation of 1-(2-chloro-4-nitrophenyl)piperazine |

Bromomethylketone intermediates 5 used to make compounds of the invention are available commercially or can be made using one of a number of methods known to those skilled in the art of organic synthesis, for example: Friedel-Crafts reactions of an arene with bromoacetyl bromide or bromoacetyl chloride; oxidation of a 2-bromo-1-phenethyl alcohol; reaction of a diazomethyl ketone with HBr; reduction of a dibromomethyl ketone (see Scheme VIII) below; or reaction of a methyl ketone with a brominating agent (see Scheme IX) such as bromine, copper(II) bromide, tetrabutylammonium tribromide, or 5,5-dibromo-barbituric acid.

According to the method of Diwu et al. (Tetrahedron Lett. 1998, 39, 4987–4990), methyl ketones, of formula 19 can be converted into the corresponding dibromomethyl ketones of formula 20 by treatment with bromine in neat sulfuric acid. The dibromomethyl ketones of formula 20 can then be converted into the desired bromomethyl ketones of formula 5 by reduction with diethylphosphite.

Scheme VIII

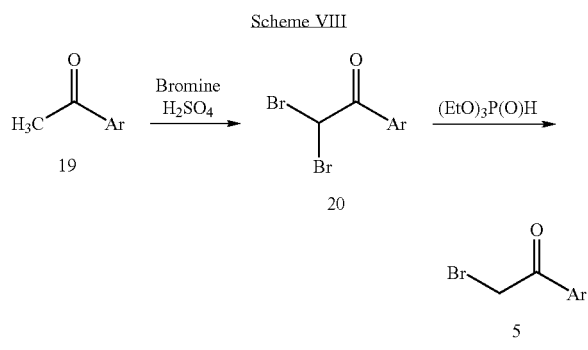

Bromomethyl ketones of formula 5 can also be prepared directly from methyl ketones of formula 19 using a variety of reagents well known to those of ordinary skill in the art of organic synthesis, such as those mentioned above. For example, the reaction may be conveniently carried out by treating the methyl ketone of formula 19 with bromine in a suitable inert solvent such as a halogenated hydrocarbon (e.g., carbon tetrachloride) in the optional presence of other agents that facilitate the reaction, such as a Bronsted or Lewis acid catalyst (e.g., aluminum chloride or acetic acid). The optimal reaction temperature depends on whether or not a catalyst is used. In the case where aluminum chloride is used, the reaction is conveniently carried out at about 0 degrees. In the cases where acetic acid is added, or where no catalyst is used, the reaction is conveniently carried out at a temperature between about room temperature and about 80 degrees, preferably at about room temperature. Alternatively, a methyl ketone of formula 19 may be converted to a bromomethylketone of formula 5 by treatment with copper (II) bromide in a suitable unreactive solvent such as ethyl acetate, preferably at the reflux temperature.

Scheme IX

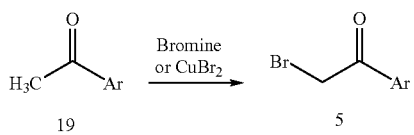

Compositions/Formulations

In an alternative embodiment, the present invention is directed to pharmaceutical compositions comprising at least one compound of formula I, or a pharmaceutically acceptable salt or ester thereof.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, in particular oncological disorders. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount, is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Starting Materials

In another embodiment, the present invention is also directed to novel intermediates useful in the preparation of compounds of formula I. These novel intermediates include the following compounds:

1-(2-Fluoro-4-isothiocyanatophenyl)-4-methylpiperazine (Example 2C),
1-(1-Methylethyl)-4-(4-nitrophenylpiperazine) (Example 3A),
4-[4-(1-Methylethyl)-1-piperazinyl]benzenamine (Example 3B),
1-(4-Isothiocyanatophenyl)-4-(1-methylethyl)piperazine (Example 3C),
4-(2-Hydroxyethyl)-1-(4-isothiocyanatophenyl)piperazine (Example 5B),
1-(4-Isothiocyanatophenyl)$_4$-(2-methoxy-ethyl)piperazine (Example 14B),
1-(4-Isothiocyanatophenyl)-4-(1-methylpropyl)piperazine (Example 14C),
4-Cyclopentyl-1-(4-isothiocyanatophenyl)piperazine (Example 14D),
1-(4-Isothiocyanatophenyl)-4-(2-methylpropyl)piperazine (Example 14E),
4-(3-Hydroxypropyl)-1-(4-isothiocyanatophenyl)piperazine (Example 14F),
2-Bromo-1-(3,4,5-trifluoro-phenyl)ethanone (Example 14H),
2-Bromo-1-(4-fluoro-3-methoxy-phenyl)ethanone (Example 14I),
2-Bromo-1-(4-fluoro-3-methoxy-phenyl)ethanone (Example 14K),
2-Bromo-1-(3-difluoromethoxy-phenyl)ethanone (Example 14L),
[4-amino-2-[[4-(4-methyl-1-piperazinyl)phenyl]amino]-5-thiazolyl](4-chloro-3-nitrophenyl)methanone (Example 15),
Carbamimidothioic acid, [[4-(4-methyl-1-piperazinyl)phenylamino]thioxomethyl], polymer bound (Example 18),
Carbamimidothioic acid, [[3-fluoro-4-(4-methyl-1-piperazinyl)phenylamino]thioxomethyl], polymer bound (Example 19),
Carbamimidothioic acid, [[4-[4-(1-methylethyl)-1-piperazinyl]phenylamino]thioxomethyl], polymer bound (Example 20),
Carbamimidothioic acid, [[4-(4-acetyl-1-piperazinyl)phenylamino]thioxomethyl], polymer bound (Example 21),
Carbamimidothioic acid, [[4-[4-(2-hydroxyethyl)-1-piperazinyl]phenylamino]thioxomethyl], polymer bound (Example 22),
Carbamimidothioic acid, [[4-[4-[(1,1-dimethylethoxy)carbonyl]-1-piperazinyl]phenylamino]thioxomethyl], polymer bound (Example 23A),
Carbamimidothioic acid, [[4-[4-(2-methoxyethyl)-1-piperazinyl]phenylamino]thioxomethyl], polymer bound (Example 23B),
Carbamimidothioic acid, [[4-[4-(1-methylpropyl)-1-piperazinyl]phenylamino]thioxomethyl], polymer bound (Example 23C),
Carbamimidothioic acid, [[4-(4-cyclopentyl-1-piperazinyl)phenylamino]thioxomethyl], polymer bound (Example 23D),
Carbamimidothioic acid, [[4-[4-(2-methylpropyl)-1-piperazinyl]phenylamino]thioxomethyl], polymer bound (Example 23E),
Carbamimidothioic acid, [[4-[4-(3-hydroxypropyl)-1-piperazinyl]phenylamino]thioxomethyl], polymer bound (Example 23F),
4-[4-[[4-Amino-5-fluorobenzoyl)-2-thiazolyl]amino]phenyl]-1-piperazinecarboxylic acid 1,1-dimethylethyl ester (Example 54A),
4-[4-[[4-Amino-5-[4-(1-pyrrolidinyl)benzoyl]-2-thiazolyl]amino]phenyl]-1-piperazinecarboxylic acid, 1,1-dimethylethyl ester (Example 55A),
4-[4-[[4-Amino-5-(3-fluoro-4-methoxybenzoyl)-2-thiazolyl]amino]phenyl]-1-piperazinecarboxylic acid, 1,1-dimethylethyl ester (Example-56A).

EXAMPLES

The following examples illustrate preferred methods for synthesizing the compounds and formulations of the present invention.

Example 1

1-(4-Isothiocyanatophenyl)-4-methylpiperazine

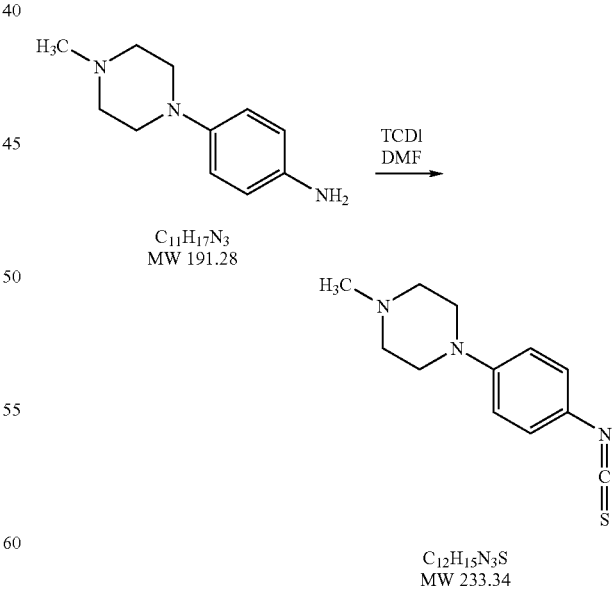

A mixture of thiocarbonyldiimidazole (4.46 g, 25.0 mmol) (Aldrich) and N,N-dimethylformamide (20 mL) was cooled to about −15° C. and a solution of 4-(4-methyl-1-piperazinyl)benzenamine (prepared according to the procedure of Chong, W. K. et al. WO9921845; 4.78 g, 25.00 mmol) was added over a period of 30 min. The cooling bath was removed and the mixture was stirred for 1 h. The mixture was cooled to 0° C. and ice-water was added. After 30 min, the mixture was extracted with ether (3×200 mL), dried (Na$_2$SO$_4$), filtered, and evaporated to give 1-(4-isothiocyanatophenyl)-4-methylpiperazine (4.84 g, 83%) as a pale purple solid.

Example 2

1-(2-Fluoro-4-isothiocyanatophenyl)-4-methylpiperazine

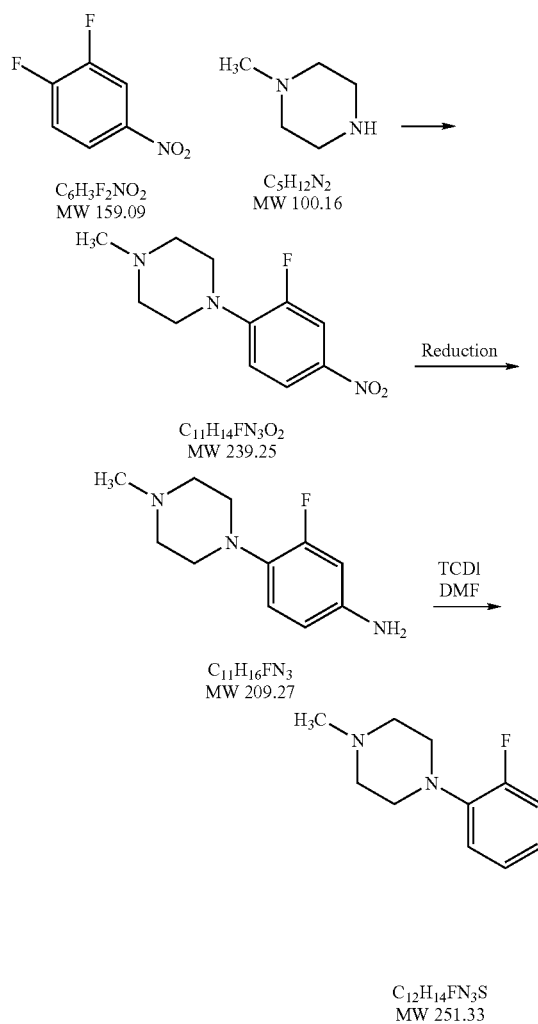

A. 1-(2-Fluoro-4-nitrophenyl)-4-methylpiperazine

A solution of 3,4-difluoronitrobenzene (12.00 g, 75.4 mmol) (Aldrich) and N-methylpiperazine (18.89 g, 188.6 mmol) in acetonitrile (150 mL) was heated at reflux for 3 h. The reaction mixture was allowed to stand overnight at room temperature, then the solvent was evaporated under reduced pressure and the residue was partitioned between water and ethyl acetate (200 mL each). The aqueous layer was extracted with ethyl acetate (3×200 mL) and the combined organic layers were then washed with water and brine (200 mL each), dried (MgSO4), filtered, and evaporated under reduced pressure to give 1-(2-fluoro-4-nitrophenyl)-4-methylpiperazine as a pale brown solid (17.5 g, 97%, mp 68–70° C.).

B. 3-Fluoro-4-(4-methyl-1-piperazinyl)benzenamine

A solution of 1-(2-fluoro-4-nitrophenyl)-4-methylpiperazine (5.00 g, 20.9 mmol) (from Step A above) and 10% palladium-on-carbon (0.20 g, 0.2 mmol) in ethyl acetate (100 mL) and ethanol (50 mL) was hydrogenated at 50 psi in a Parr shaker for 4 h. The mixture was filtered through Celite™. The Celite™ was washed with ethyl acetate (50 mL) and the solvent was evaporated to give 3-fluoro-4-(4-methyl-1-piperazinyl)benzenamine as a white solid (4.05 g, 93%, mp 89–91° C.).

C. 1-(2-Fluoro-4-isothiocyanatophenyl)-4-methylpiperazine

Thiocarbonyl diimidazole (3.00 g, 3.53 mmol) (Aldrich) was dissolved in N,N-dimethylformamide (10 mL) and the solution was cooled to −10° C. (ice/acetone bath). A solution of 3-fluoro-4-(4-methyl-1-piperazinyl) benzenamine (2.26 g, 10.8 mmol) (from Step B above) in N,N-dimethylformamide (30 mL) was added over a period of 30 minutes, then the cooling bath was removed and the solution was stirred overnight. Ice-water was then added (100 mL) and the mixture was extracted with ether (3×200 mL). The combined ether layers were dried (MgSO4), filtered, and evaporated to give 1-(2-fluoro-4-isothio-cyanatophenyl)-4-methylpiperazine as a yellow oil that solidified on standing (3.88 g, 92%).

Example 3

1-(4-Isothiocyanatophenyl)-4-(1-methylethyl)piperazine

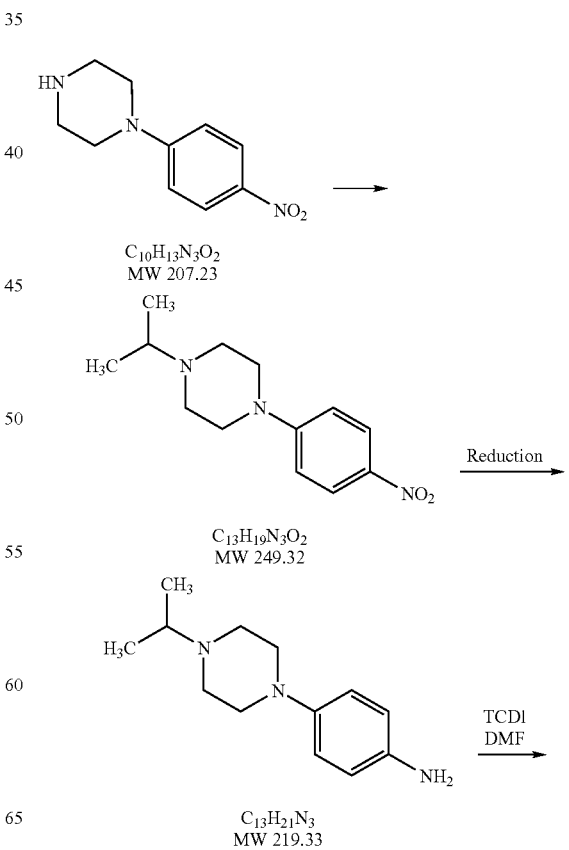

-continued

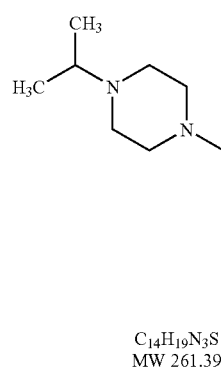

C₁₄H₁₉N₃S
MW 261.39

A. 1-(1-Methylethyl)-4-(4-nitrophenyl)piperazine)

A mixture of 1-(4-nitrophenyl)piperazine (2.00 g, 9.7 mmol) (Acros Organics), powdered potassium carbonate (2.7 g, 19.3 mmol), 2-bromopropane (0.96 mL, 10.1 mmol), potassium iodide (50 mg) and a catalytic amount of 18-crown-6 in acetonitrile (15 mL) was heated at reflux overnight. The mixture was filtered, and the filter cake was washed with acetonitrile. The solvent was evaporated from the combined filtrates and the residue was partitioned between water and ethyl acetate. The layers were separated and the aqueous layer was extracted twice with ethyl acetate. The combined organic layers were washed with brine, dried (MgSO4), filtered, evaporated and chromatographed (0–66% acetone/dichloromethane) to give 1-(1-methylethyl)-4-(4-nitrophenylpiperazine) (1.7 g, 71%).

B. 4-[4-(1-Methylethyl)-1-piperazinyl]benzenamine

A mixture of 1-(1-methylethyl)-4-(4-nitrophenylpiperazine) (1.7 g, 6.8 mmol) (from Step A above) and 10% palladium-on-charcoal in ethanol (30 mL) was hydrogenated at room temperature and atmospheric pressure overnight. The catalyst was filtered off and the filter cake washed thoroughly with ethanol. The mixture was evaporated under reduced pressure to give 4-[4-(1-methylethyl)-1-piperazinyl]benzenamine (1.6 g, quantitative yield) as a dark brown oil.

C. 1-(4-Isothiocyanatophenyl)-4-(1-methylethyl)piperazine

A solution of 4-[4-(1-methylethyl)-1-piperazinyl]benzenamine (1.6 g, ~6.8 mmol) (from Step B above) in N,N-dimethylformamide (25 mL) was added dropwise over 20 min to a cooled (−15° C.) solution of thiocarbonyldiimidazole (1.4 g, 7.7 mmol) (Aldrich) in N,N-dimethylformamide (30 mL). After the addition was complete, the mixture was stirred at −15° C. for 20 min, then the cooling bath was removed and the solution was stirred for 1 h. Ice-water was added and the mixture was extracted with ether. The ether layer was dried (MgSO4), filtered, and evaporated to give 1-(4-isothiocyanatophenyl)-4-(1-methylethyl)piperazine (1.8 g, quantitative yield).

Example 4

1-(Acetyl)-4-(4-isothiocyanatophenyl)piperazine

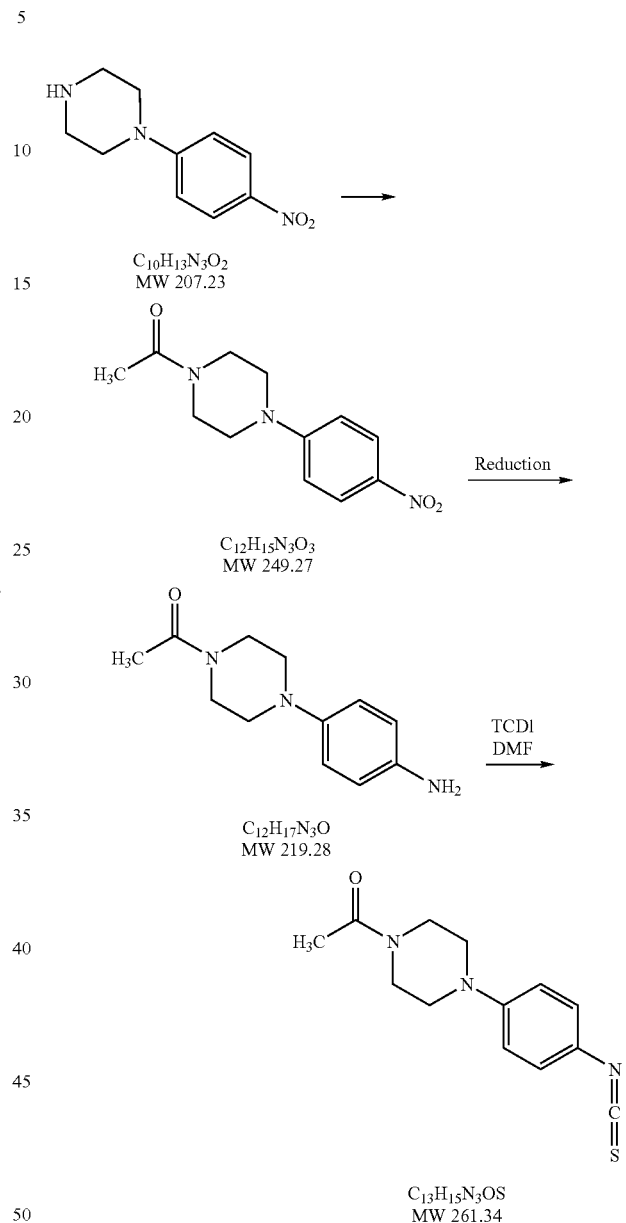

This compound can be prepared by the procedure of Chong, W. K. et al. WO9921845, or as follows:

A. 1-Acetyl-4-(4-nitrophenyl)piperazine

Powdered potassium carbonate (276 mg, 2 mmol) and then acetyl chloride (0.14 mL, 2 mmol) were added to a solution of 1-(4-nitrophenyl) piperazine (2.1 g, 1 mmol) (Acros Organics) in dichloromethane (75 mL). The mixture was stirred at room temperature overnight and then further quantities of powdered potassium carbonate (500 mg, 3.6 mmol) and acetyl chloride (0.2 mL, 2.8 mmol) were added. The mixture was stirred at room temperature overnight, then it was filtered and the filter cake was washed with dichloromethane. The solvent was evaporated from the filtrate, and the residue was chromatographed (0–66% acetone/dichloromethane) to give 1-acetyl-4-(4-nitrophenyl)piperazine (1.8 g, 72%).

B. 1-Acetyl-4-(4-aminophenyl)piperazine

A mixture of 1-acetyl-4-(4-nitrophenyl)piperazine (1.8 g, 7.2 mmol) (from Step A above), and 10% palladium-on-charcoal in ethanol (50 mL) was hydrogenated at room temperature and atmospheric pressure overnight. The catalyst was filtered off and the filter cake washed thoroughly with ethanol. The mixture was evaporated under reduced pressure to give 1-acetyl-4-(4-amino-phenyl)piperazine (1.0 g, 63%) as an off-white solid.

C. 1-(Acetyl)-4-(4-isothiocyanatophenyl)piperazine

A solution of 1-acetyl-4-(4-aminophenyl)piperazine (1.0 g; 4.6 mmol) (from Step B above) in N,N-dimethylformamide (10 mL) was added dropwise to a cooled (−15° C.) solution of thiocarbonyldiimidazole (855 mg, 4.8 mmol) in N,N-dimethylformamide (10 mL). After the addition was complete, the mixture was stirred at −15° C. for 30 min, then the cooling bath was removed and the solution was stirred for 1 h. Ice-water was added and the mixture was extracted with ether (4×50 mL). The combined ether layers were washed with brine, dried (MgSO$_4$), filtered, and evaporated to give 1-(acetyl)-4-(4-isothiocyanatophenyl)piperazine (1.0 g, 84%).

Example 5

4-(2-Hydroxyethyl)-1-(4-isothiocyanatophenyl)piperazine

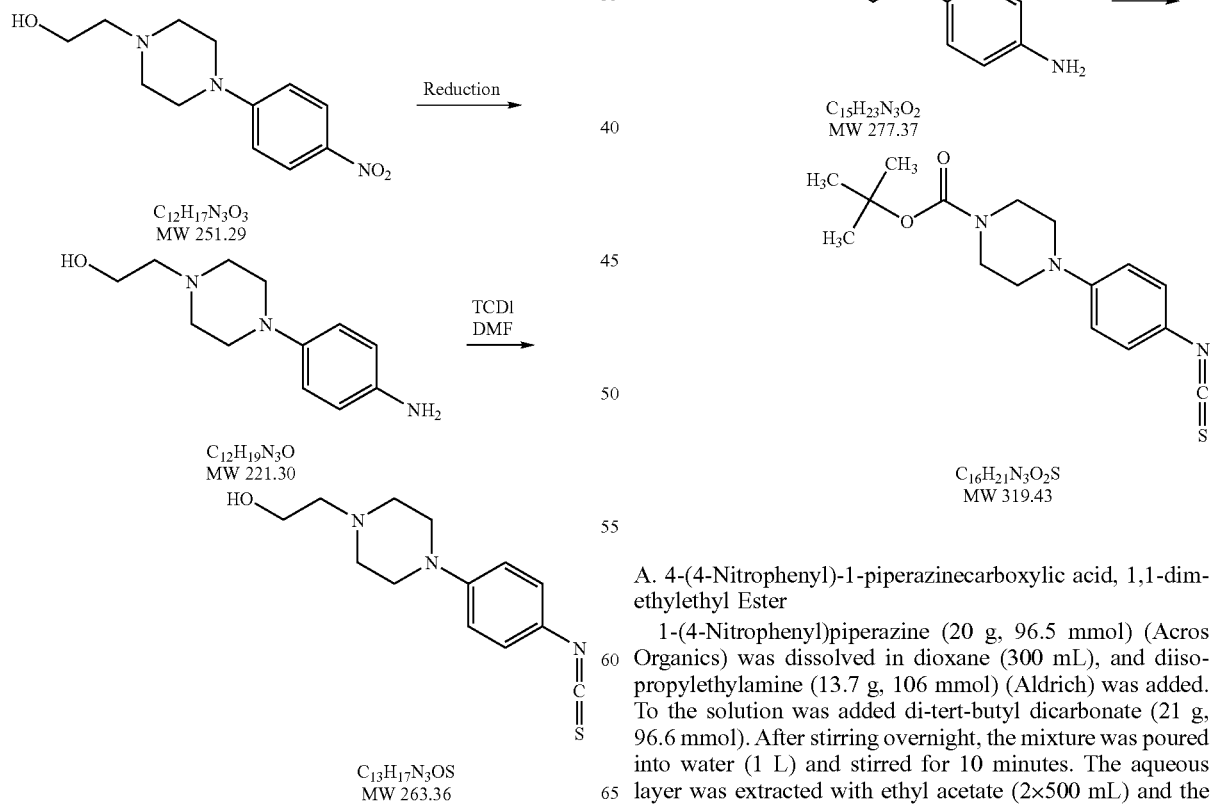

This compound was prepared from 4-(4-nitrophenyl)-1-piperazine-ethanol (Bionet Research Ltd.) using the hydrogenation and isothiocyanate-forming reactions used in Example 4.

Example 6

4-(4-Isothiocyanatophenyl)-1-piperazinecarboxylic acid, 1,1-dimethylethyl Ester

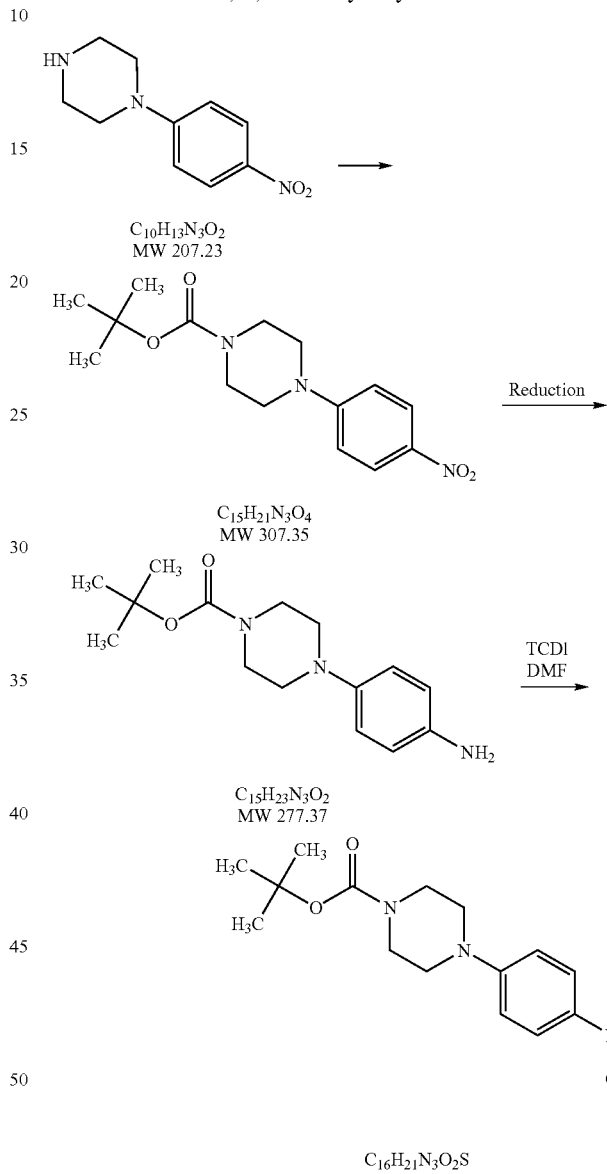

A. 4-(4-Nitrophenyl)-1-piperazinecarboxylic acid, 1,1-dimethylethyl Ester 1-(4-Nitrophenyl)piperazine (20 g, 96.5 mmol) (Acros Organics) was dissolved in dioxane (300 mL), and diisopropylethylamine (13.7 g, 106 mmol) (Aldrich) was added. To the solution was added di-tert-butyl dicarbonate (21 g, 96.6 mmol). After stirring overnight, the mixture was poured into water (1 L) and stirred for 10 minutes. The aqueous layer was extracted with ethyl acetate (2×500 mL) and the combined organic extracts were dried over MgSO$_4$, filtered, and evaporated in vacuo. The residue was recrystalized from a mixture of ethyl acetate/hexane to provide 4-(4-nitrophenyl)-1-piperazinecarboxylic acid, 1,1-dimethylethyl ester (22.7 g, 77%).

B. 4-(4-Aminophenyl)-1-piperazinecarboxylic acid, 1,1-dimethylethyl Ester 4-(4-Nitrophenyl)-1-piperazinecarboxylic acid, 1,1-dimethylethyl ester (20 g, 65 mmol) was dissolved in anhydrous ethanol (250 mL) and 10% Pd/C (1.8 g) was added. The mixture was stirred for 1.5 h under 10 psi of hydrogen and filtered through a Celite pad. The pad was washed with ethyl acetate (3×100 mL) and the combined solution was evaporated in vacuo to yield 4-(4-amino-phenyl)-1-piperazinecarboxylic acid, 1,1-dimethylethyl ester (18 g, 98% yield).

C. 4-(4-Isothiocyanatophenyl)-1-piperazinecarboxylic acid, 1,1-dimethylethyl Ester A solution of 4-(4-aminophenyl)-1-piperazinecarboxylic acid, 1,1-dimethylethyl ester (15 g, 54.1 mmol) (from Step B above) in N,N-dimethyl-formamide (120 mL) was added dropwise to a cooled (−15° C.) solution of 1,1'-thiocarbonyldiimidazole (9.66 g, 54.2 mmol) (Aldrich) in N,N-dimethylformamide (40 mL). After the addition was complete, the cooling bath was removed and the solution was stirred for 1 h. The mixture was poured into ice-water (1 L), stirred for 30 minutes, and extracted with diethyl ether. The combined extracts were dried over $Na_2SO_4$, and evaporated in vacuo to provide 4-(4-isothio-cyanatophenyl)-1-piperazinecarboxylic acid, 1,1-dimethylethyl ester (18 g, 94%).

Example 7

2-Bromo-1-[4-(1-piperidinyl)phenyl]ethanone

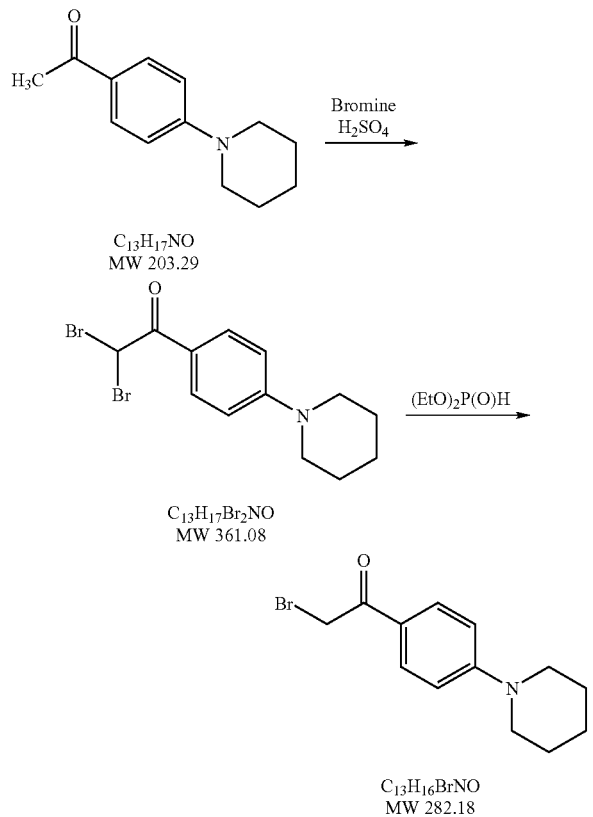

A. 2,2-Dibromo-1-[4-(1-piperidinyl)phenyl]ethanone

Following the procedure of Diwu et al. (Tetrahedron Lett. 1998, 39, 4987–4990), 1-[4-(1-piperidinyl)phenyl]ethanone (5 g, 24.6 mmol) (Aldrich) was dissolved in concentrated sulfuric acid (25 mL) and the resulting solution was cooled to 0° C. To the solution was slowly added bromine (1.3 mL, 25.4 mmol) at 0° C. with stirring. The mixture was gradually warmed to room temperature and stirred for 6 h. The reaction mixture was poured into ice/water. The precipitate was collected by filtration, washed with water and dried in vacuo to provide 2,2-dibromo-1-[4-(1-piperidinyl)phenyl]ethanone (8.2 g, 93%).

B. 2-Bromo-1-[4-(1-piperidinyl)phenyl]ethanone 2,2-Dibromo-1-[4-(1-piperidinyl)phenyl]ethanone (3 g, 8.3 mmol) (from Step A above) was dissolved in tetrahydrofuran (15 mL), and cooled to 0° C. To the resulting solution were added dropwise diethylphosphite (1.13 mL, 8.7 mmol) and triethylamine (1.21 mL, 8.7 mmol) in tetrahydrofuran (7 mL) at 0° C. with stirring. The mixture was slowly warmed to room temperature and stirred for 6 h. The reaction mixture was concentrated in vacuo and poured into ice/water. The precipitate was collected by filtration, washed with water and dried in vacuo to provide 2-bromo-1-[4-(1-piperidinyl)phenyl]ethanone (2.3 g, 100% yield).

Example 8

2-Bromo-1-[4-(4-morpholinyl)phenyl]ethanone

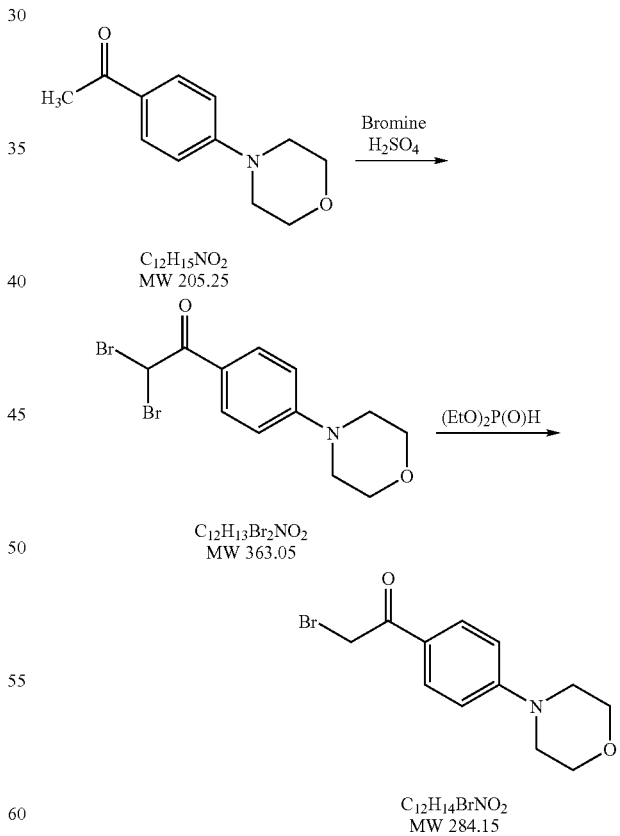

This compound was prepared from 1-[4-(4-morpholinyl)phenyl]ethanone (Aldrich) by procedures analogous to those used to prepare 2-bromo-1-[4-(1-piperidinyl)phenyl]ethanone (Example 7).

Example 9

2-Bromo-1-(3,5-dimethoxyphenyl)ethanone

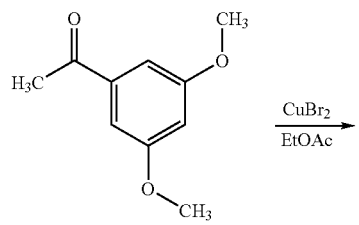

A mixture of 1-(3,5-dimethoxyphenyl)ethanone (3.0 g, 16.6 mmol) (Aldrich) and copper(II) bromide (6.2 g, 27.8 mmol) (Aldrich) in ethyl acetate (35 mL) was heated at reflux under argon for 5 h. Charcoal was added to the mixture which was stirred and then filtered through Celite™. The filter cake was washed with ethyl acetate, and the combined filtrates were evaporated and then purified by elution with dichloromethane (500 mL) through silica gel (150 g) in a filter funnel to give crude 1-(3,5-dimethoxyphenyl)ethanone (4.9 g, quantitative yield). This was used without further purification.

Example 10

N-[4-(Bromoacetyl)phenyl]acetamide

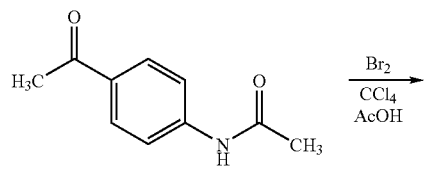

A solution of bromine (0.31 mL, 5.9 mmol) in carbon tetrachloride (10 mL) was added to a suspension of N-(4-acetylphenyl)acetamide (1 g, 5.6 mmol) (Lancaster Synthesis) in carbon tetrachloride (20 mL). The reaction mixture was stirred for several hours but TLC indicated only starting material. Acetic acid (10 mL) was added, and the reaction mixture was stirred overnight. Filtration gave N-[4-(bromoacetyl)phenyl]acetamide (1.4 g) as a solid. HPLC indicated that the purity was approximately 80%. This material was used directly in subsequent steps without purification.

Example 11

1-(1,3-Benzodioxol-5-yl)-2-bromoethanone

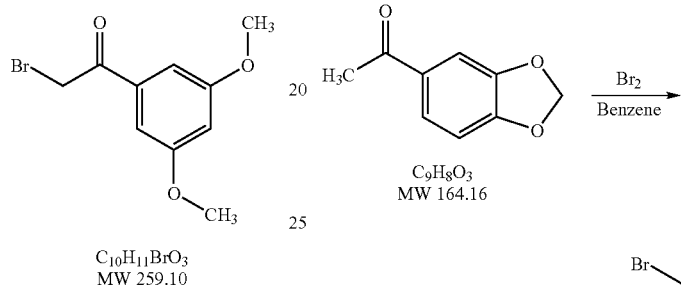

Eight drops of a solution of bromine (1.95 g, 12.2 mmol) in benzene (10 mL) were added to a solution of 1-(1,3-benzodioxol-5-yl)ethanone (2.00 g, 12.2 mmol) (Acros Organics) in benzene (40 mL) in a flask protected from light with aluminum foil. The solution was heated to reflux for ~30 seconds, but it did not decolorize. The rest of the bromine solution was added in ~1 mL aliquots and the solution was then allowed to stand for 2 h. Ethyl acetate (100 mL) was added, and the solution was washed with water and saturated sodium bicarbonate solution (100 mL each), dried (MgSO$_4$), filtered and evaporated to give a black liquid that solidified on standing. NMR indicated that it was a ~1:3 mixture of 1-(1,3-benzodioxol-5-yl)-2,2-dibromoethanone and 1-(1,3-benzodioxol-5-yl)-2-bromoethanone. This material was used directly in subsequent steps without purification.

Example 12

2-Bromo-1-(4-hydroxyphenyl)ethanone

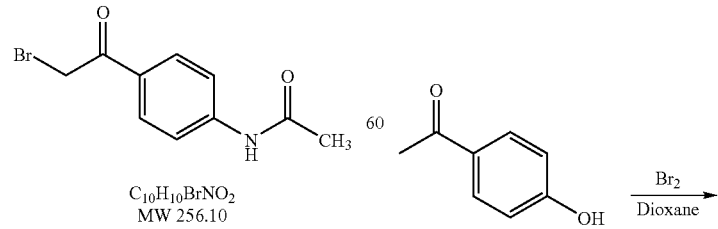

-continued

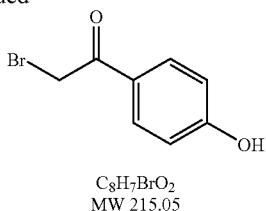

C8H7BrO2
MW 215.05

To a solution of 4-hydroxyacetophenone (2.5 g, 18.3 mmol) (Aldrich) in dioxane (10 mL) was added dropwise a solution of bromine (3.22 g, 20.1 mmol) in dioxane (20 mL). After stirring for 10 minutes, the mixture was concentrated in vacuo and the residue was recrystalized from methanol to provide 2-bromo-1-(4-hydroxyphenyl)ethanone (1.73 g, 44% yield).

Example 13

2-Bromo-1-(3-fluoro-4-methoxyphenyl)ethanone

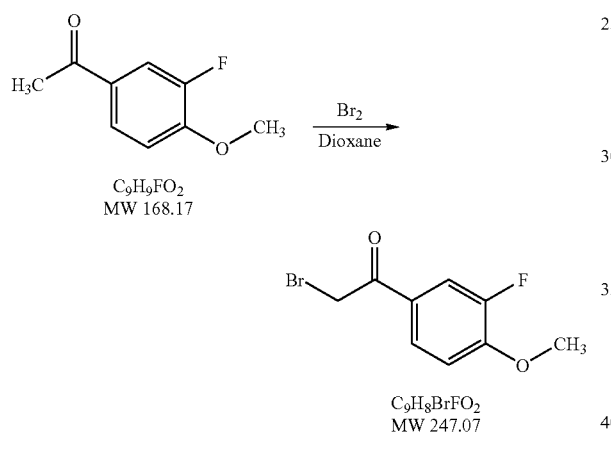

To a solution of 3'-fluoro-4'-methoxyacetophenone (1 g, 5.9 mmol) (Aldrich) in dioxane (10 mL) was added dropwise a solution of bromine (1.13 g, 7.1 mmol) in dioxane (30 mL). After stirring for 10 minutes, the mixture was concentrated in vacuo and the residue was purified by flash chromatography, with 10:4 hexanes/dichloromethane as an eluant, to provide 2-bromo-1-(3-fluoro-4-methoxyphenyl)ethanone as a white powder (910 mg, 63% yield).

Example 14A

2-Bromo-1-(3,5-difluorophenyl)ethanone

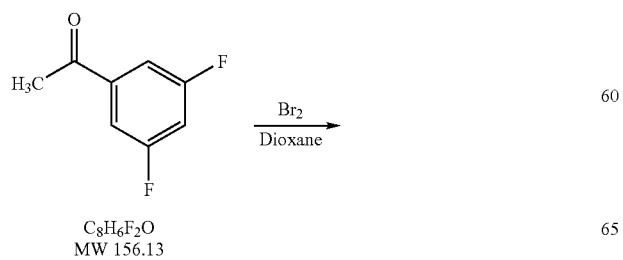

-continued

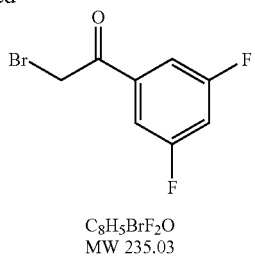

C8H5BrF2O
MW 235.03

To a solution of 3',5'-difluoroacetophenone (3 g, 19.2 mmol) (Lancaster Synthesis) in dioxane (30 mL) was added dropwise a solution of bromine (3.67 g, 23 mmol) in dioxane (75 mL). After stirring for 10 minutes, the mixture was concentrated in vacuo and the residue was purified by flash chromatography, with 10:2 hexanes/dichloromethane as an eluant, to provide 2-bromo-1-(3,5-difluorophenyl)ethanone as a colorless oil (2.9 g, 64% yield).

Example 14B 1-(4-Isothiocyanatophenyl)-4-(2-methoxy-ethyl)piperazin

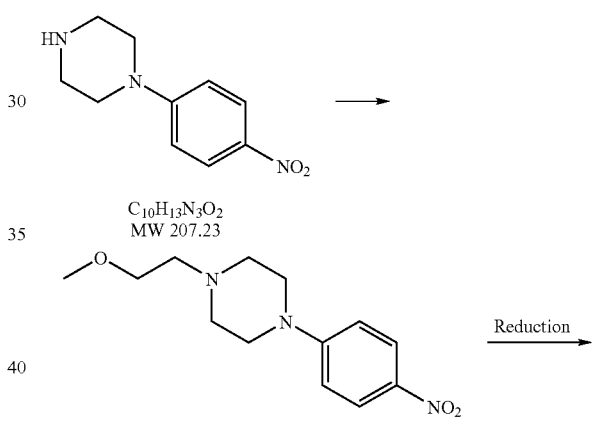

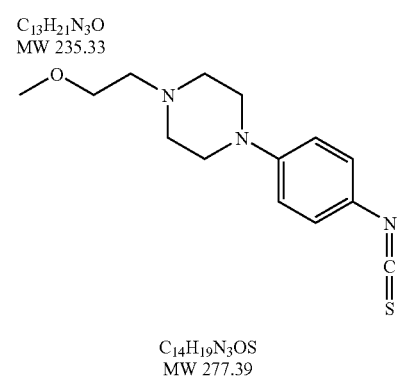

A. 1-(1-[2-methoxy-ethyl])-4-(4-nitrophenyl)piperazine)

A mixture of 4-chloronitrobenene (5.5 g, 34.9 mmol) (Aldrich), and 1-(2-methoxy-ethyl)piperazine 5 g, 34.6 mmol (Chess, GmbH) was heated at 80° C. overnight. Dichloromethane (100 mL) was added and washed with water (3×100 mL). The organic layer was dried (Na2SO4) and concentrated to a dark red oil. Chromatography (4% methanol in dichloromethane) followed by recrystalization from ethyl acetate/hexane gave 1-(1-[2-methoxy-ethyl])-4-(4-nitrophenyl)piperazine) (5.36 g, 58%)

B. 4-[4-(2-methoxy-ethyl)-1-piperazinyl]benzenamine

A mixture of 1-(1-[2-methoxy-ethyl])-4-(4-nitrophenyl) piperazine) (5.36 g, 20.2 mmol) (from Step A above) and 10% palladium-on-charcoal in ethanol (125 mL) was hydrogenated at room temperature at 20 psi for one hour. The catalyst was filtered off and the filter cake washed thoroughly with ethanol. The mixture was evaporated under reduced-pressure to give 4-[4-(2-methoxy-ethyl)-1-piperazinyl]benzenamine (4 g, 84%)

C. 1-(4-Isothiocyanatophenyl)-4-(1-[2-methoxy-ethyl])piperazine

A solution of 4-[4-(1-{2-methoxy-ethyl])-1-piperazinyl] benzenamine (4 g, 17 mmol) (from Step B above) in N,N-dimethylformamide (60 mL) was added dropwise over 20 min to a cooled (−15° C.) solution of thiocarbonyldiimidazole (3 g, 17.03 mmol) (Aldrich) in N,N-dimethylformamide (15 mL). After the addition was complete, the mixture was stirred at −15° C. for 20 min, then the cooling bath was removed and the solution was stirred for 1 h. Ice-water (800 ml) was added and the mixture was stirred for 30 min. The solid was filtered off and washed with water and dried under vacuum to give 1-(4-isothiocyanatophenyl)-4-(1-[2-methoxy-ethyl])piperazine (2.8 g, 67%).

Example 14C

1-(4-Isothiocyanatophenyl)-4-(1-methylpropyl)piperazine

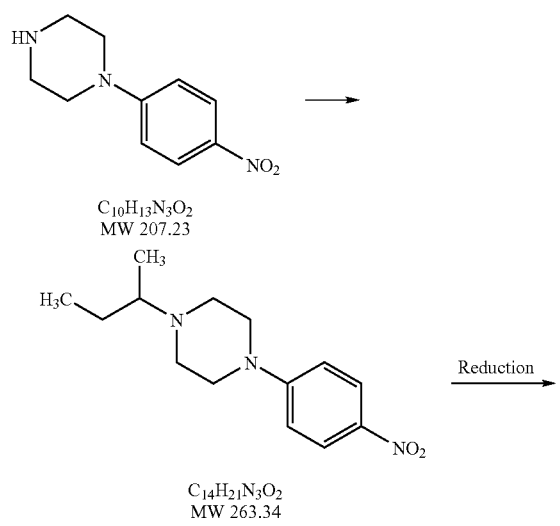

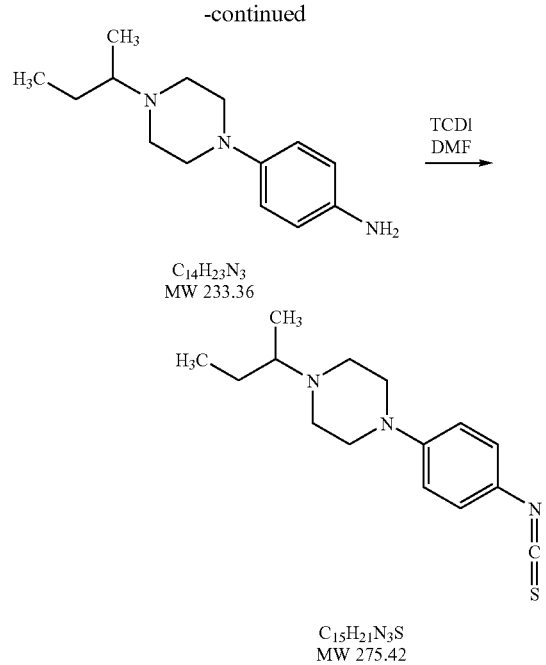

A. 1-(sec-butyl)-4-(4-nitrophenyl)piperazine)

A mixture of 1-(4-nitrophenyl)piperazine (6, 28.98 mmol) (Acros Organics), powdered potassium carbonate (2.7 g, 30.4 mmol), 2-Bromobutane (3.32 ml, 30.4 mmol), and a catalytic amount of 18-crown-6 in acetonitrile (45 mL) was heated at reflux overnight. The mixture was filtered, and the filter cake was washed with acetonitrile. The solvent was evaporated from the combined filtrates and the residue was partitioned between water and ethyl acetate. The layers were separated and the aqueous layer was extracted twice with ethyl acetate. The combined organic layers were dried (Na2SO4), filtered, evaporated and chromatographed (2.5% methanol in dichloromethane) to give 1-(sec-butyl)-4-(4-nitrophenylpiperazine) (4.45 g, 58%).

B. 4-[4-(sec-butyl)-1-piperazinyl]benzenamine

A mixture of 1-(sec-butyl)-4-(4-nitrophenylpiperazine) (4.45 g, 16.9 mmol) (from Step A above) and 10% palladium-on-charcoal in ethanol (125 mL) was hydrogenated at room temperature at 20 psi for 1.25 hour. The catalyst was filtered off and the filter cake washed thoroughly with ethanol. The mixture was evaporated under reduced pressure to give 4-[4-(sec-butyl)-1-piperazinyl]benzenamine (3.55 g g, 90%)

C. 1-(4-Isothiocyanatophenyl)-4-(sec-butyl)piperazine

A solution of 4-[4-(sec-butyl)-1-piperazinyl]benzenamine (3.5 g, 15 mmol) (from Step B above) in N,N-dimethylformamide (40 mL) was added dropwise over 20 min to a cooled (−15° C.) solution of thiocarbonyldiimidazole (2.68 g, 15.03 mmol) (Aldrich) in N,N-dimethylformamide (15 mL). After the addition was complete, the mixture was stirred at −15° C. for 20 min, then the cooling bath was removed and the solution was stirred for 1 h. Ice-water (800 ml) was added and the mixture was stirred for 30 min. The solid was filtered off and washed with water and dried under vacuum to give 1-(4-isothiocyanatophenyl)-4-(sec-butyl) piperazine (3.6 g, 87%) as a purple solid.

Example 14D

4-Cyclopentyl-1-(4-isothiocyanatophenyl)piperazine

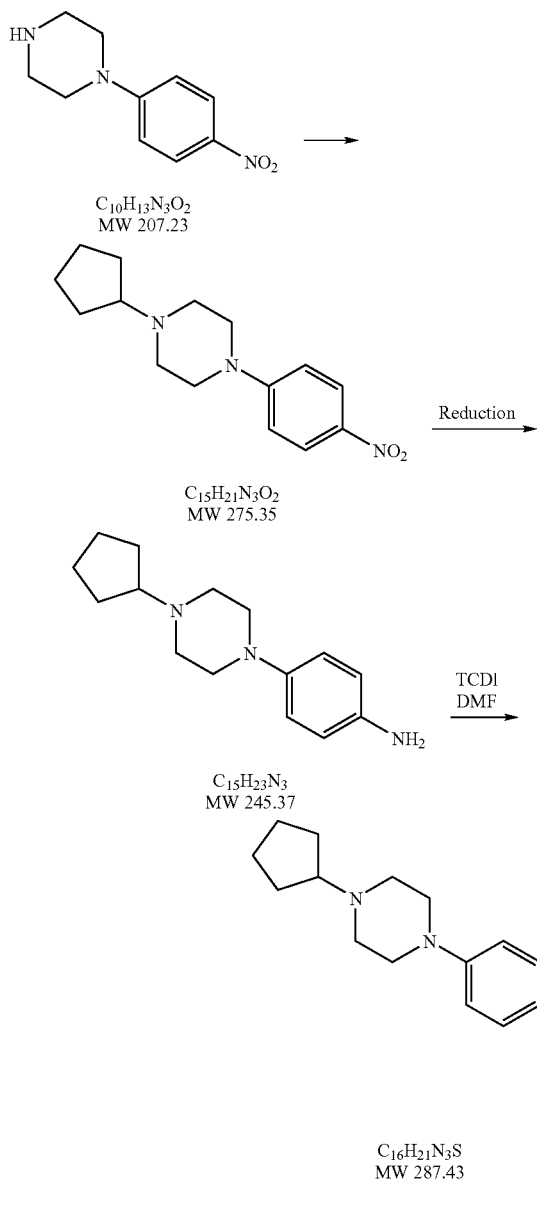

A. 1-Cyclopentyl-4-(4-nitrophenyl)piperazine)

A mixture of 1-(4-nitrophenyl)piperazine (12 g, 57.9 mmol) (Acros Organics), powdered potassium carbonate (5.4 g, 39 mmol), iodocyclopentane (7 mL, 60.8 mmol) (Aldrich) and a catalytic amount of 18-crown-6 in acetonitrile (90 mL) was heated at reflux overnight. The mixture was filtered, and the filter cake was washed with acetonitrile. The solvent was evaporated from the combined filtrates and the residue was partitioned between water and ethyl acetate. The layers were separated and the aqueous layer was extracted twice with ethyl acetate. The combined organic layers were dried (Na2SO4), filtered, evaporated to a yellow solid and dried under vacuum to give 1-cyclopentyl-4-(4-nitrophenyl)piperazine) (6.6 g, 41%)

B. 4-(4-Cyclopentyl-1-piperazinyl)benzenamine

A mixture of 1-cyclopentyl-4-(4-nitrophenylpiperazine) (6.6 g, 23.9 mmol) (from Step A above) and 10% palladium-on-charcoal in ethanol (175 mL) was hydrogenated at room temperature at 20 psi for 1.25 hr. The catalyst was filtered off and the filter cake washed thoroughly with ethanol. The mixture was evaporated under reduced pressure to give 4-(4-cyclopentyl-1-piperazinyl)benzenamine (5.7 g, 97%)

C. 4-Cyclopentyl-1-(4-isothiocyanatophenyl)piperazine

A solution of 4-[4-(1-cyclopentyl)-1-piperazinyl]benzenamine (5.7 g, 22.4 mmol) (from Step B above) in N,N-dimethylformamide (75 mL) was added dropwise over 20 min to a cooled (−15° C.) solution of thiocarbonyldiimidazole (4 g, 22.5 mmol) (Aldrich) in N,N-dimethylformamide (40 mL). After the addition was complete, the mixture was stirred at −15° C. for 20 min, then the cooling bath was removed and the solution was stirred for 1 hr. then poured into ice-water (1500 mL), stirred for 30 min. then the precipitate filtered and washed with water and dried under vacuum to give 4-cyclopentyl-1-(4-isothiocyanatophenyl)piperazine (6 g, 93%)

Example 14E

1-(4-Isothiocyanatophenyl)-4-(2-methylpropyl)piperazine

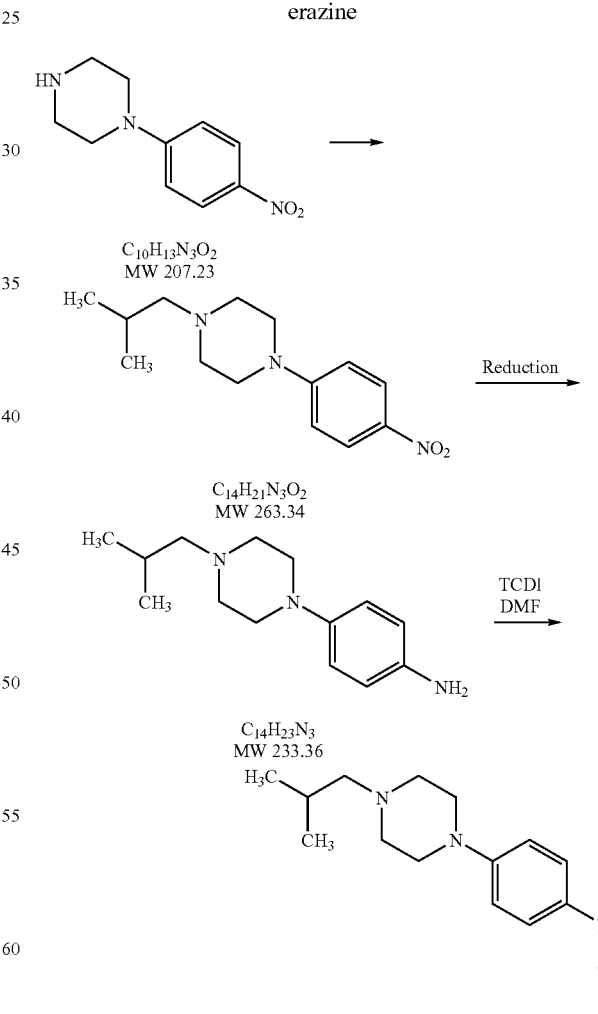

A. 1-(isobutyl)-4-(4-nitrophenyl)piperazine)

A mixture of 1-(4-nitrophenyl)piperazine (8 g, 38.6 mmol) (Acros Organics), powdered potassium carbonate (3.58 g, 25.98 mmol), 1-Iodo-2-methylpropane (4.66 ml, 40.5 mmol), and a catalytic amount of 18-crown-6 in acetonitrile (60 mL) was heated at reflux overnight. The mixture was filtered, and the filter cake was washed with acetonitrile. The solvent was evaporated from the combined filtrates and the residue was partitioned between water and ethyl acetate. The layers were separated and the aqueous layer was extracted twice with ethyl acetate. The combined organic layers were dried (Na2SO4), filtered, evaporated and dried under vacuum to give 1-(isobutyl)-4-(4-nitrophenyl)piperazine) (9.4 g, 92%) as a yellow solid.

B. 4-[4-(isobutyl)-1-piperazinyl]benzenamine

A mixture of 1-(isobutyl)-4-(4-nitrophenylpiperazine) (9.4 g, 35.7 mmol) (from Step A above) and 10% palladium-on-charcoal in ethanol (175 mL) was hydrogenated at room temperature at 20 psi for 1.25 hour. The catalyst was filtered off and the filter cake washed thoroughly with ethanol. The mixture was evaporated under reduced pressure to give 4-[4-(isobutyl)-1-piperazinyl]benzenamine (7.8 g, 94%) as a dark red solid.

C. 1-(4-Isothiocyanatophenyl)-4-(1-isobutyl)piperazine

A solution of 4-[4-(isobutyl)-1-piperazinyl]benzenamine (7.8 g, 33.4 mmol) (from Step B above) in N,N-dimethylformamide (75 mL) was added dropwise over 20 min to a cooled (−15° C.) solution of thiocarbonyldiimidazole (5.97 g, 33.5 mmol) (Aldrich) in N,N-dimethylformamide (25 mL). After the addition was complete, the mixture was stirred at −15° C. for 20 min, the cooling bath was removed and the solution was stirred for 1 h. Ice-water (700 ml) was added and the mixture was stirred for 30 min. The solid was filtered off and washed with water and dried under vacuum to give 1-(4-Isothiocyanatophenyl)-4-(1-isobutyl)piperazine (8 g, 87%)

Example 14F 4-(3-Hydroxypropyl)-1-(4-isothiocyanatophenyl)piperazine

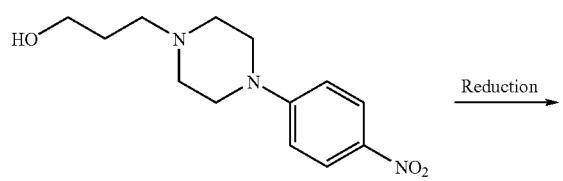

C$_{13}$H$_{19}$N$_3$O$_3$
MW 265.31

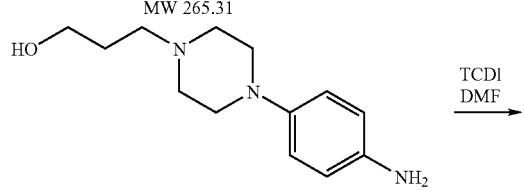

C$_{13}$H$_{21}$N$_3$O
MW 235.33

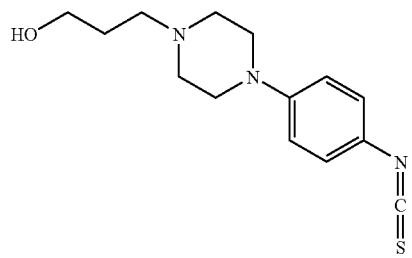

C$_{14}$H$_{19}$N$_3$OS
MW 277.39

This compound was prepared from 4-(4-nitrophenyl)-1-piperazine-propanol (which can be prepared according to the procedure of Loewe and Mieth *Arzneim.-Forsch.* 1966; 16, 1306–1310) using the hydrogenation and isothiocyanate-forming reactions used in Example 4. MS (ES) MH$^+$=277.

Example 14G

4-Cyclopropylmethyl-1-(4-isothiocyanatophenyl)piperazine

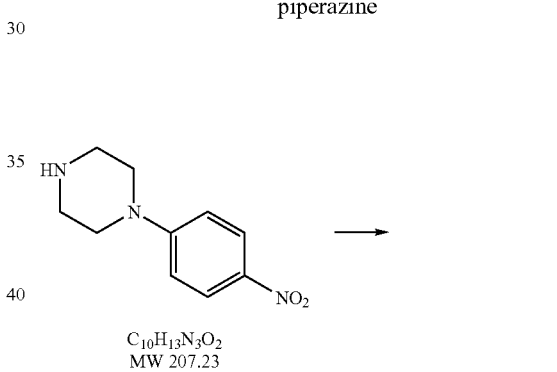

C$_{10}$H$_{13}$N$_3$O$_2$
MW 207.23

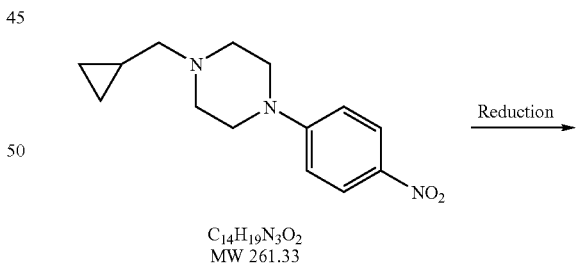

C$_{14}$H$_{19}$N$_3$O$_2$
MW 261.33

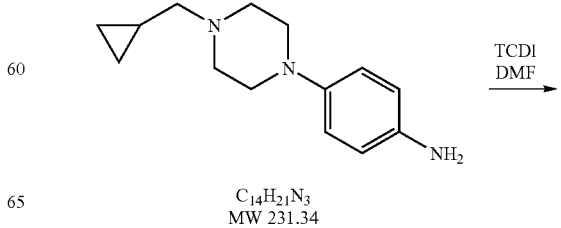

C$_{14}$H$_{21}$N$_3$
MW 231.34

-continued

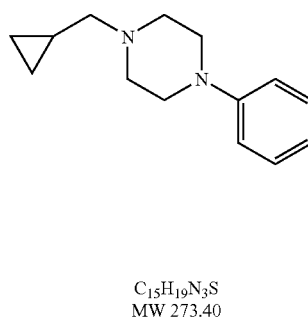

C₁₅H₁₉N₃S
MW 273.40

A. 1-(Cyclopropylmethyl)-4-(4-nitrophenyl)piperazine)

A mixture of 1-(4-nitrophenyl)piperazine (10 g, 48.3 mmol) (Acros Organics), powdered potassium carbonate (4.5 g, 32.6 mmol), Cyclopropylmethyl bromide (4.93 ml, 50.7 mmol), and a catalytic amount of 18-crown-6 in acetonitrile (75 mL) was heated at reflux overnight. The mixture was filtered, and the filter cake was washed with acetonitrile. The solvent was evaporated from the combined filtrates and the residue was partitioned between water and ethyl acetate. The layers were separated and the aqueous layer was extracted twice with ethyl acetate. The combined organic layers were washed with brine, dried (Na2SO4), filtered, evaporated and chromatographed (4% methanol in dichloromethane) to give 1-(cyclopropylmethyl)-4-(4-nitrophenylpiperazine) (4.27 g, 0.34%).

B. 4-[4-(Cyclopropylmethyl)-1-piperazinyl]benzenamine

A mixture of 1-(cyclopropylmethyl)-4-(4-nitrophenylpiperazine) (4.27 g, 16.3 mmol) (from Step A above) and 10% palladium-on-charcoal in ethanol (125 mL) was hydrogenated at room temperature at 20 psi for one hour. The catalyst was filtered off and the filter cake washed thoroughly with ethanol. The mixture was evaporated under reduced pressure to give 4-[4-(cyclopropylmethyl)-1-piperazinyl]benzenamine (3.7 g g, 98%) as a dark red solid.

C. 1-(4-Isothiocyanatophenyl)-4-(1-cyclopropylmethyl)piperazine

A solution of 4-[4-(cyclopropylmethyl)-1-piperazinyl] benzenamine (3.7 g, 16 mmol) (from Step B above) in N,N-dimethylformamide (50 mL) was added dropwise over 20 min to a cooled (−15° C.) solution of thiocarbonyldiimidazole (2.87 g, 16.1 mmol) (Aldrich) in N,N-dimethylformamide (25 mL). After the addition was complete, the mixture was stirred at −15° C. for 20 min, then the cooling bath was removed and the solution was stirred for 1 h. Ice-water (1000 mL) was added and the mixture was stirred for 30 min. The solid was filtered off and washed with water and dried under vacuum. (4 g, 91%).

Example 14H

2-Bromo-1-(3,4,5-trifluoro-phenyl)ethanone

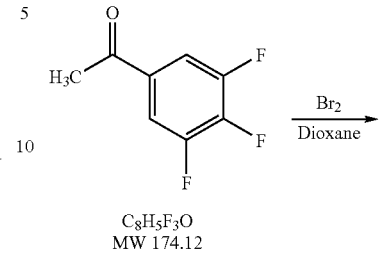

C₈H₅F₃O
MW 174.12

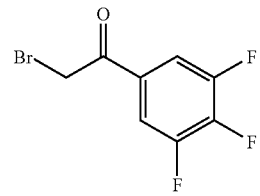

C₈H₄BrF₃O
MW 253.02

This compound was prepared from 1-(3,4,5-trifluoro-phenyl)ethanone (ABCR GmbH & Co. KG) following the procedure used in Example 13.

Example 14I

2-Bromo-1-(4-fluoro-3-methoxy-phenyl)ethanon

C₉H₉FO₂
MW 168.17

C₉H₈BrFO₂
MW 247.07

This compound was prepared from 1-(4-fluoro-3-methoxy-phenyl)ethanone (Apin Chemicals Ltd.) following the procedure used in Example 13.

Example 14J

2-Bromo-1-(3-trifluoromethoxy-phenyl)ethanone

C₉H₇F₃O₂
MW 204.15

-continued

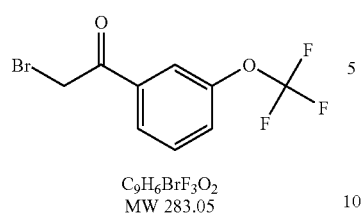

C₉H₆BrF₃O₂
MW 283.05

This compound was prepared from 1-(3-trifluoromethoxy-phenyl)ethanone (Aldrich) following the procedure used in Example 13.

Example 14K

2-Bromo-1-(3,5-difluoro-4-methoxy-phenyl)ethanone

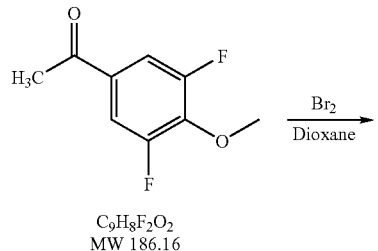

C₉H₈F₂O₂
MW 186.16

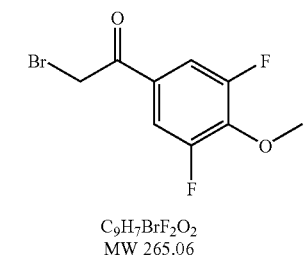

C₉H₇BrF₂O₂
MW 265.06

This compound was prepared from 1-(3,5-difluoro-4-methoxy-phenyl)ethanone (ABCR GmbH & Co. KG) following the procedure used in Example 13.

Example 14L

2-Bromo-1-(3-difluoromethoxy-phenyl)ethanone

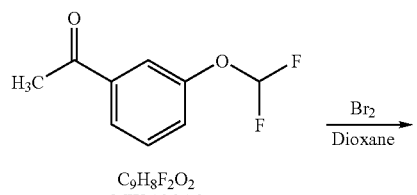

C₉H₈F₂O₂
MW 186.16

-continued

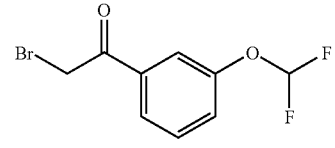

C₉H₇BrF₂O₂
MW 265.06

This compound was prepared from 1-(3-difluoromethoxy-phenyl)ethanone (ABCR GmbH & Co. KG) following the procedure used in Example 13.

Example 14M

2-Bromo-1-(4-hydroxy-3-fluoro-phenyl)ethanon

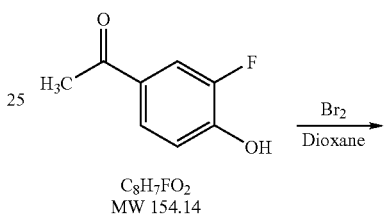

C₈H₇FO₂
MW 154.14

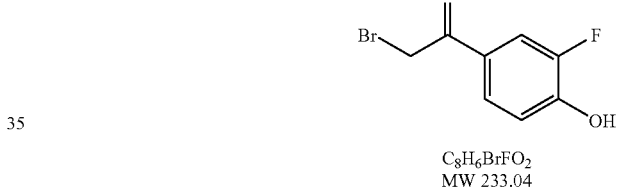

C₈H₆BrFO₂
MW 233.04

This compound was prepared from 1-(4-hydroxy-3-fluoro-phenyl)ethanone (Apin Chemicals Ltd.) following the procedure used in Example 13.

Example 14N

2-Bromo-1-(3-hydroxy-phenyl)ethanone

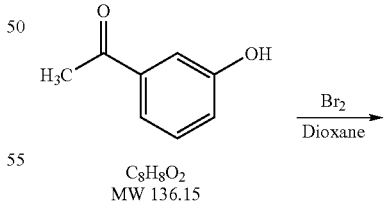

C₈H₈O₂
MW 136.15

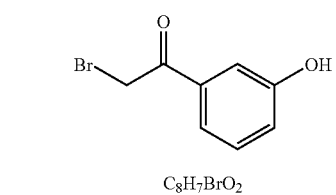

C₈H₇BrO₂
MW 215.05

This compound was prepared from 1-(3-hydroxy-phenyl)ethanone (Aldrich) following the procedure used in Example 13.

Example 14O

2-Bromo-1-(3-ethylphenyl)ethanone

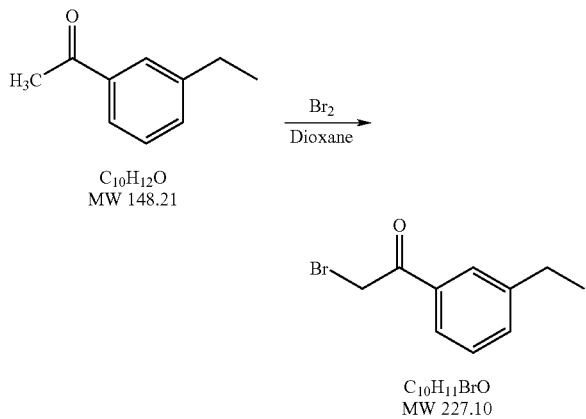

To a stirred solution of 3-ethylacetophenone (Maybridge Chemical Company Ltd.; 1.103 g, 7.44 mmol) in dry 1,4-dioxane (15 mL) was added, bromine (383 µL, 7.44 mmol). The solution was stirred at room temperature for 30 min. and then the solvent was removed on a rotary evaporator. The residue was chromatographed on a Foxy 200 machine (Isco, Inc., P.O. Box 82531, Lincoln, Nebr. 68501, USA.; eluent, 5% $CH_2Cl_2$/Hexane, 0–2 min. then 20–30% $CH_2Cl_2$/Hexane, 2–20 min.) to give 2-bromo-1-(3-ethylphenyl)ethanone (1.15 g, 68%) as a clear oil.

Example 15

[4-Amino-2-[[4-(4-methyl-1-piperazinyl)phenyl]amino]-5-thiazolyl](4-chloro-3-nitrophenyl)methanone

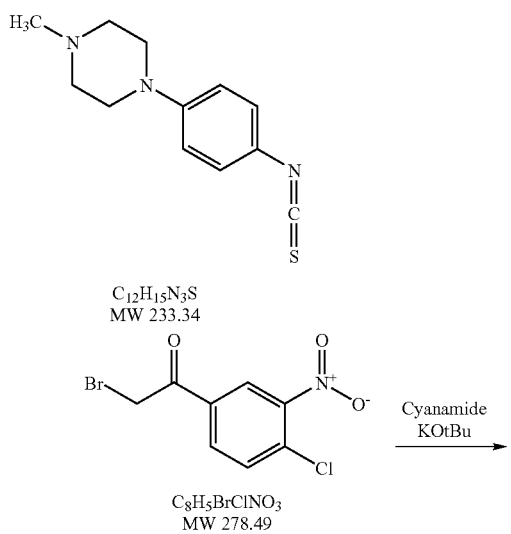

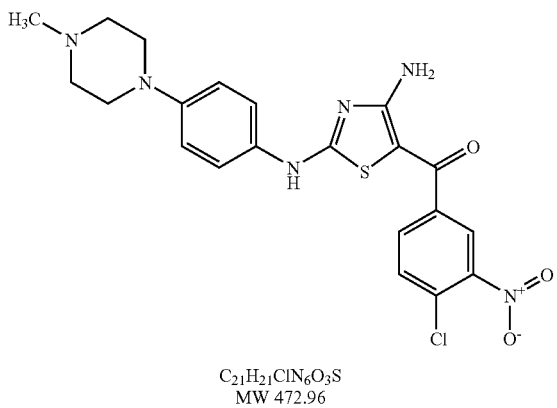

To a mixture of 1-(4-isothiocyanatophenyl)-4-methylpiperazine (of Example 1; 1.0 g, 4.3 mmol) and cyanamide (0.2 g, 4.8 mmol) in acetonitrile (43 mL), a solution of potassium tert-butoxide (43 mL, 0.1 M in tert-BuOH) was added. After 30 minutes at room temperature, 2-bromo-1-(4-chloro-3-nitro-phenyl)ethanone (1.2 g, 4.3 mmol) (Maybridge Chemical Company Ltd.) was added. The reaction mixture was stirred for 4 h and then poured into 50 mL of water. The product was collected by filtration, washed with water and diethyl ether. The yellow powder was dried in vacuo to provide 0.9 g (45% yield) of [4-amino-2-[[4-(4-methyl-1-piperazinyl)phenyl]amino]-5-thiazolyl](4-chloro-3-nitrophenyl)methanone.

Example 16

Resin-Bound Thiouronium Salt

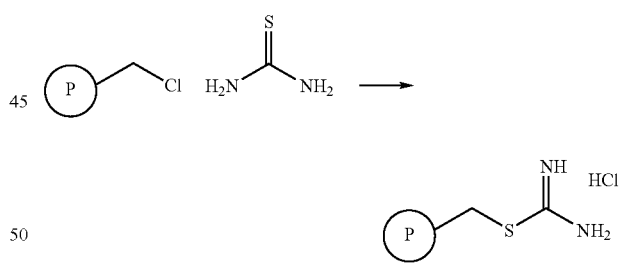

Following the procedure of Obrecht et al. (Helv. Chim. Acta. 1997, 80, 65–72), a mixture of Merrifield resin (77 g, 331 mmol: Cl load of 4.3 mmol/g) (Fluka) and thiourea (126 g, 1650 mmol) in dioxane/ethanol (4/1) (750 mL) was heated at 85° C. for 5 days. The reaction mixture was filtered and the resin was successively washed with hot ethanol (2×500 mL), ethanol (500 mL), dioxane (2×500 mL), hexanes (2×500 mL) and diethyl ether (2×500 mL). The pale yellow resin-was dried in vacuo to afford 1–15 g of the title resin. The loading of the resin was determined by nitrogen and sulfur analysis: N (7.78), S (9.77).

Example 17

Resin-Bound Thiourea: General Procedure

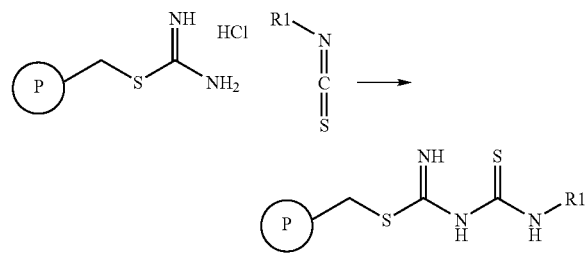

A mixture of resin-bound thiouronium salt (of Example 16; 1 g, 2.8 mmol, loading capacity: 2.8 mmol/g), isothiocyanate ($R^1NCS$, 5.6 mmol), N,N-diisopropylethylamine (5.6 mmol) (Aldrich), and resin-bound N,N-diisopropylethylamine (5.6 mmol, loading capacity: 3.59 mmol/g from Argonaut, Inc.) in N,N-dimethylformamide (12 mL) was gently shaken overnight. The resin was filtered and washed successively with N,N-dimethylformamide, THF, MeOH, $CH_2Cl_2$, and diethyl ether. The resin was dried at 40° C./high vacuum overnight to provide resin-bound thiourea.

The following resin-bound thioureas were prepared from the indicated isothiocyanates using the general procedure described in Example 17.

| Starting Material: Isothiocyanate ($R^1NCS$) | Product: Resin-bound thiourea |
|---|---|
| 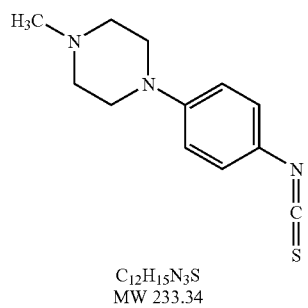<br>$C_{12}H_{15}N_3S$<br>MW 233.34<br>Example 1 | 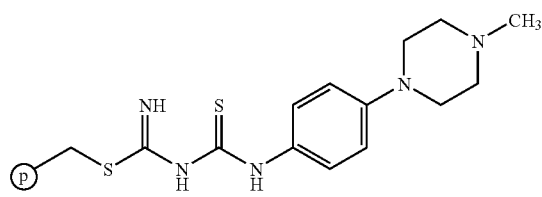<br>Example 18 |
| 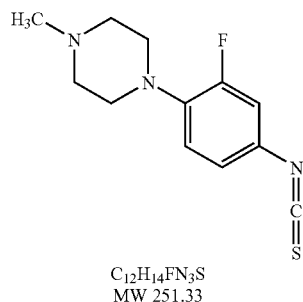<br>$C_{12}H_{14}FN_3S$<br>MW 251.33<br>Example 2 | 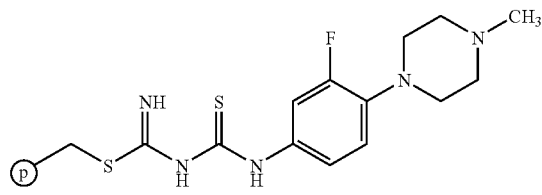<br>Example 19 |
| 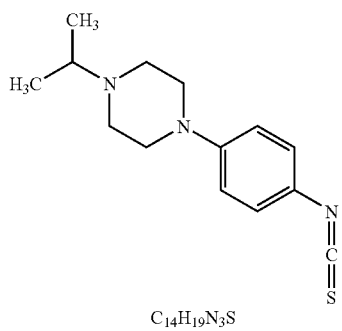<br>$C_{14}H_{19}N_3S$<br>MW 261.39<br>Example 3 | 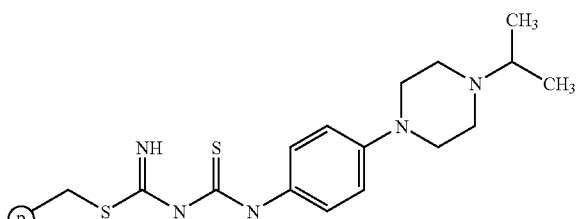<br>Example 20 |

-continued
| Starting Material: Isothiocyanate (R¹NCS) | Product: Resin-bound thiourea |
|---|---|
| 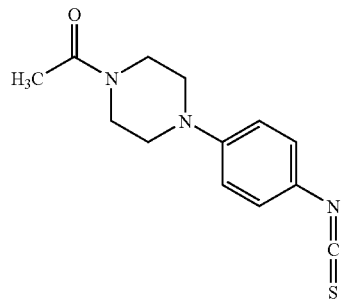<br>$C_{13}H_{15}N_3OS$<br>MW 261.35<br>Example 4 | 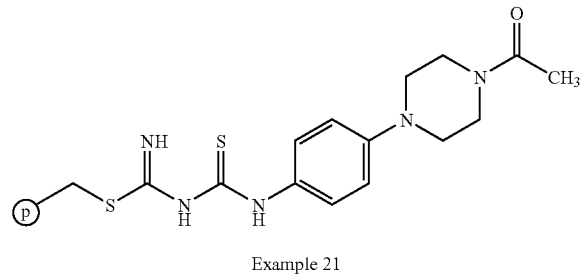<br>Example 21 |
| 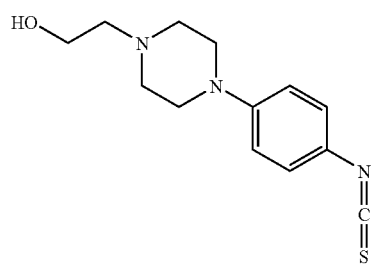<br>$C_{13}H_{17}N_3OS$<br>MW 263.36<br>Example 5 | 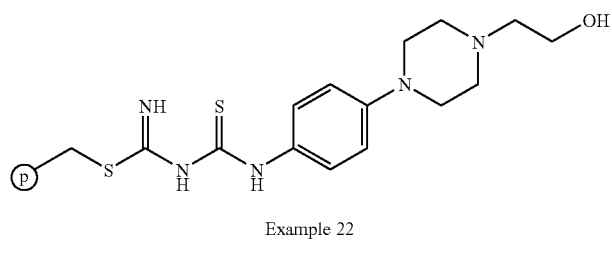<br>Example 22 |
| 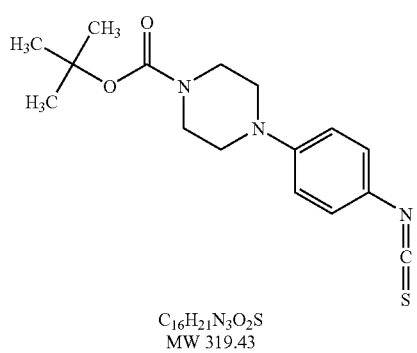<br>$C_{16}H_{21}N_3O_2S$<br>MW 319.43<br>Example 6 | 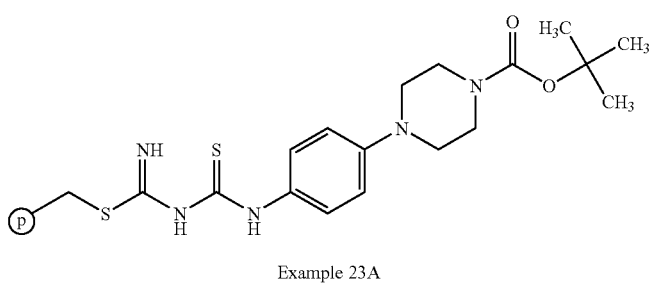<br>Example 23A |
| 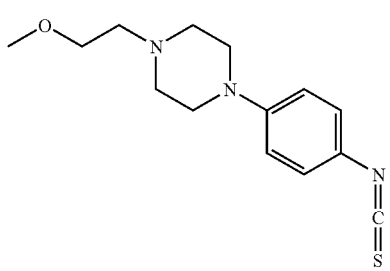<br>$C_{14}H_{19}N_3OS$<br>MW 277.39<br>Example 14B | 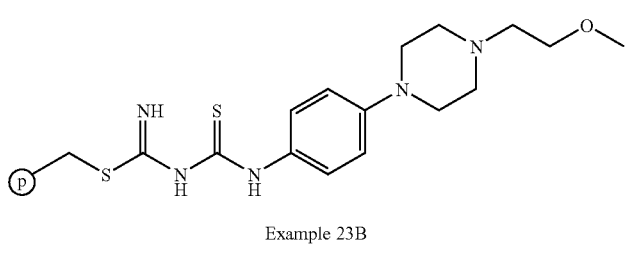<br>Example 23B |

-continued
| Starting Material: Isothiocyanate ($R^1NCS$) | Product: Resin-bound thiourea |
|---|---|
| 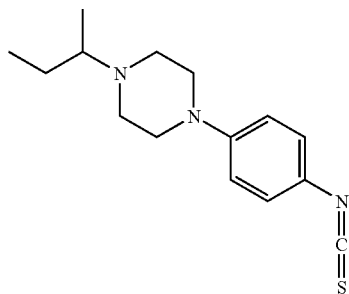<br>$C_{15}H_{21}N_3S$<br>MW 275.42<br>Example 14C | 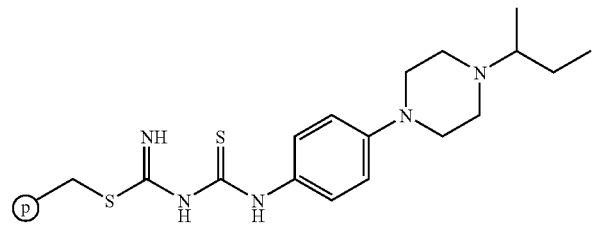<br>Example 23C |
| 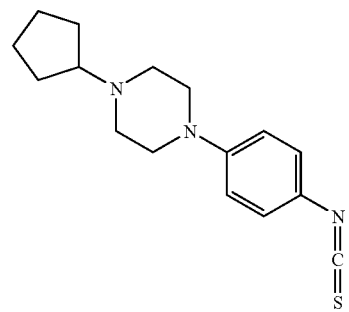<br>$C_{16}H_{21}N_3S$<br>MW 287.43<br>Example 14D | 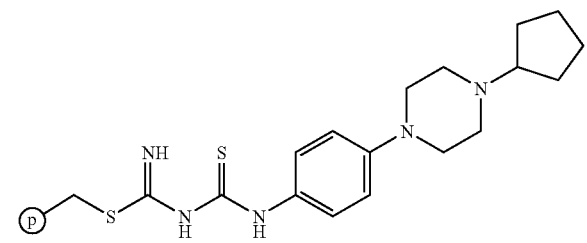<br>Example 23D |
| 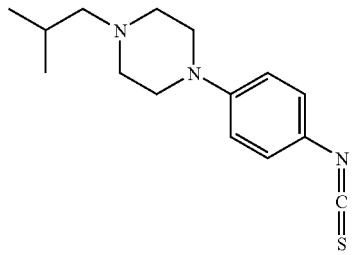<br>$C_{15}H_{21}N_3S$<br>MW 275.42<br>Example 14E | 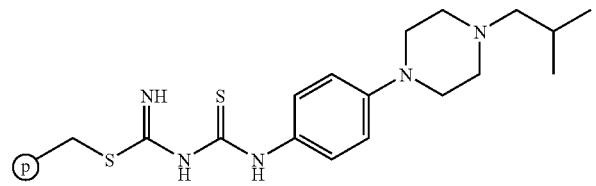<br>Example 23E |
| 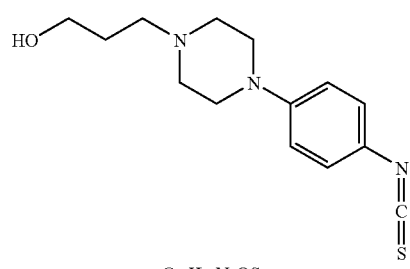<br>$C_{14}H_{19}N_3OS$<br>MW 277.39<br>Example 14F | 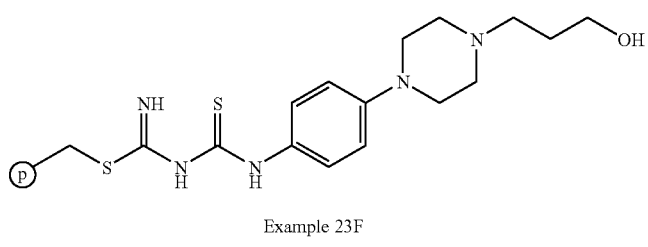<br>Example 23F |

Example 24

[4-Amino-2-[[4-(4-methyl-1-piperazinyl)phenyl]amino]-5-thiazolyl](2,3-dihydro-1,4-benzodioxin-6-yl)methanone

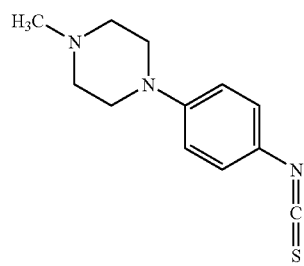

C₁₂H₁₅N₃S
MW 233.34

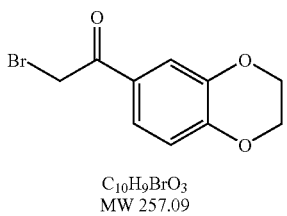

C₁₀H₉BrO₃
MW 257.09

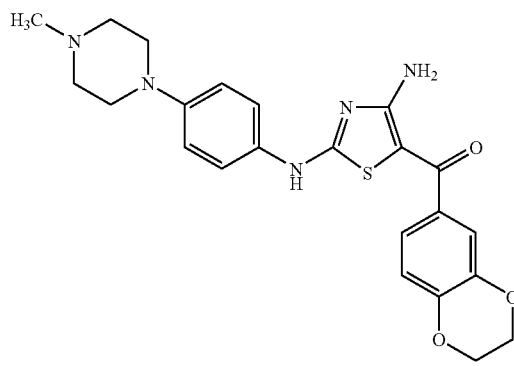

C₂₃H₂₅N₅O₃S
MW 451.44 tert-Butanol (4 mL) and then 1-(4-isothiocyanatophenyl)-4-methyl piperazine (of Example 1; 219 mg, 1 mmol) were added to a solution of cyanamide (44 mg, 1.05 mmol) (Aldrich) in acetonitrile (5 mL). Potassium t-butoxide (1 M in tert-butanol; 1 mL, 1 mmol) was added and the solution was stirred for 30 min. 2-Bromo-1-(2,3-dihydro-1,4-benzodioxin-6-yl)ethanone (257 mg, 1 mmol) (Maybridge Chemical Company Ltd.) was added, and the solution was stirred at room temperature for 3 days. The yellow solid was filtered off and washed with cold acetonitrile and then ether to give [4-amino-2-[[4-(4-methyl-1-piperazinyl)phenyl]amino]-5-thiazolyl](2,3-dihydro-1,4-benzodioxin-6-yl)methanone (280 mg, 66%).

Example 25

[4-Amino-2-[[4-(4-methyl-1-piperazinyl)phenyl]amino]-5-thiazolyl](1,3-benzodioxol-5-yl)methanone

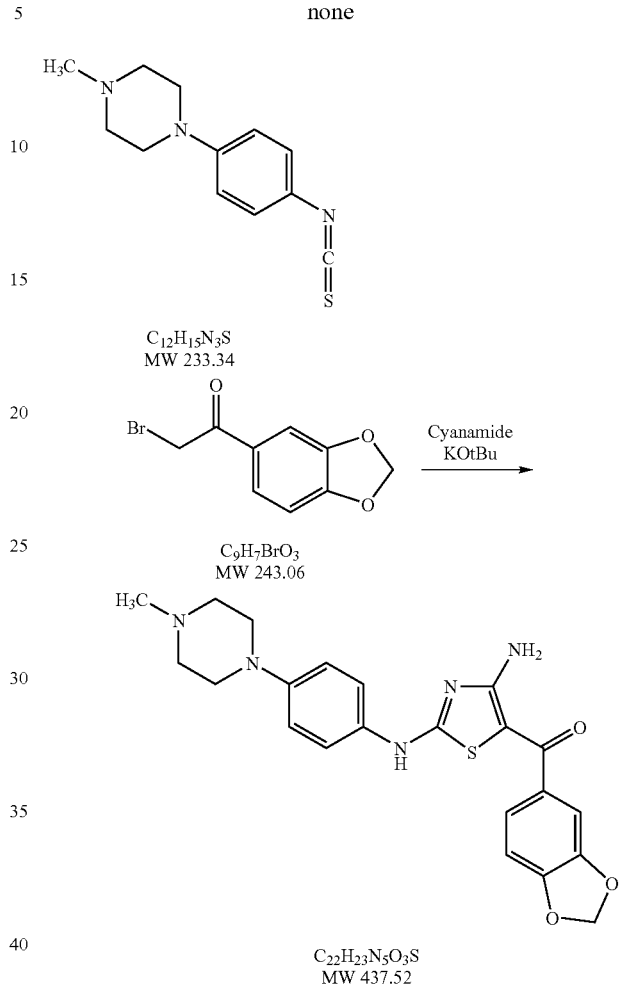

This compound was prepared in 75% yield from cyanamide (Aldrich), 1-(4-isothiocyanatophenyl)-4-methylpiperazine (of Example 1), and 1-(1,3-benzodioxol-5-yl)-2-bromoethanone (of Example 11) following the procedure used to in Example 24.

Example 26

[4-Amino-2-[[4-(4-methyl-1-piperazinyl)phenyl]amino]-5-thiazolyl][4-(1-pyrrolidinyl)phenyl]methanone

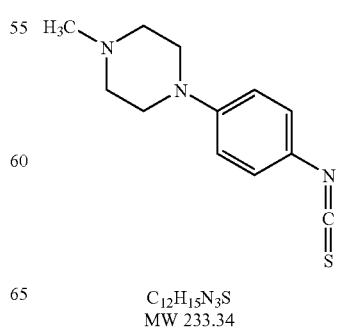

C₁₂H₁₅N₃S
MW 233.34

63

-continued

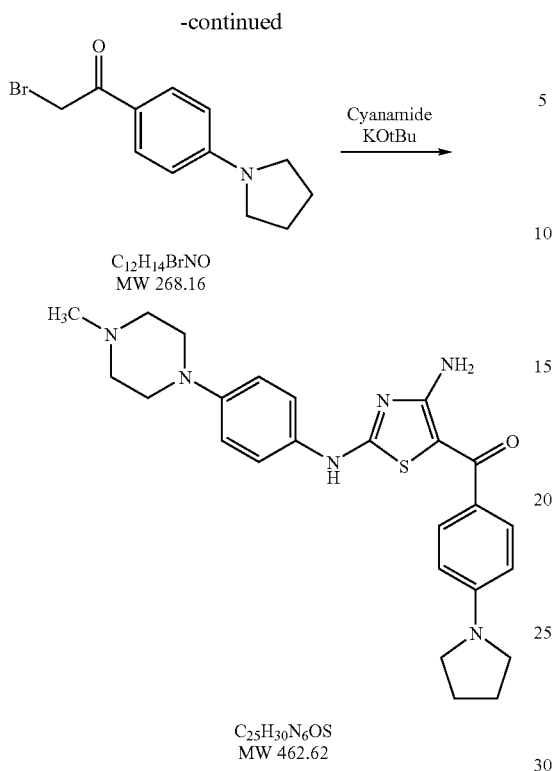

tert-Butanol (4 mL) and then 1-(4-isothiocyanatophenyl)-4-methyl piperazine (of Example 1; 219 mg, 1 mmol) were added to a solution of cyanamide (44 mg, 1.05 mmol) in acetonitrile (5 mL). Potassium t-butoxide (1 M in tert-butanol; 1 mL, 1 mmol) was added and the solution was stirred for 30 min. 2-Bromo-1-[4-(1-pyrrolidinyl)phenyl] ethanone (257 mg, 1 mmol) (Lancaster) was added, and the solution was stirred at room temperature for 2 days. The yellow-brown solid was filtered off and washed with cold acetonitrile, water and then cold acetonitrile (weight of solid: 271 mg). A portion of this crude product (50 mg) was purified by chromatography (10% methanol/dichloromethane) to give [4-amino-2-[[4-(4-methyl-1-piperazinyl)phenyl]amino]-5-thiazolyl][4-(1-pyrrolidinyl)phenyl] methanone (18.5 mg).

Example 27

[4-Amino-2-[[4-(4-methyl-1-piperazinyl)phenyl] amino]-5-thiazolyl][4-(1-piperidinyl)phenyl]methanone

64

-continued

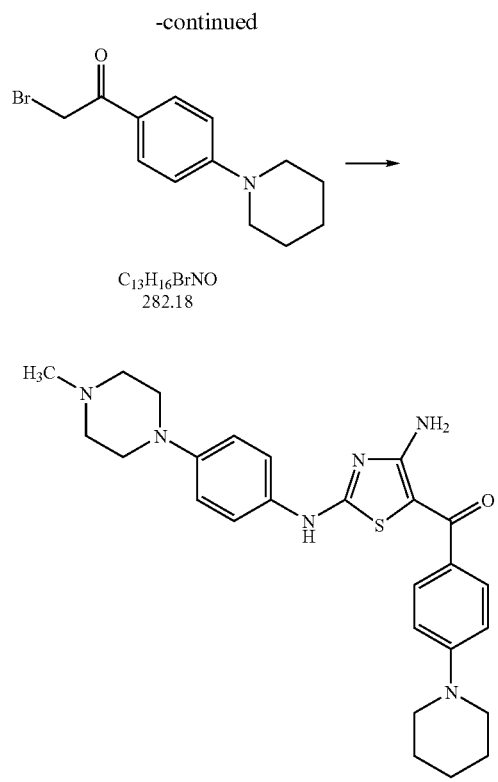

A mixture of the resin-bound thiourea of Example 18 (57 mg, 0.1 mmol, loading capacity: 1.76 mmol/g) and 2-bromo-1-[4-(1-piperidinyl)phenyl]ethanone (of Example 7; 56 mg, 0.2 mmol) in N,N-dimethylformamide (1.5 mL) was shaken overnight. The reaction suspension was filtered and the resin was washed with N,N-dimethylformamide and dichloromethane. The solvent was evaporated in vacuo and the residue was triturated by diethyl ether/hexanes (1/9) to yield [4-amino-2-[[4-(4-methyl-1-piperazinyl)phenyl]amino]-5-thiazolyl][4-(1-piperidinyl) phenyl]methanone. Mass spectrum (ES) $MH^+=477$ Example 28

[4-Amino-2-[[4-(4-methyl-1-piperazinyl)phenyl] amino]-5-thiazolyl][4-(4-morpholinyl)phenyl]methanone, Acetate Salt

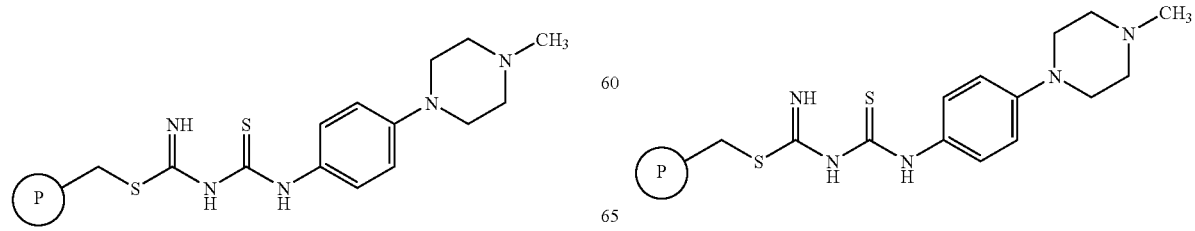

-continued

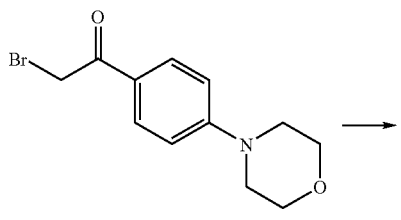

C₁₂H₁₄BrNO₂
MW 284.15

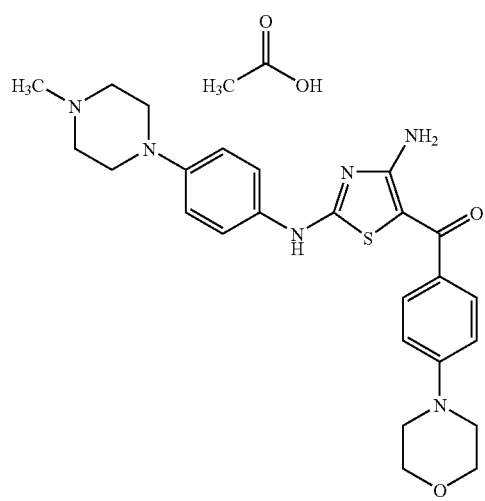

C₂₅H₃₀N₆O₂S/C₂H₄O₂
MW 478.62/60.05

This compound was prepared from the resin-bound thiourea of Example 18 and 2-bromo-1-[4-(4-morpholinyl)phenyl]ethanone (of Example 8) by the procedure used in Example 27. The crude product was purified by HPLC using an Amicon $C_{18}$ 2×5 cm column with the following gradient: A (20 mM NH₄OAc/H₂O), B (20 mM NH₄OAc/CH₃CN), A to B gradient (10 to 75% over 10 minutes), flow rate: 20 mL/min. Mass spectrum (ES) MH$^+$=479

Example 29

[4-Amino-2-[[4-(4-methyl-1-piperazinyl)phenyl]amino]-5-thiazolyl](3,4-dihydro-2H-1,5-benzodioxepin-7-yl)methanone

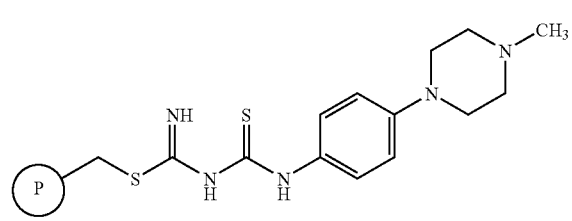

-continued

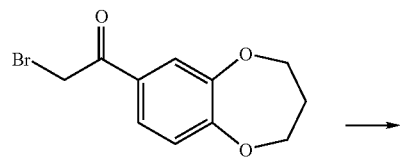

C₁₁H₁₁BrO₃
MW 271.11

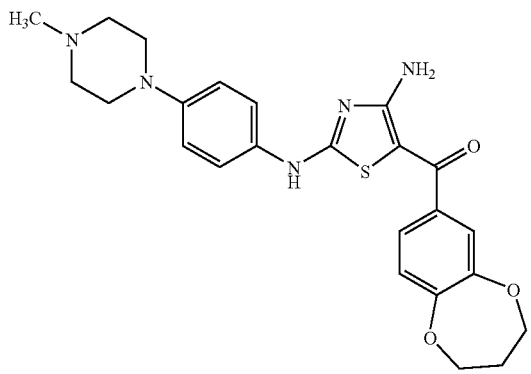

C₂₄H₂₇N₅O₃S
MW 465.58

This compound was prepared from the resin-bound thiourea of Example 18 and 2-bromo-1-(3,4-dihydro-2H-1,5-benzodioxepin-7-yl)ethanone (Maybridge Chemical Company Ltd.) by the procedure used in Example 27. Mass spectrum (ES) MH+=466.

Example 30

[4-Amino-2-[[4-(4-methyl-1-piperazinyl)phenyl]amino]-5-thiazolyl]-(4-hydroxyphenyl)methanone

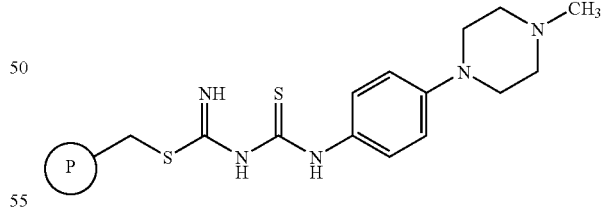

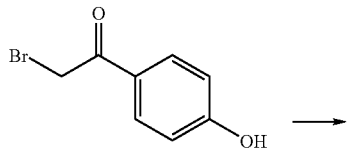

C₈H₇BrO₂
MW 215.05

-continued

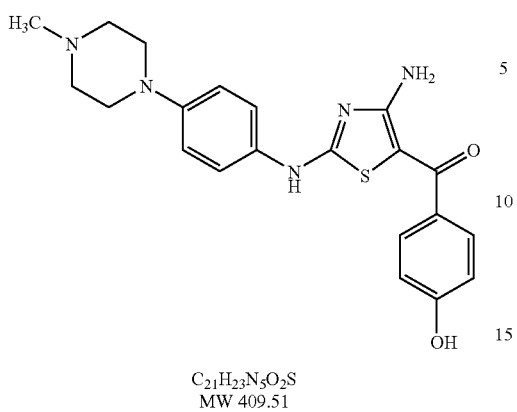

C₂₁H₂₃N₅O₂S
MW 409.51

This compound was prepared from the resin-bound thiourea of Example 18 and 2-bromo-1-(4-hydroxyphenyl)ethanone (of Example 12) by the procedure used in Example 27. Mass spectrum (ES) MH⁺=410

Example 31

[4-Amino-2-[[4-(4-methyl-1-piperazinyl)phenyl]amino]-5-thiazolyl](3-nitrophenyl)methanone

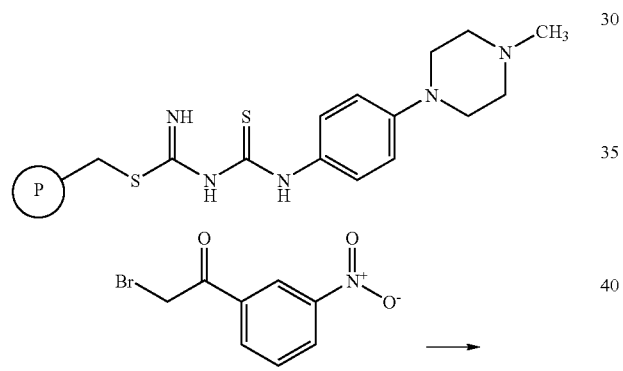

C₈H₆BrNO₃
MW 244.05

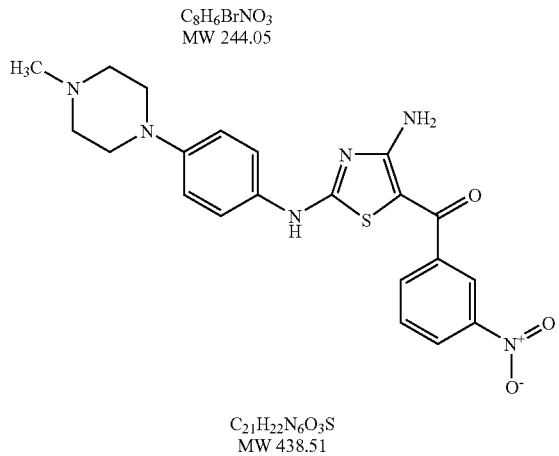

C₂₁H₂₂N₆O₃S
MW 438.51

This compound was prepared from the resin-bound thiourea of Example 18 and 2-bromo-1-(3-nitrophenyl)ethanone (Aldrich) by the procedure used in Example 27. Mass spectrum (ES) MH⁺=439.

Example 32

[4-Amino-2-[[4-(4-methyl-1-piperazinyl)phenyl]amino]-5-thiazolyl](4-methoxyphenyl)methanone

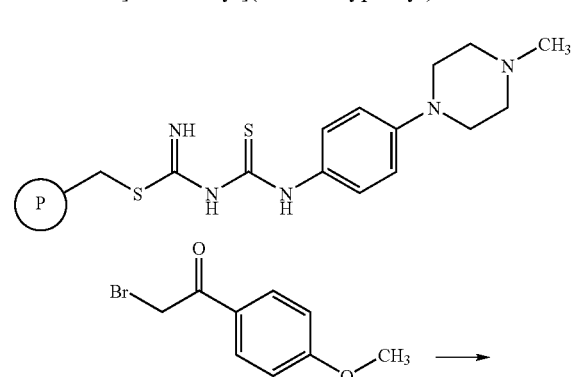

C₉H₉BrO₂
MW 229.07

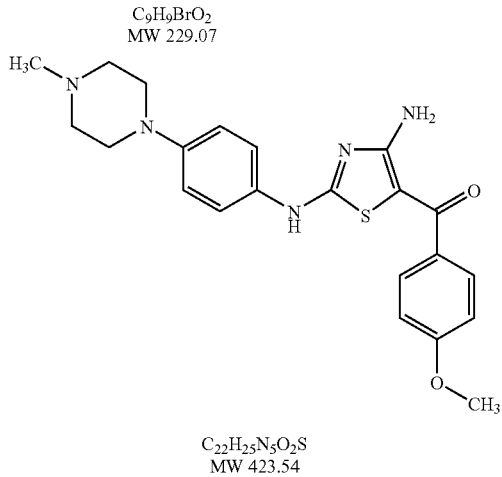

C₂₂H₂₅N₅O₂S
MW 423.54

This compound was prepared from the resin-bound thiourea of Example 18 and 2-bromo-1-(4-methoxyphenyl)ethanone (Aldrich) by the procedure used in Example 27. Mass spectrum (ES) MH⁺=424.

Example 33

[4-Amino-2-[[4-(4-methyl-1-piperazinyl)phenyl]amino]-5-thiazolyl][4-(diethylamino)phenyl]methanone

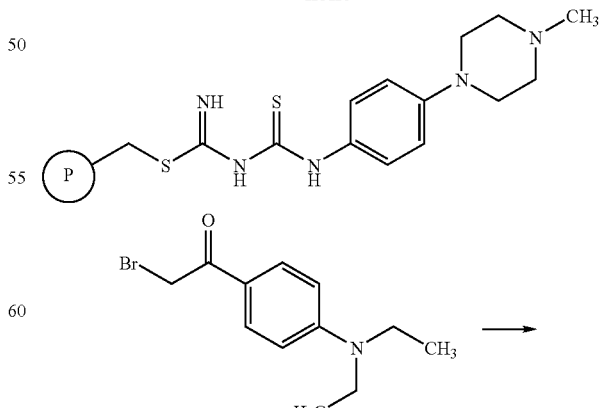

C₁₂H₁₆BrNO
MW 270.17

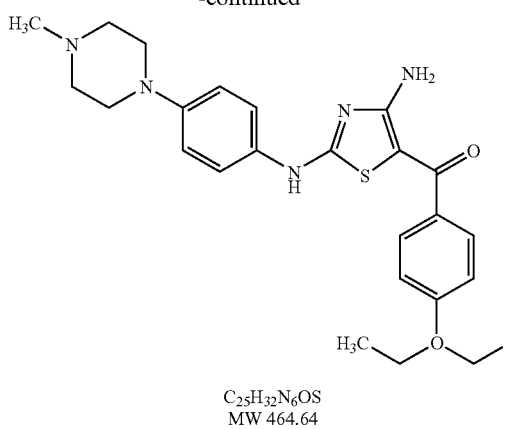

C₂₅H₃₂N₆OS
MW 464.64

This compound was prepared from the resin-bound thiourea of Example 18 and 2-bromo-1-[4-(diethylamino)phenyl]ethanone (Lancaster Synthesis) by the procedure used in Example 27. Mass spectrum (ES) MH⁺=465.

Example 34

[4-Amino-2-[[4-(4-methyl-1-piperazinyl)phenyl]amino]-5-thiazolyl](2-dibenzofuranyl)methanone

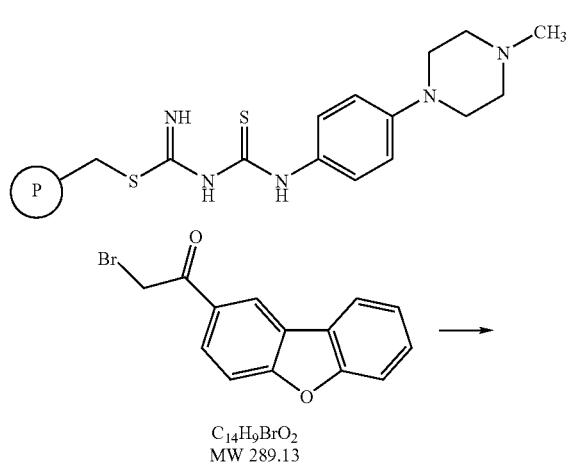

C₁₄H₉BrO₂
MW 289.13

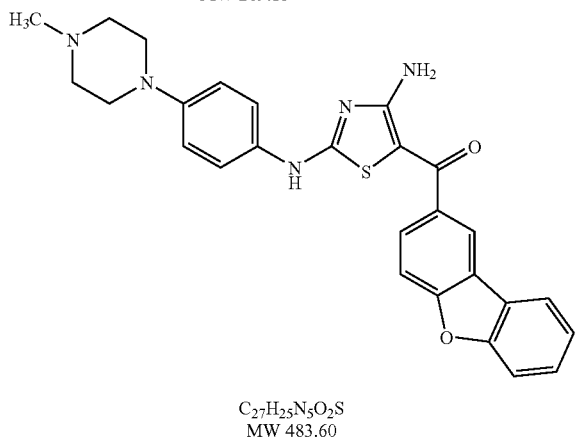

C₂₇H₂₅N₅O₂S
MW 483.60

This compound was prepared from the resin-bound thiourea of Example 18 and 2-bromo-1-(2-dibenzofuranyl)ethanone (Salor), by the procedure used in Example 27. Mass spectrum (ES) MH⁺=484.

Example 35

[4-Amino-2-[[4-(4-methyl-1-piperazinyl)phenyl]amino]-5-thiazolyl](3-fluoro-4-methoxyphenyl)methanone

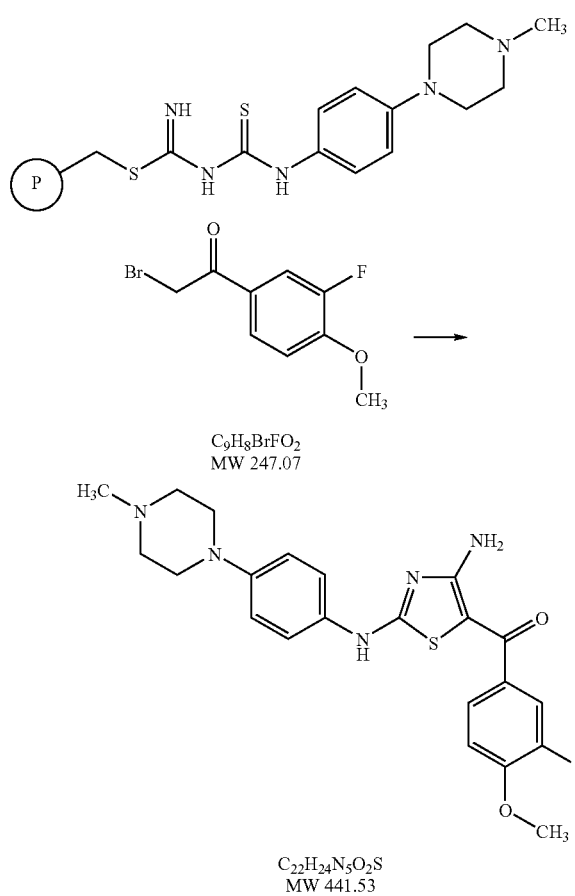

C₉H₈BrFO₂
MW 247.07

C₂₂H₂₄N₅O₂S
MW 441.53

This compound was prepared from the resin-bound thiourea of Example 18 and 2-bromo-1-(3-fluoro-4-methoxyphenyl)ethanone (of Example 13) by the procedure used in Example 27. Mass spectrum (ES) MH⁺=442.

Example 36

[4-Amino-2-[[4-(4-methyl-1-piperazinyl)phenyl]amino]-5-thiazolyl](3-methoxyphenyl)methanone

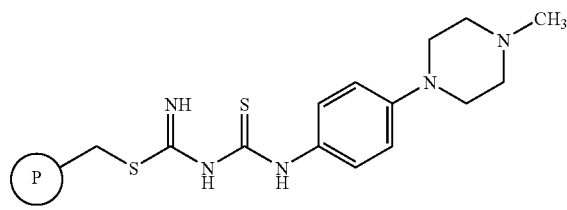

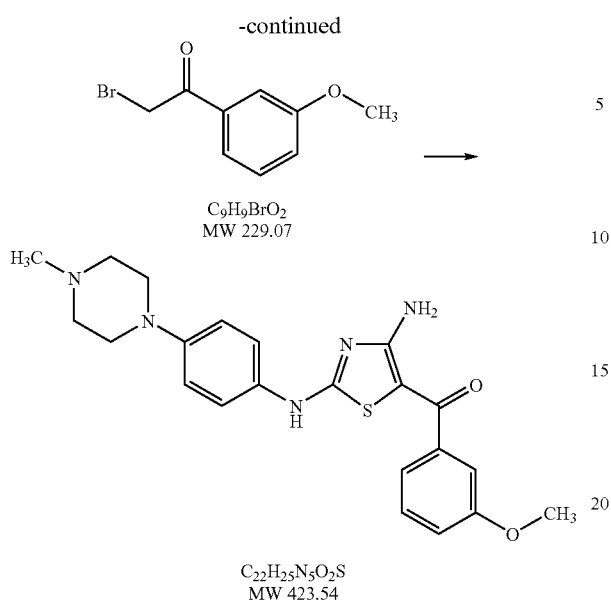

This compound was prepared from the resin-bound thiourea of Example 18 and 2-bromo-1-(3-methoxyphenyl)ethanone (Aldrich) by the procedure used in Example 27. Mass spectrum (ES) MH+=424.

Example 37

[4-Amino-2-[[4-(4-methyl-1-piperazinyl)phenyl]amino]-5-thiazolyl](3,4-dichlorophenyl)methanone

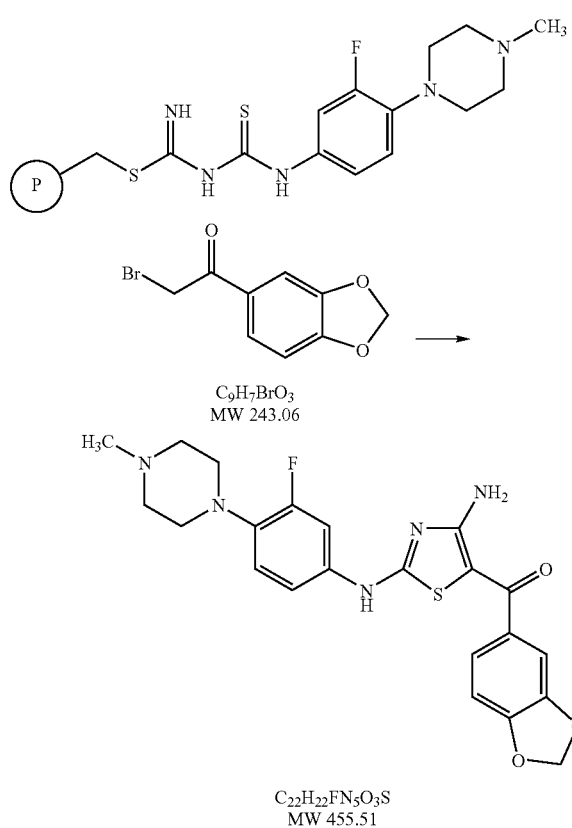

This compound was prepared from the resin-bound thiourea of Example 18 and 2-bromo-1-(3,4-dichlorophenyl)ethanone (Lancaster Synthesis) by the procedure used in Example 27. Mass spectrum (ES) MH+=462.

Example 38

[4-Amino-2-[[3-fluoro-4-(4-methyl-1-piperazinyl)phenyl]amino]-5-thiazolyl](1,3-benzodioxol-5-yl)methanone

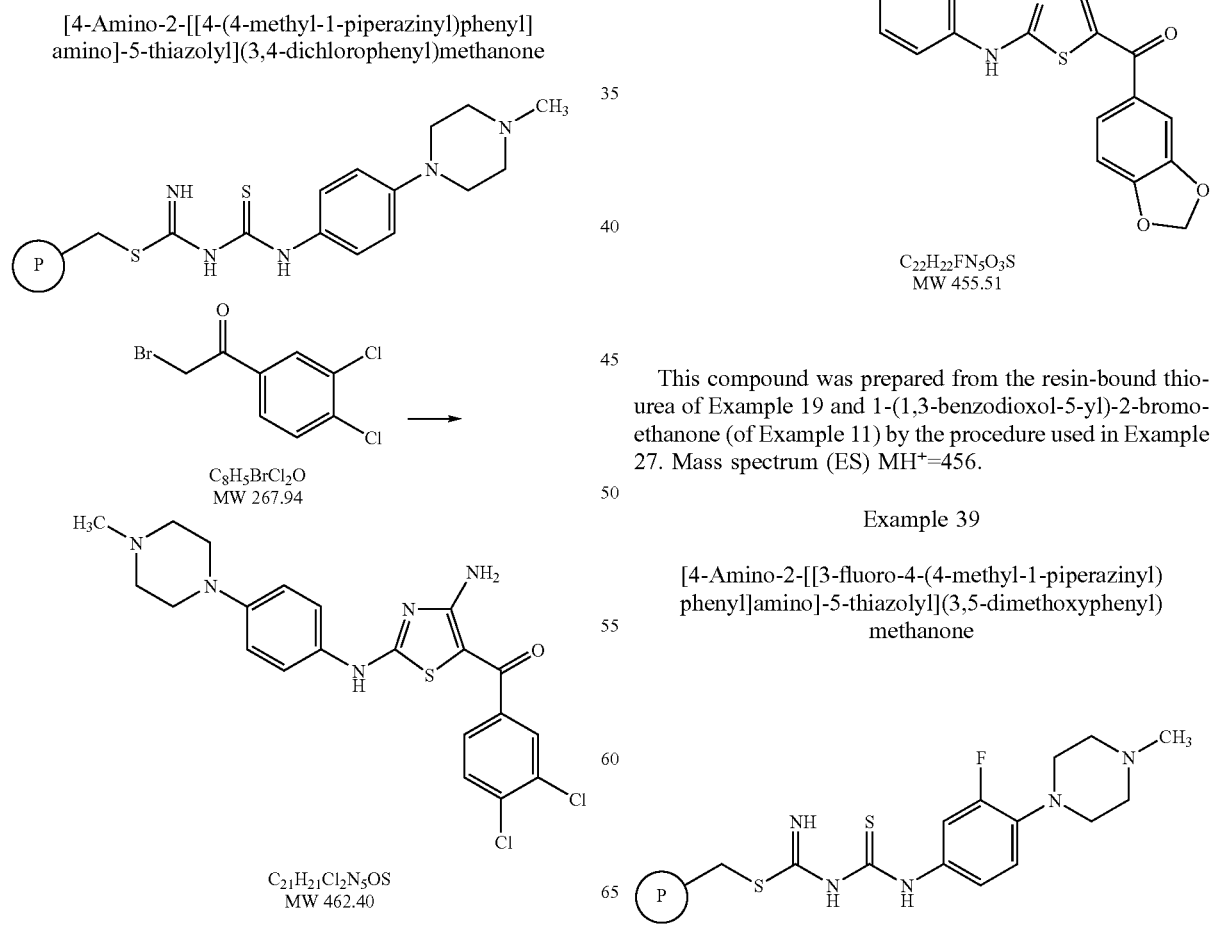

This compound was prepared from the resin-bound thiourea of Example 19 and 1-(1,3-benzodioxol-5-yl)-2-bromoethanone (of Example 11) by the procedure used in Example 27. Mass spectrum (ES) MH+=456.

Example 39

[4-Amino-2-[[3-fluoro-4-(4-methyl-1-piperazinyl)phenyl]amino]-5-thiazolyl](3,5-dimethoxyphenyl)methanone

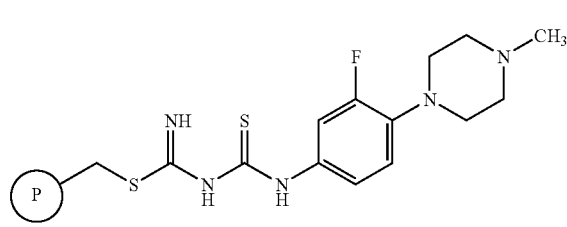

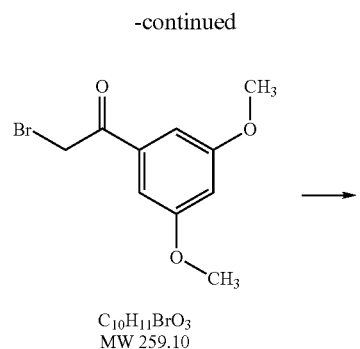

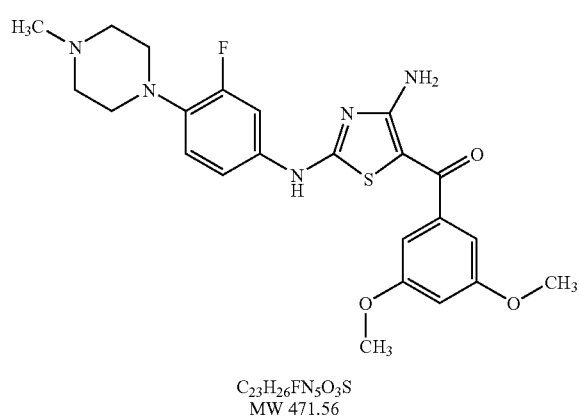

This compound was prepared from the resin-bound thiourea of Example 19 and 2-bromo-1-(3,5-dimethoxyphenyl)ethanone (of Example 9) by the procedure used in Example 27. Mass spectrum (ES) MH+=472.

Example 40

[4-Amino-2-[[3-fluoro-4-(4-methyl-1-piperazinyl)phenyl]amino]-5-thiazolyl](3-methoxyphenyl)methanone

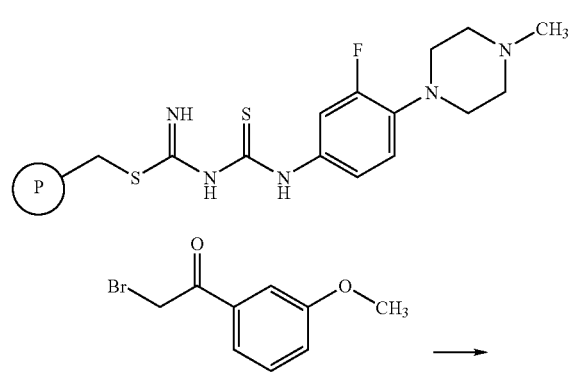

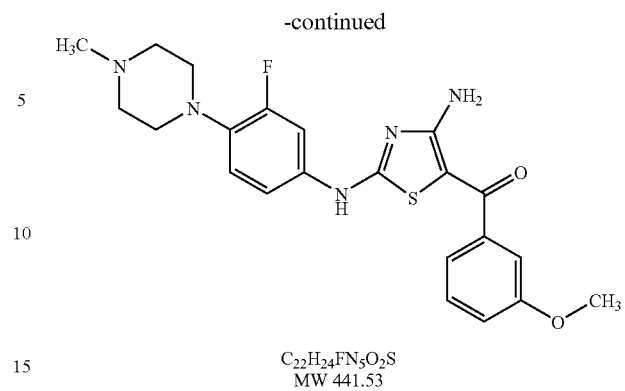

This compound was prepared from the resin-bound thiourea of Example 19 and 2-bromo-1-(3-methoxyphenyl)ethanone (Aldrich) by the procedure used in Example 27. Mass spectrum (ES) MH+=442.

Example 41

[4-Amino-2-[[4-[4-(1-methylethyl)-1-piperazinyl]phenyl]amino]-5-thiazolyl](2,3-dihydro-1,4-benzodioxin-6-yl)methanone

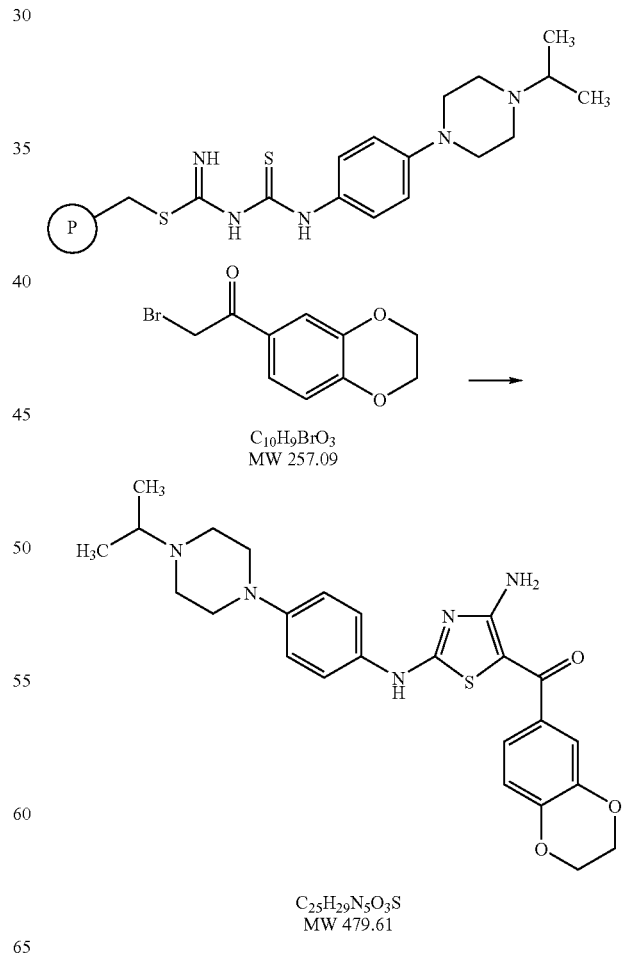

This compound was prepared from the resin-bound thiourea of Example 20 and 2-bromo-1-(2,3-dihydro-1,4-benzodioxin-6-yl)ethanone (Maybridge Chemical Company Ltd.) by the procedure used in Example 27. Mass, spectrum (ES) MH+=480.

Example 42

[4-Amino-2-[[4-[4-(1-methylethyl)-1-piperazinyl]phenyl]amino]-5-thiazolyl](1,3-benzodioxol-5-yl)methanone

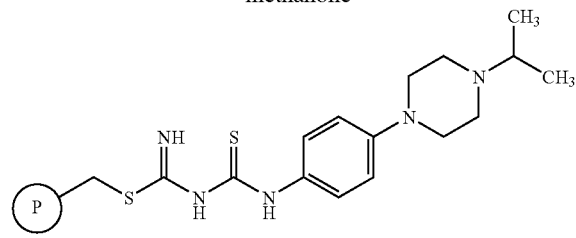

C9H7BrO3
MW 243.06

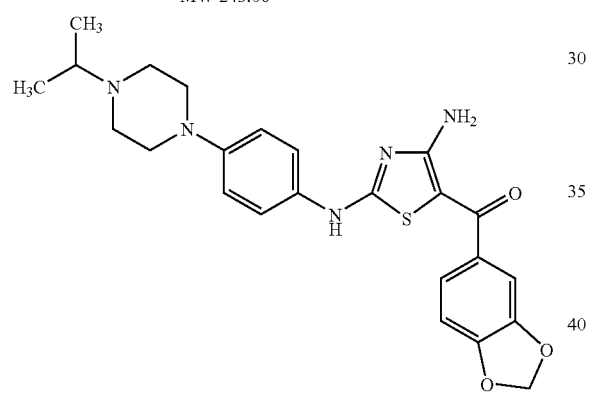

C24H27N5O3S
MW 465.58

This compound was prepared from the resin-bound thiourea of Example 20 and 1-(1,3-benzodioxol-5-yl)-2-bromoethanone (of Example 11) by the procedure used in Example 27. Mass spectrum (ES) MH+=466.

Example 43

[4-Amino-2-[[4-[4-(1-methylethyl)-1-piperazinyl]phenyl]amino]-5-thiazolyl](3-methoxyphenyl)methanone

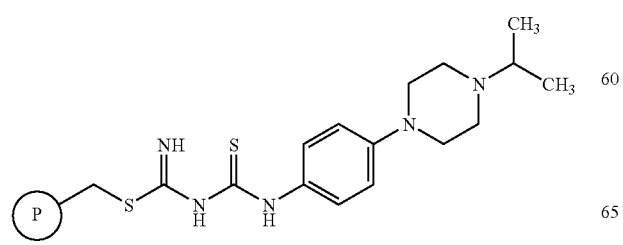

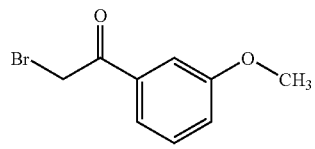

C9H9BrO2
MW 229.07

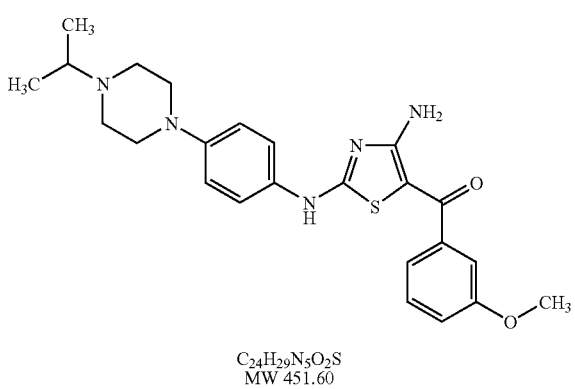

C24H29N5O2S
MW 451.60

This compound was prepared from the resin-bound thiourea of Example 20 and 2-bromo-1-(3-methoxyphenyl)ethanone (Aldrich) by the procedure used in Example 27. Mass spectrum (ES) MH+=452.

Example 44

[4-Amino-2-[[4-[4-(1-methylethyl)-1-piperazinyl]phenyl]amino]-5-thiazolyl](3,5-dimethoxyphenyl)methanone

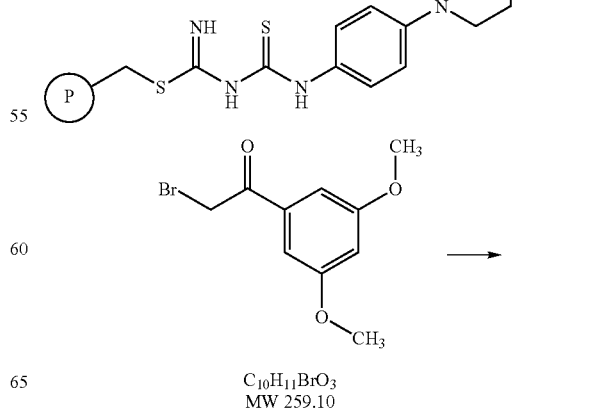

C10H11BrO3
MW 259.10

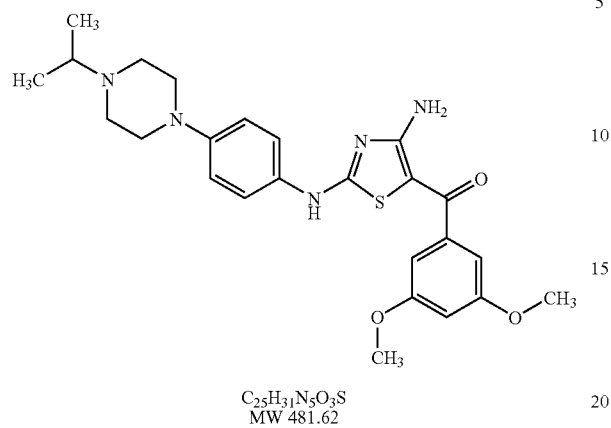

C25H31N5O3S
MW 481.62

This compound was prepared from the resin-bound thiourea of Example 20 and 2-bromo-1-(3,5-dimethoxyphenyl)ethanone (of Example 9) by the procedure used in Example 27. Mass spectrum (ES) MH+=482.

Example 45

N-[4-[[4-Amino-2-[[4-[4-(1-methylethyl)-1-piperazinyl]phenyl]amino]-5-thiazolyl]carbonyl]phenyl]acetamide

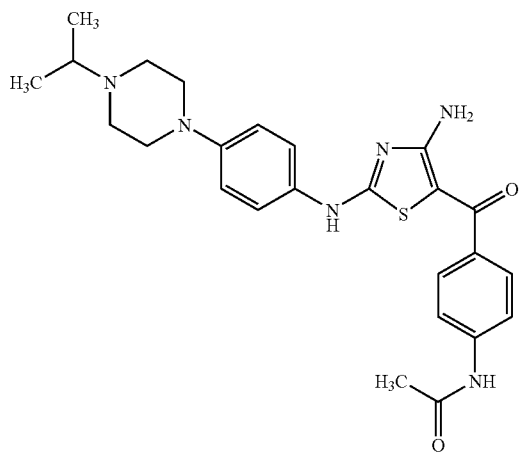

C25H30N6O2S
MW 478.62

This compound was prepared from the resin-bound thiourea of Example 20 and N-[4-(bromoacetyl)phenyl]acetamide (of Example 10) by the procedure used in Example 27. Mass spectrum (ES) MH+=479.

Example 46

[4-Amino-2-[[4-[4-(1-methylethyl)-1-piperazinyl]phenyl]amino]-5-thiazolyl][4-(diethylamino)phenyl]methanone

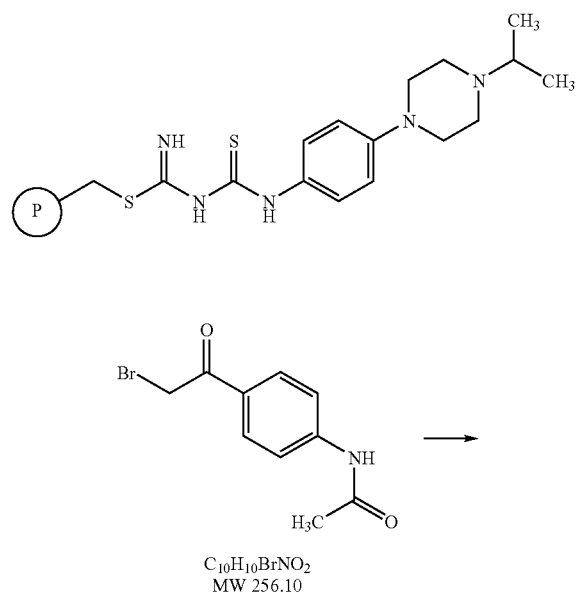

C10H10BrNO2
MW 256.10

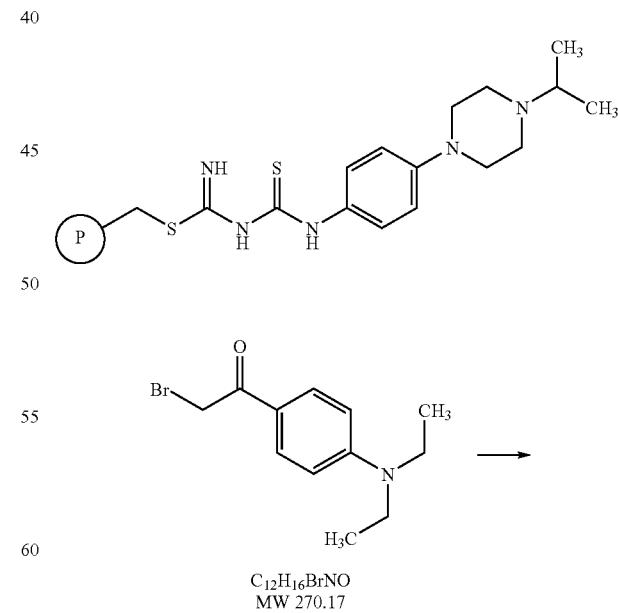

C12H16BrNO
MW 270.17

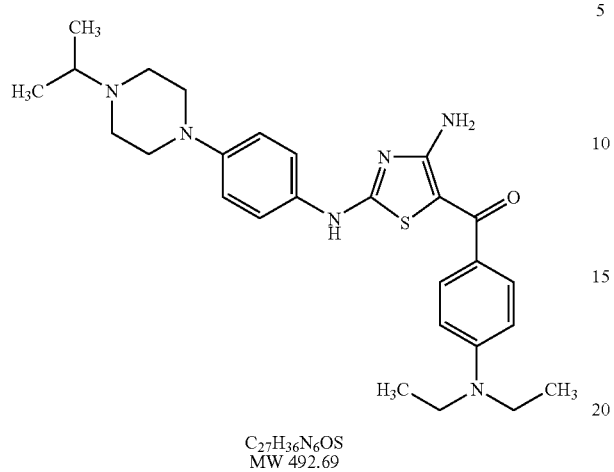

C₂₇H₃₆N₆OS
MW 492.69

This compound was prepared from the resin-bound thiourea of Example 20 and 2-bromo-1-[4-(diethylamino)phenyl]ethanone (Lancaster Synthesis) by the procedure used in Example 27. Mass spectrum (ES) MH⁺=493.

Example 47

1-Acetyl-4-[4-[[4-amino-5-[(1,3-benzodioxol-5-yl)carbonyl]-2-thiazolyl]amino]phenyl]piperazine

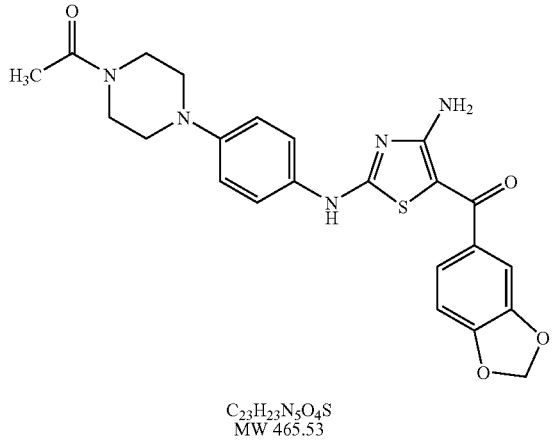

C₂₃H₂₃N₅O₄S
MW 465.53

This compound was prepared from the resin-bound thiourea of Example, 21 and 1-(1,3-benzodioxol-5-yl)-2-bromoethanone (of Example 11) by the procedure used in Example 27. Mass spectrum (ES) MH⁺=466.

Example 48

1-Acetyl-4-[4-[[4-amino-5-[4-(diethylamino)benzoyl]-2-thiazolyl]amino]phenyl]piperazino, trifluoroacetate salt

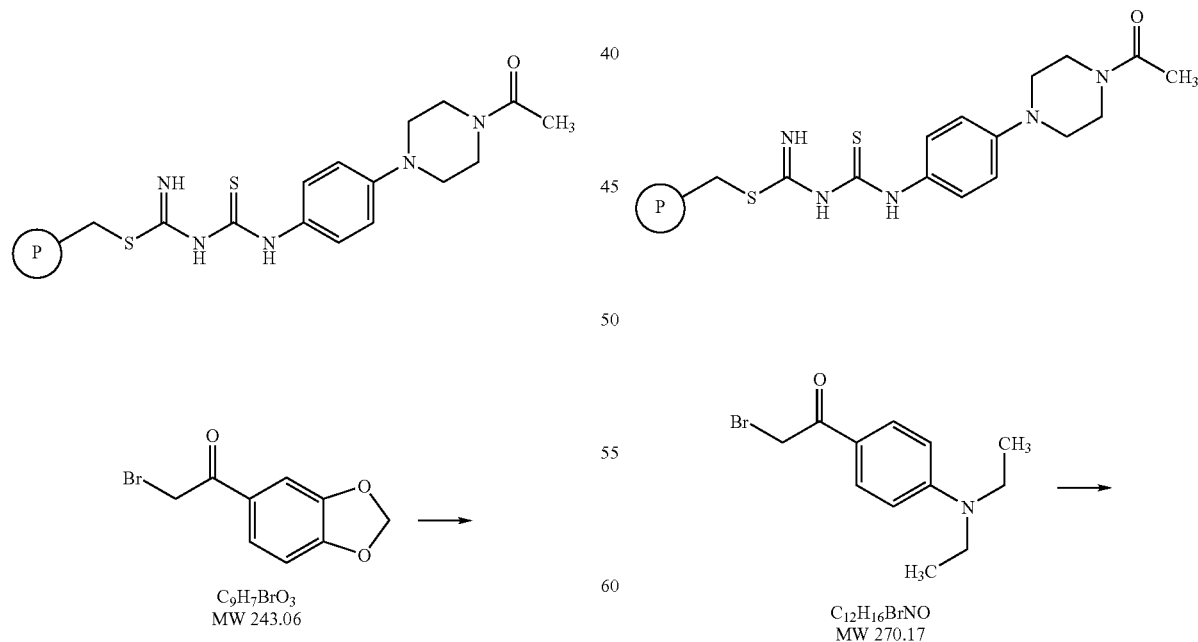

C₉H₇BrO₃
MW 243.06

C₁₂H₁₆BrNO
MW 270.17

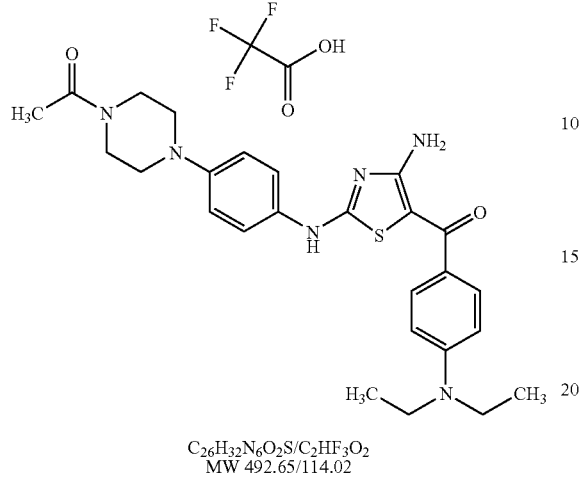

C₂₆H₃₂N₆O₂S/C₂HF₃O₂
MW 492.65/114.02

This compound was prepared from the resin-bound thiourea of Example 21 and 2-bromo-1-[4-(diethylamino)phenyl]ethanone (Lancaster Synthesis) by the procedure used in Example 27. The crude product was purified by HPLC using an Amicon $C_{18}$ 2×5 cm column with the following gradient: A (0.05% TFA/H₂O), B (0.05% TFA/CH₃CN), A to B gradient (10 to 75% over 10 minutes), flow rate: 20 mL/min. Mass spectrum (ES) MH⁺=493.

Example 49

[4-Amino-2-[[4-[4-(2-hydroxyethyl)-1-piperazinyl]phenyl]amino]-5-thiazolyl](2,3-dihydro-1,4-benzodioxin-6-yl)methanone

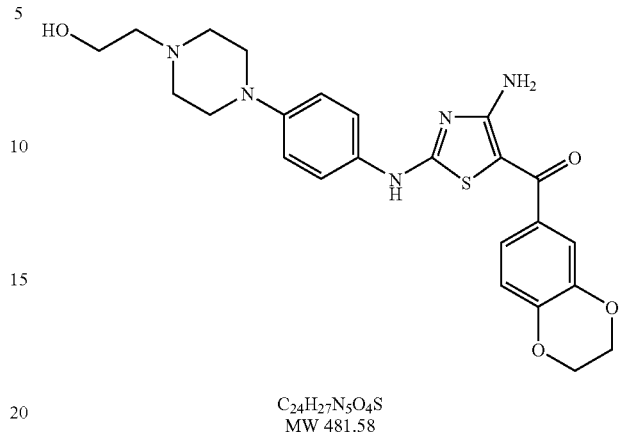

C₂₄H₂₇N₅O₄S
MW 481.58

This compound was prepared from the resin-bound thiourea of Example 22 and 2-bromo-1-(2,3-dihydro-1,4-benzodioxin-6-yl)ethanone (Maybridge Chemical Company Ltd.) by the procedure used in Example 27. Mass spectrum (ES) MH⁺=482.

Example 50

[4-Amino-2-[[4-[4-(2-hydroxyethyl)-1-piperazinyl]phenyl]amino]-5-thiazolyl][4-(1-pyrrolidinyl)phenyl]methanone

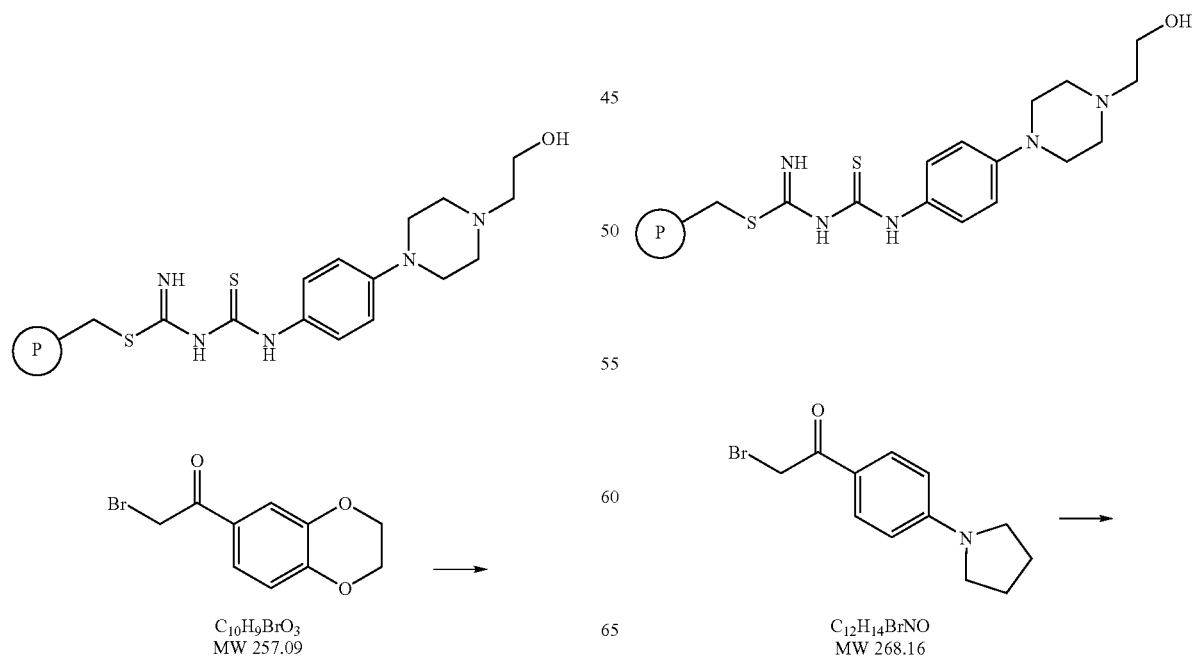

C₁₀H₉BrO₃
MW 257.09

C₁₂H₁₄BrNO
MW 268.16

-continued

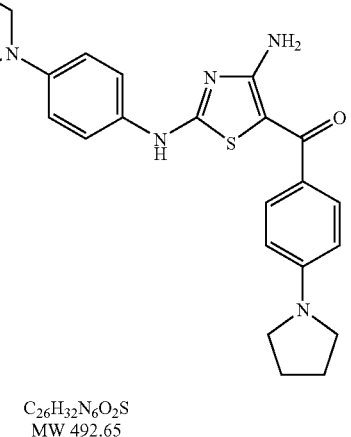

C₂₆H₃₂N₆O₂S
MW 492.65

This compound was prepared from the resin-bound thiourea of Example 22 and 2-bromo-1-[4-(1-pyrrolidinyl)phenyl]ethanone (Lancaster Synthesis) by the procedure used in Example 27. Mass spectrum (ES) MH⁺=493.

Example 51

[4-Amino-2-[[4-[4-(2-hydroxyethyl)-1-piperazinyl]phenyl]amino]-5-thiazolyl](3-fluorophenyl)methanone

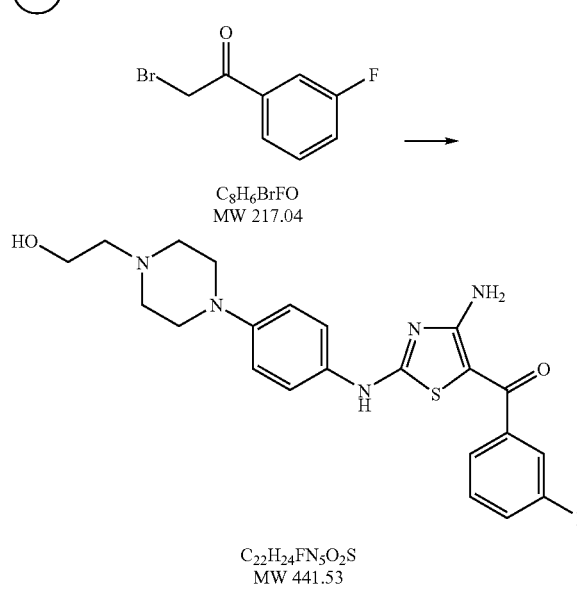

C₈H₆BrFO
MW 217.04

C₂₂H₂₄FN₅O₂S
MW 441.53

This compound was prepared from the resin-bound thiourea of Example. 22 and 2-bromo-1-(3-fluorophenyl)ethanone (Maybridge Chemical Company Ltd.) by the procedure used in Example 27. Mass spectrum (ES) MH⁺=442.

Example 52

[4-Amino-2-[[4-[4-(2-hydroxyethyl)-1-piperazinyl]phenyl]amino]-5-thiazolyl](3,5-difluorophenyl)methanone

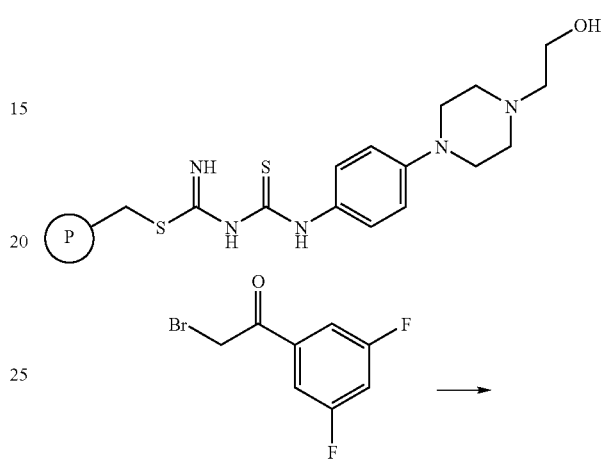

C₈H₅BrF₂O
MW 235.03

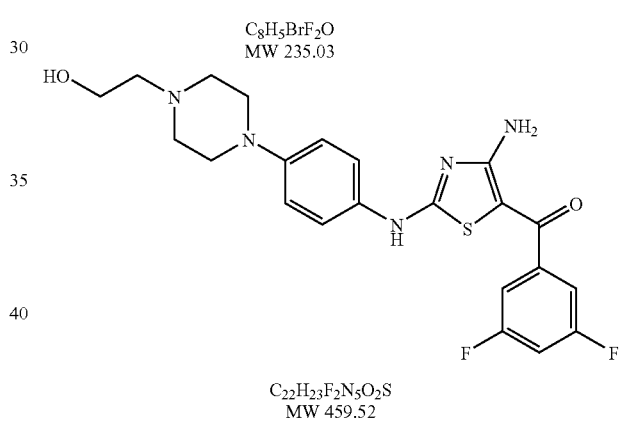

C₂₂H₂₃F₂N₅O₂S
MW 459.52

This compound was prepared from the resin-bound thiourea of Example 22 and 2-bromo-1-(3,5-difluorophenyl)ethanone (of Example 14) by the procedure used in Example 27. Mass spectrum (ES) MH⁺=460.

Example 53

[4-Amino-2-[[4-[4-(2-hydroxyethyl)-1-piperazinyl]phenyl]amino]-5-thiazolyl](3-methoxyphenyl)methanone

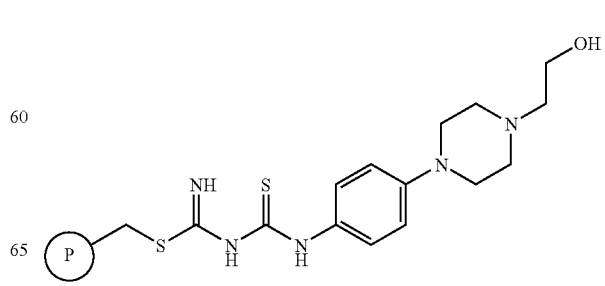

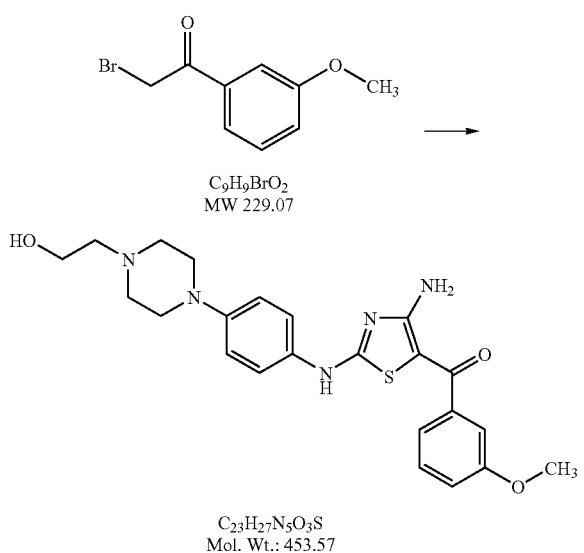

This compound was prepared from the resin-bound thiourea of Example 22 and 2-bromo-1-(3-methoxyphenyl)ethanone (Aldrich) by the procedure used in Example 27. Mass spectrum (ES) MH+=454.

Example 54

[4-Amino-2-[[4-(1-piperazinyl)phenyl]amino]-5-thiazolyl](3-fluorophenyl) methanone

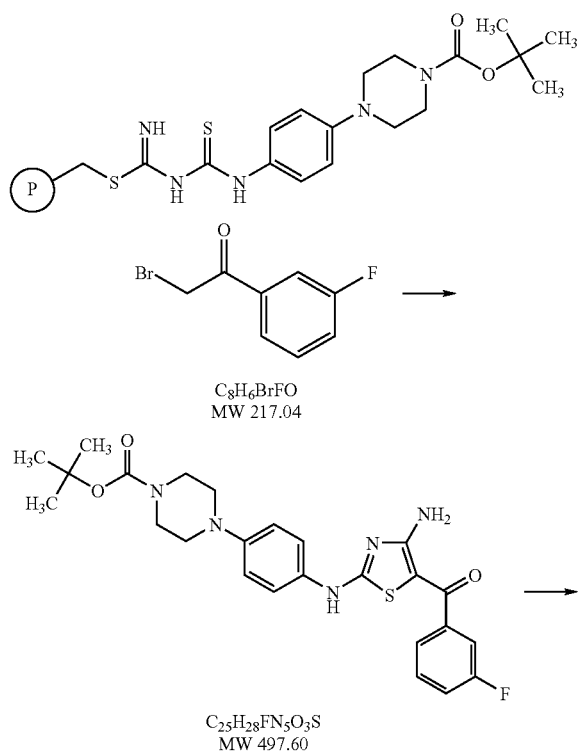

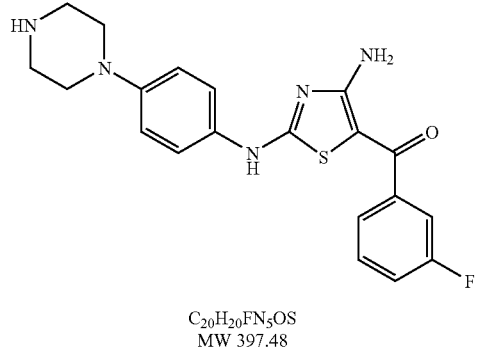

A. 4-[4-[[4-Amino-5-(3-fluorobenzoyl)-2-thiazolyl]amino]phenyl]-1-piperazine-carboxylic acid, 1,1-dimethylethyl Ester This compound was prepared from the resin-bound thiourea of Example 23A and 2-bromo-1-(3-fluorophenyl)ethanone (Maybridge Chemical Company Ltd.) by the procedure used in Example 27.

B. [4-Amino-2-[[4-(1-piperazinyl)phenyl]amino]-5-thiazolyl](3-fluorophenyl) methanone A mixture of 4-[4-[[4-amino-5-(3-fluorobenzoyl)-2-thiazolyl]amino]phenyl]-1-piperazinecarboxylic acid, 1,1-dimethylethyl ester (75 mg, 0.15 mmol) (from Step A above) and a solution of TFA/CH$_2$Cl$_2$ (1:1; 1.5 mL) was gently shaken for 1.5 h. The solution was evaporated in vacuo. To the residue was added resin-bound N,N-diisopropylethylamine (2.5 g, loading capacity: 3.8 mmol/g from Argonaut, Inc.) and CH$_2$Cl$_2$ (15 mL). After shaking overnight, the mixture was filtered and washed successively with CH$_3$OH and CH$_2$Cl$_2$. The solvent was evaporated in vacuo and the residue was triturated by diethyl ether/hexanes (1/9) to afford [4-amino-2-[[4-(1-piperazinyl)phenyl]amino]-5-thiazolyl](3-fluorophenyl)methanone (60 mg, 100%).

Example 55

[4-Amino-2-[[4-(1-piperazinyl)phenyl]amino)-5-thiazolyl][4-(1-pyrrolidinyl) phenyl]methanone

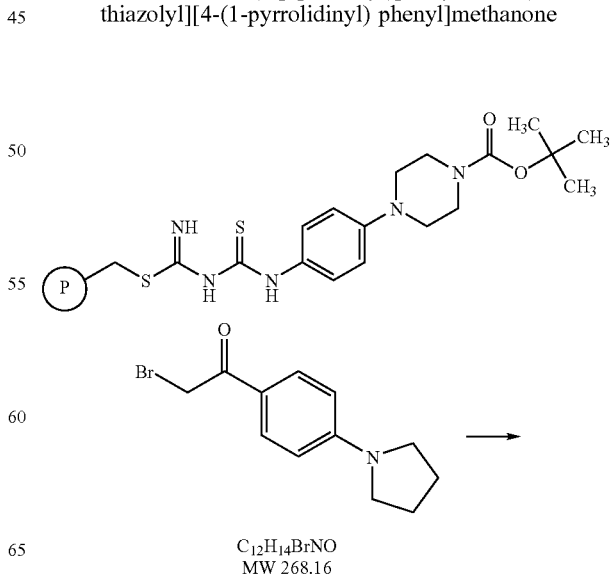

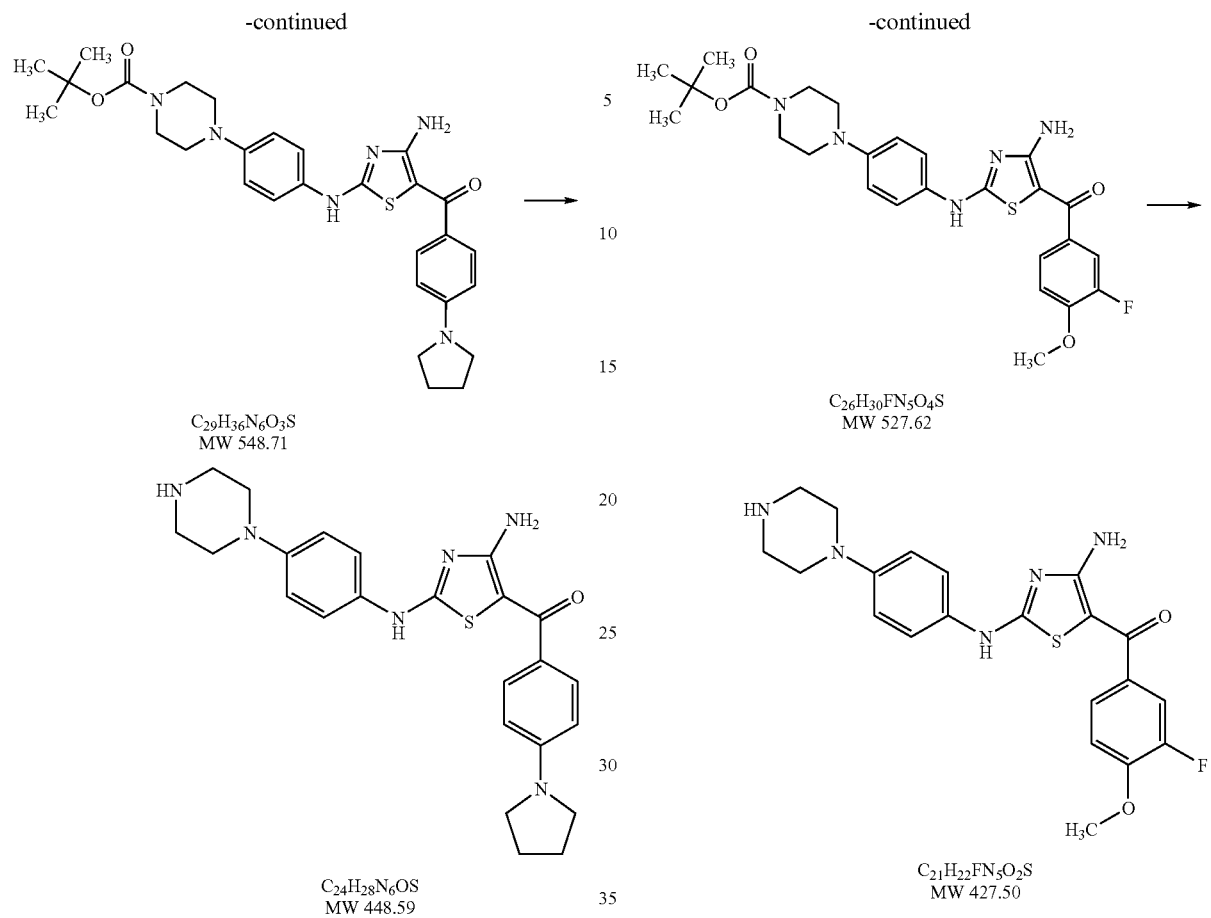

This compound was prepared from the resin-bound thiourea of Example 23A and 2-bromo-1-[4-(1-pyrrolidinyl)phenyl]ethanone (Lancaster Synthesis) by the procedures used in Example 54. Mass spectrum (ES) MH+=449.

Example 56

[4-Amino-2-[[4-(1-piperazinyl)phenyl]amino)-5-thiazolyl](3-fluoro-4-methoxyphenyl)methanone This compound was prepared from the resin-bound thiourea of Example 23A and 2-bromo-1-(3-fluoro-4-methoxyphenyl)ethanone (of Example 13) by the procedures used in Example 54. Mass spectrum (ES) MH+=428.

Example 57

[4-Amino-2-[[4-(4-methyl-1-piperazinyl)phenyl]amino]-5-thiazolyl][4-(2-hydroxyethyl)amino-3-nitrophenyl]methanone

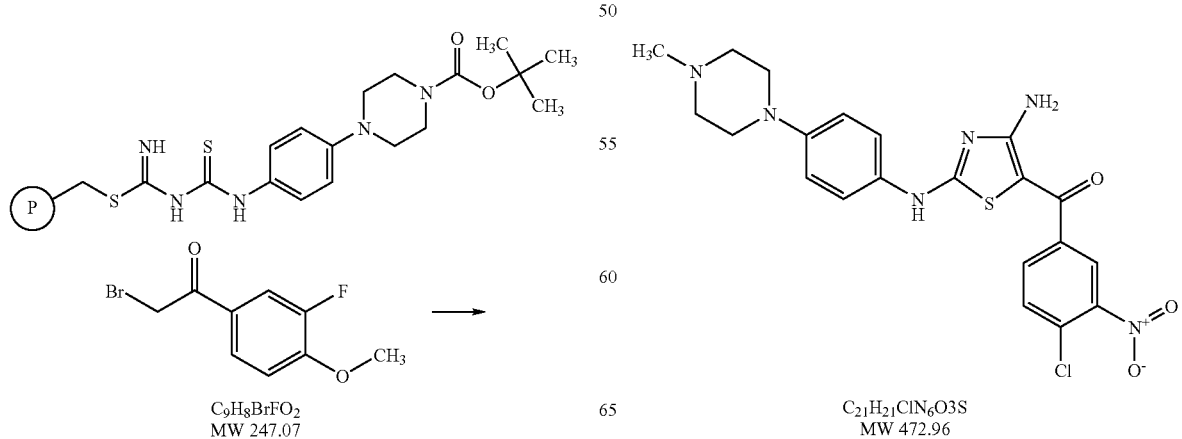

-continued

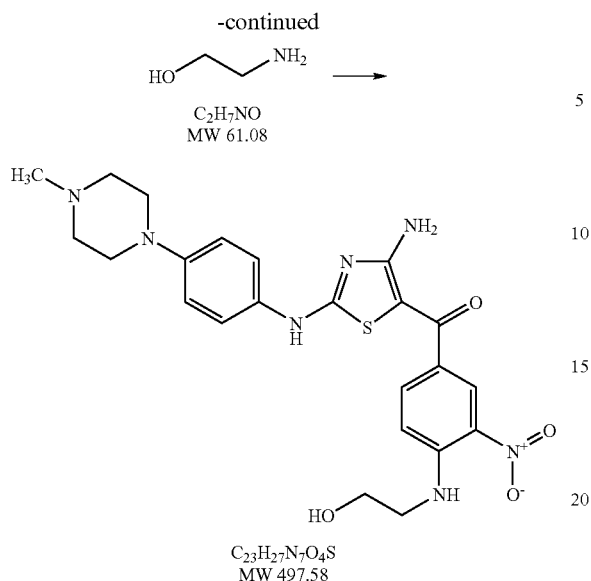

C₂H₇NO
MW 61.08

C₂₃H₂₇N₇O₄S
MW 497.58

A mixture of [4-amino-2-[[4-(4-methyl-1-piperazinyl)phenyl]amino]-5-thiazolyl](4-chloro-3-nitrophenyl)methanone (of Example 15; 0.25 g, 0.53 mmol), ethanolamine (0.13 mL, 2.12 mmol), N,N-diisopropylethylamine (Aldrich) (0.37 mL, 2.12 mmol) in n-butanol (10 mL) was heated at 100° C. overnight. The solvent was evaporated in vacuo and the residue was chromatographed on silica gel using MeOH/CH₂Cl₂ (1/9) as the eluent to afford 73 mg (28% yield) of the title compound. Mass spectrum (ES) MH⁺=498.

Example 58

[4-Amino-2-[[4-(4-methyl-1-piperazinyl)phenyl]amino]-5-thiazolyl][3-nitro-4-(1-pyrrolidinyl)phenyl]methanone

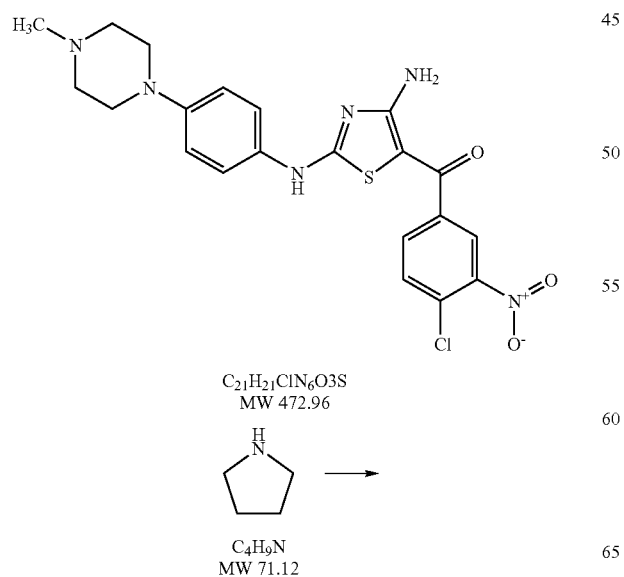

C₂₁H₂₁ClN₆O₃S
MW 472.96

C₄H₉N
MW 71.12

-continued

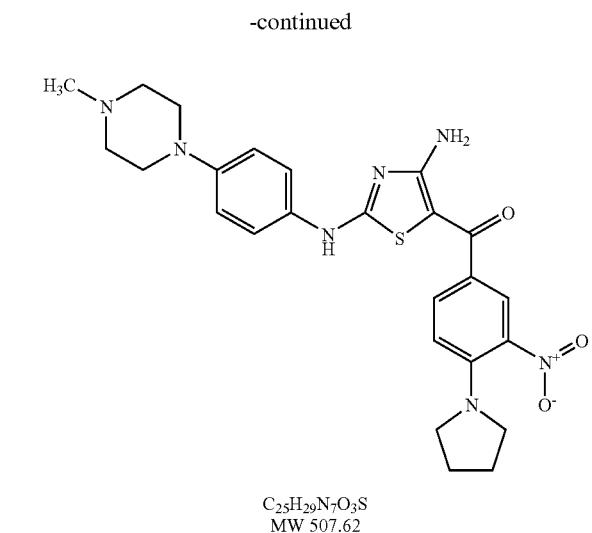

C₂₅H₂₉N₇O₃S
MW 507.62

This compound was prepared from the compound of Example 15 and pyrrolidine by the procedure used in Example 57. Mass spectrum (ES) MH⁺=508.

Example 59

[4-Amino-2-[[4-(4-methyl-1-piperazinyl)phenyl]amino]-5-thiazolyl][3-nitro-4-(4-morpholinyl)phenyl]methanone

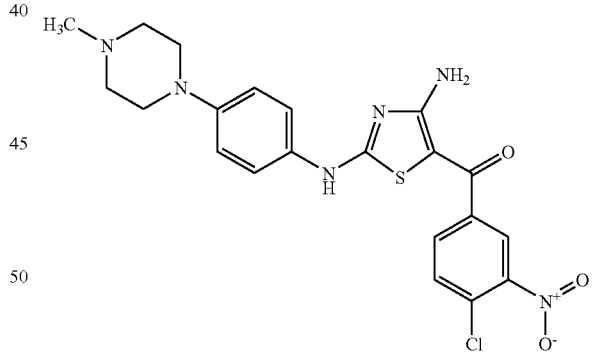

C₂₁H₂₁ClN₆O₃S
MW 472.96

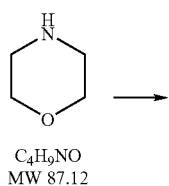

C₄H₉NO
MW 87.12

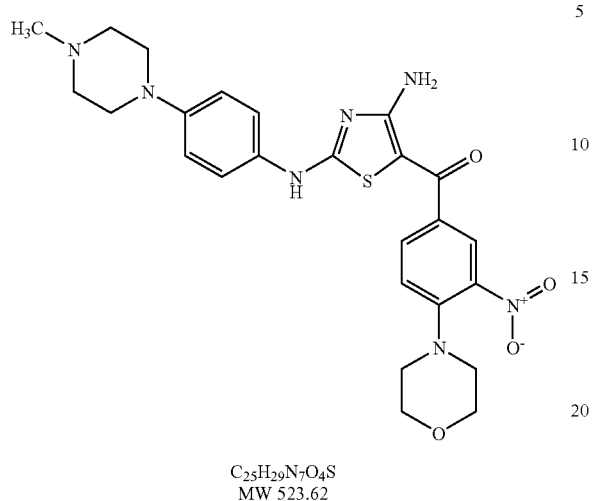

This compound was prepared from the compound of Example 15 and morpholine by the procedure used in Example 57. Mass spectrum (ES) MH+=524.

Example 60

[4-Amino-2-[[4-(4-methyl-1-piperazinyl)phenyl]amino]-5-thiazolyl][3-nitro-4-[(2-methoxyethyl)amino]phenyl]methanone

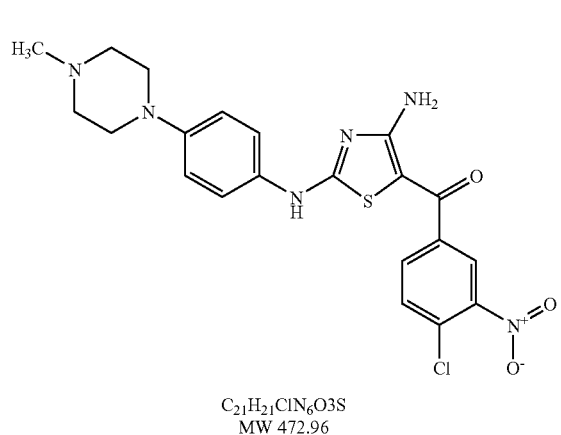

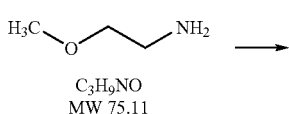

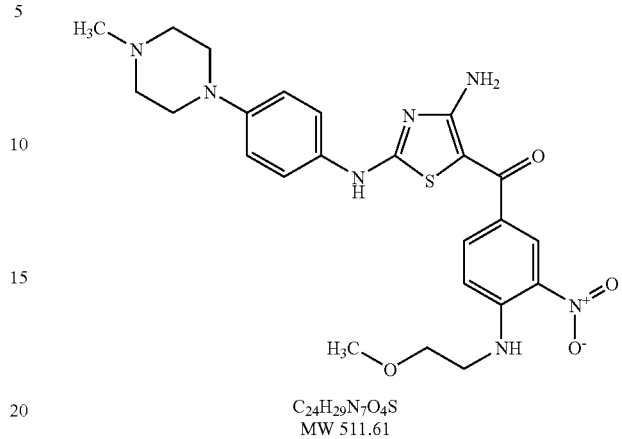

This compound was prepared from the compound of Example 15 and 2-methoxyethanamine(Aldrich) by the procedure used in Example 57. Mass spectrum (ES) MH+=512.

Example 61 racemic [4-Amino-2-[[4-(4-methyl-1-piperazinyl)phenyl]amino]-5-thiazolyl][3-nitro-4-[3-(hydroxymethyl)-1-piperidinyl]phenyl]methanone

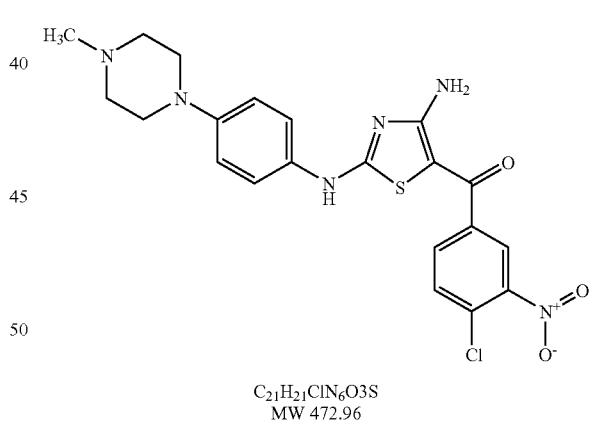

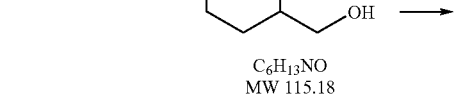

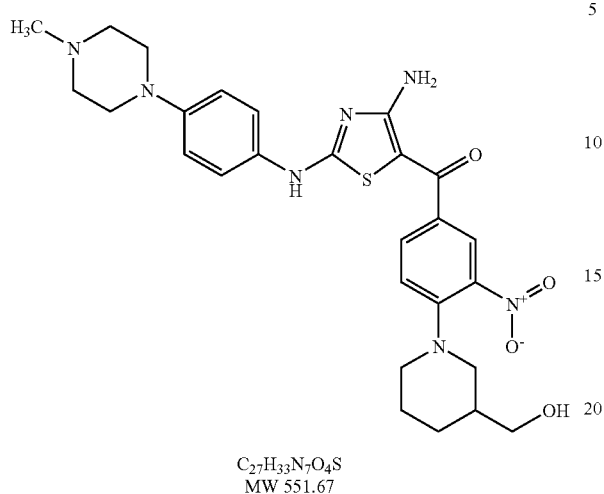

C₂₇H₃₃N₇O₄S
MW 551.67

This compound was prepared from the compound of Example 15 and racemic 3-piperidinemethanol (Aldrich) by the procedure used in Example 57. Mass spectrum (ES) MH⁺=552.

Example 62 racemic [4-Amino-2-[[4-(4-methyl-1-piperazinyl)phenyl]amino]-5-thiazolyl][3-nitro-4-(2-methyl-1-pyrrolidinyl)phenyl]methanone

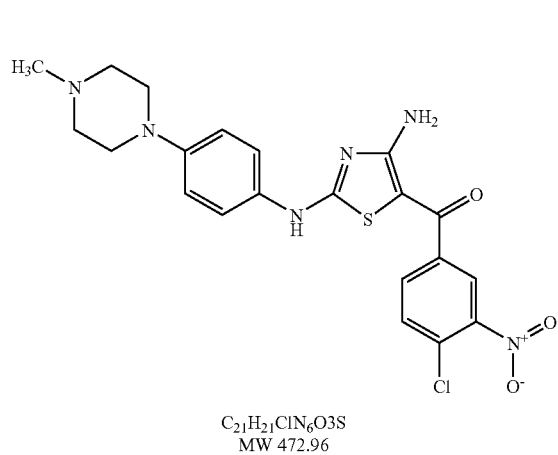

C₂₁H₂₁ClN₆O₃S
MW 472.96

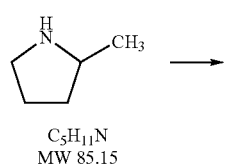

C₅H₁₁N
MW 85.15

This compound was prepared from the compound of Example 15 and racemic 2-methylpyrrolidine (Alfa Aesar) by the procedure used in Example 57. Mass spectrum (ES) MH⁺=522.

Example 63

(R)-[4-Amino-2-[[4-(4-methyl-1-piperazinyl)phenyl]amino]-5-thiazolyl][3-nitro-4-[[1-(hydroxymethyl)-3-methylbutyl]amino]phenyl]methanone

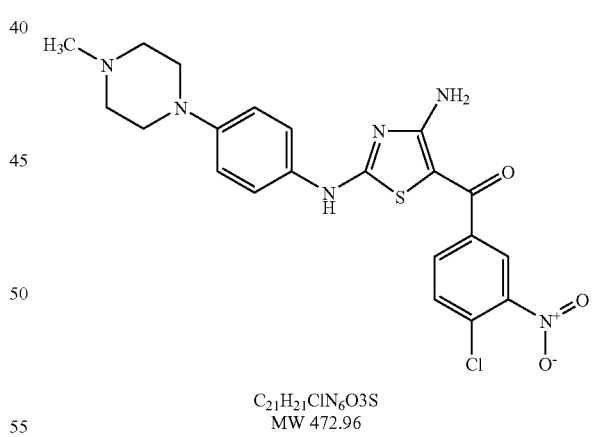

C₂₁H₂₁ClN₆O₃S
MW 472.96

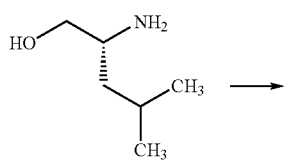

C₆H₁₅NO
MW 117.19

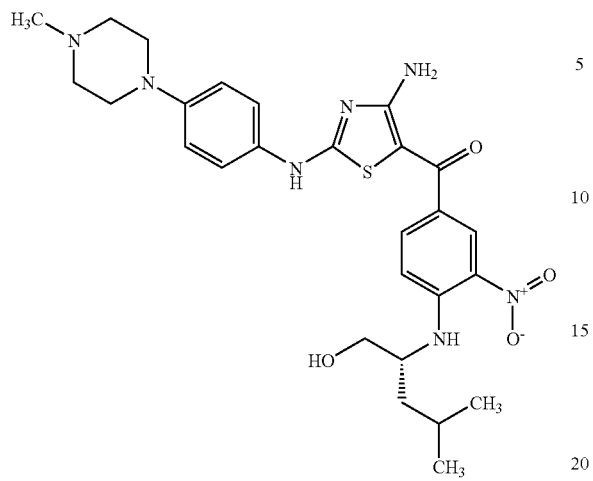

This compound was prepared from the compound of Example 15 and (R)-2-amino-4-methyl-1-pentanol (Aldrich) by the procedure used in Example 57. Mass spectrum (ES) MH+=554.

Example 64

[4-Amino-2-[[4-(4-methyl-1-piperazinyl)phenyl]amino]-5-thiazolyl][3-nitro-4-(4-hydroxy-1-piperidinyl)phenyl]methanone

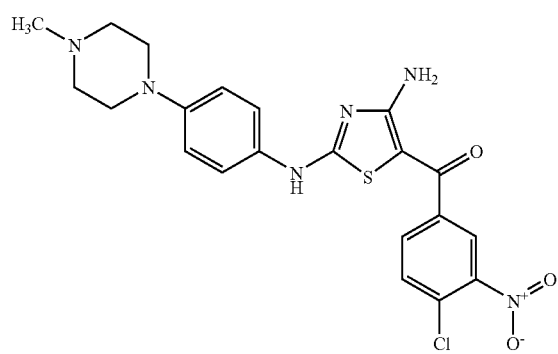

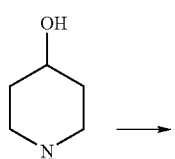

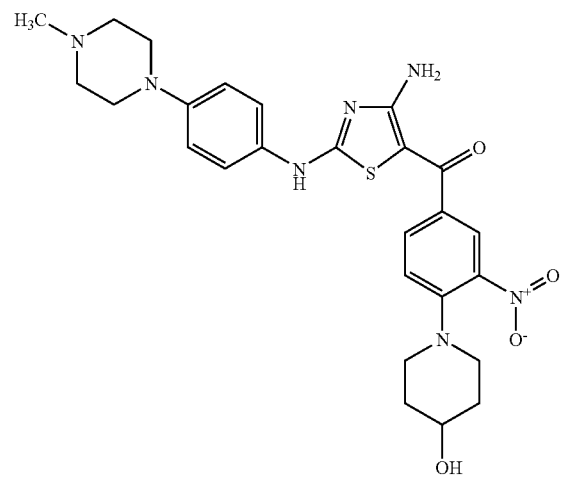

This compound was prepared from the compound of Example 15 and 4-piperidinol (Aldrich) by the procedure used in Example 57. Mass spectrum (ES) MH+=538.

Example 65

[4-Amino-2-[[4-(4-methyl-1-piperazinyl)phenyl]amino]-5-thiazolyl][3-amino-4-(4-pyrrolidinyl)phenyl]methanone

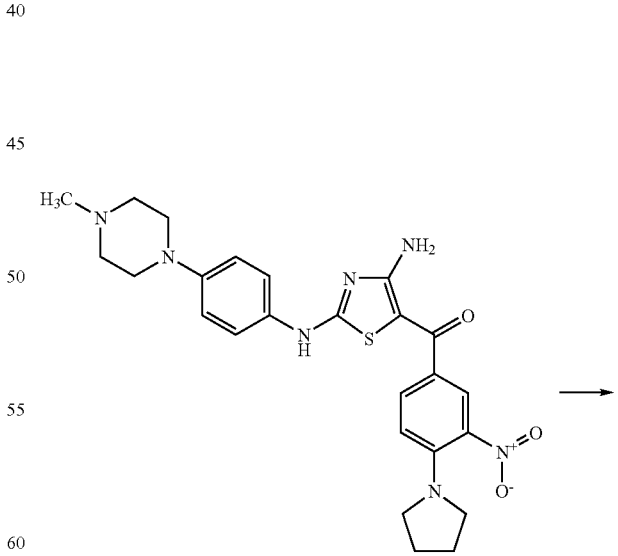

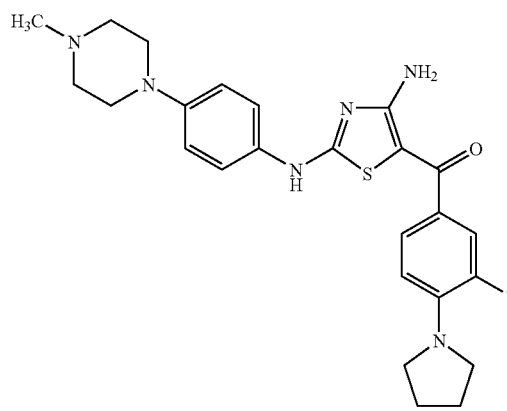

C₂₅H₃₁N₇OS
MW 477.64

A solution of [4-Amino-2-[[4-(4-methyl-1-piperazinyl)phenyl]amino]-5-thiazolyl][3-nitro-4-(1-pyrrolidinyl)phenyl]methanone (of Example 58; 0.16 g, 0.32 mmol), NH₂NH₂ (2 mL), 10% Pd/C (5 mg), and 2-propanol (12 mL) was heated at reflux for 1 h. The mixture was filtered through a Celite™ pad and concentrated in vacuo. Flash chromatography with 4:1 dichloromethane/methanol furnished [4-amino-2-[[4-(4-methyl-1-piperazinyl)phenyl]amino]-5-thiazolyl][3-amino-4-(4-pyrrolidinyl)phenyl]methanone (91 mg, 61% yield).

Example 66

(R)-[3-Amino-4-[1-(hydroxymethyl)-3-methylbutyl]amino]phenyl][4-amino-2-[[4-(4-methyl-1-piperazinyl)phenyl]amino]-5-thiazolyl]methanone

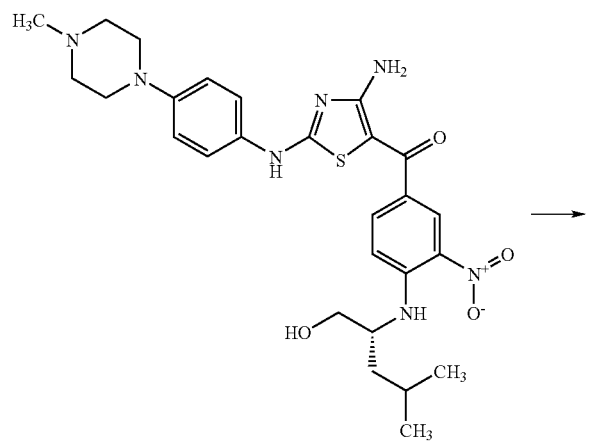

C₂₇H₃₅N₇O₄S
MW 553.69

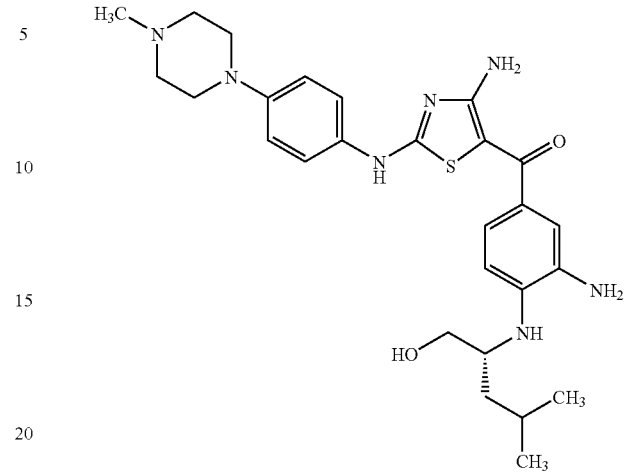

C₂₇H₃₇N₇O₂S
MW 523.71

A solution of (R)-[4-amino-2-[[4-(4-methyl-1-piperazinyl)phenyl]amino]-5-thiazolyl][3-nitro-4-[[1-(hydroxymethyl)-3-methylbutyl]amino]phenyl]methanone (of Example 63; 30 mg, 0.05 mmol), NH₂NH₂ (0.5 mL), 10% Pd/C (5 mg), and 2-propanol (2 mL) was heated at reflux for 1 h. The mixture was filtered through a Celite™ pad and concentrated in vacuo. Flash chromatography with 4:1 dichloromethane/methanol furnished (R)-[3-amino-4-[[1-(hydroxymethyl)-3-methylbutyl]amino]phenyl][4-amino-2-[[4-(4-methyl-1-piperazinyl)phenyl]amino]-5-thiazolyl]methanone (15 mg, 53% yield).

Example 67

[4-Amino-2-[[3-fluoro-4-(4-methyl-1-piperazinyl)phenyl]amino]-5-thiazolyl](2,3-dihydro-1,4-benzodioxin-5-yl)methanone

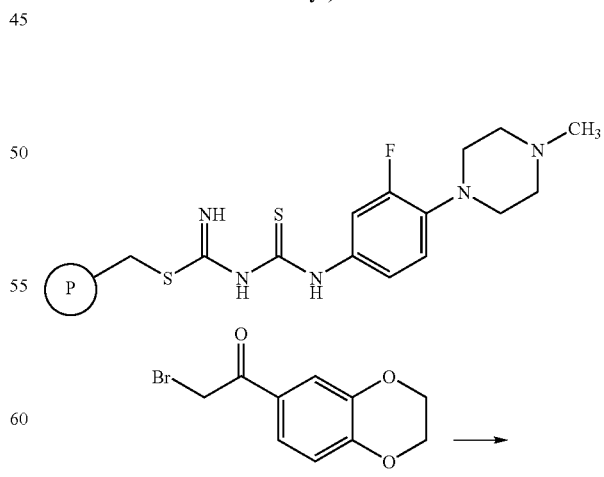

C₁₀H₉BrO₃
MW 257.09

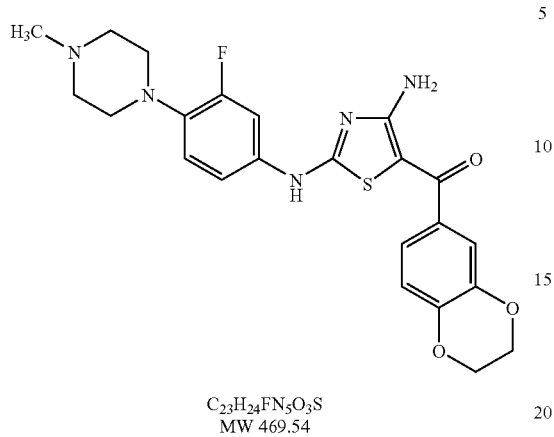

C₂₃H₂₄FN₅O₃S
MW 469.54

This compound was prepared from the resin-bound thiourea of Example 19 and 2-bromo-1-(2,3-dihydro-1,4-benzodioxin-6-yl)ethanone (Maybridge Chemical Company Ltd.) by the procedure used in Example 27. Mass spectrum (ES) MH⁺=470.

Example 68

[4-Amino-2-[[3-fluoro-4-(4-methyl-1-piperazinyl)phenyl]amino]-5-thiazolyl][4-(1-pyrrolidinyl)phenyl]methanone

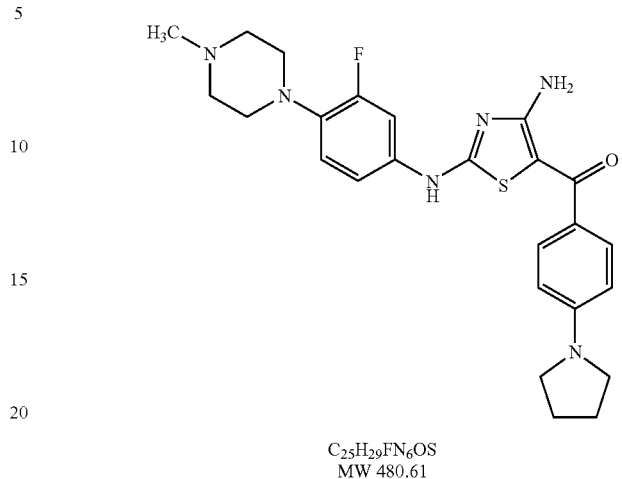

C₂₅H₂₉FN₆OS
MW 480.61

This compound was prepared from the resin-bound thiourea of Example 19 and 2-bromo-1-[4-(1-pyrrolidinyl)phenyl]ethanone (Lancaster) by the procedure used in Example 27. Mass spectrum (ES) MH⁺=481.

Example 69

{4-Amino-2-[4-(4-isopropyl-piperazin-1-yl)-phenylamino]-thiazol-5-yl}-(3-methoxy-phenyl)-methanone (with phosphoric acid)

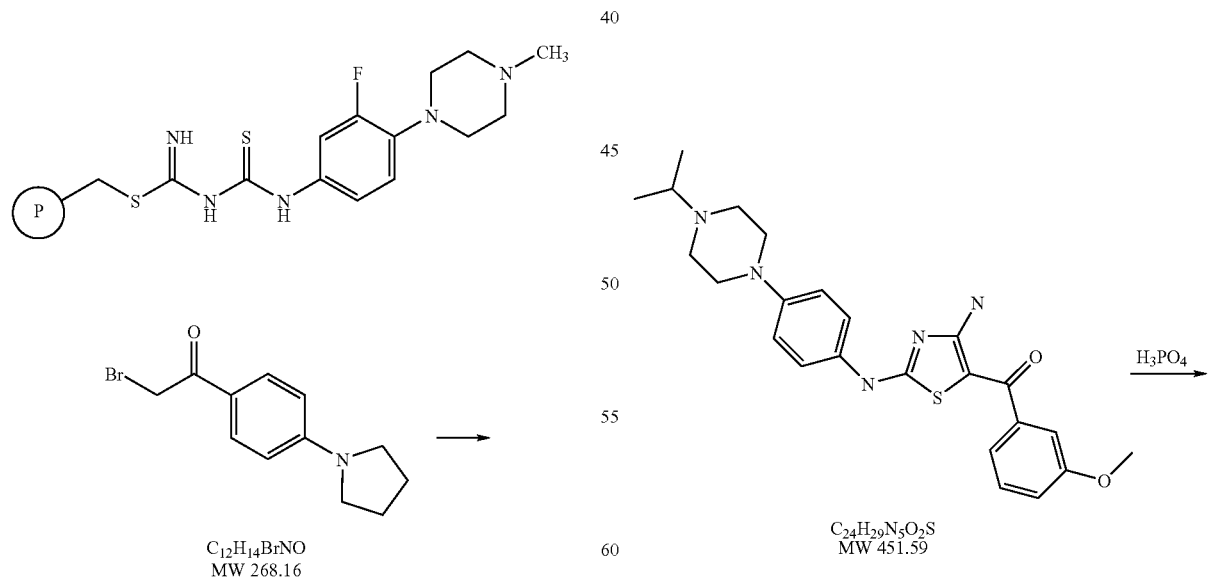

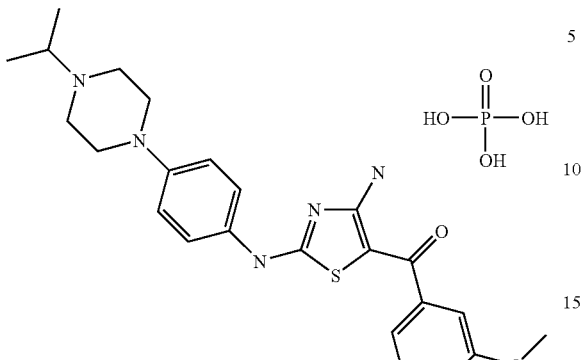

C₂₄H₂₉N₅O₂S•H₃PO₄
MW 549.60

A solution of {4-amino-2-[4-(4-isopropyl-piperazin-1-yl)-phenylamino]-thiazol-5-yl}-(3-methoxy-phenyl)-methanone (of Example 43; 113 mg, 0.25 mmol) was dissolved in hot ethanol (10 ml) and to this was added 25 mg of phosphoric acid in ethanol (1 ml). This was cooled and crystals were collected and dried to furnish {4-Amino-2-[4-(4-isopropyl-piperazin-1-yl)-phenylamino]-thiazol-5-yl}-(3-methoxy-phenyl)-methanone; compound with phosphoric acid. MicroAnalysis C, H, N, P, and S.

Example 70

{4-Amino-2-[4-(4-methyl-piperazin-1-yl)-phenylamino]-thiazol-5-yl}(3-methylsulfanyl-phenyl)-methanone

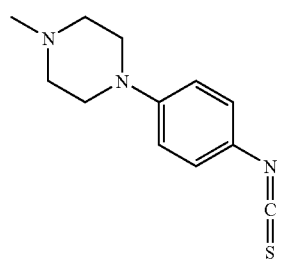

C₁₂H₁₅N₃S
MW 233.34

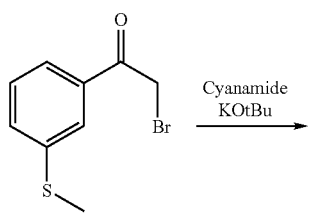

C₉H₉BrOS
MW 245.14

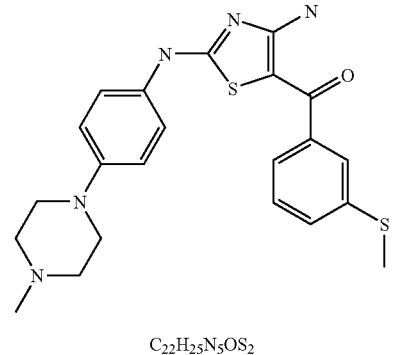

C₂₂H₂₅N₅OS₂
MW 439.60

To a mixture of 1-(4-isothiocyanatophenyl)-4-methylpiperazine (of Example 1; 0.466 g, 2.0 mmol) and cyanamide (0.088 g, 2.1 mmol) in acetonitrile (3 mL) and t-butanol (5 ml), a solution of potassium tert-butoxide (2.0 mL, 1.0 M in tert-BuOH) was added. After 30 minutes at room temperature, 2-bromo-1-(3-methylsulfanyl-phenyl)ethanone (which can be prepared by the procedure of Rogers, N. H. et. al. EP 87953; 0.49 g, 2.0 mmol) was added. The reaction mixture was stirred at room temperature for 1 hour and then refluxed for 15 minutes. The cooled mixture was diluted with ethyl acetate and washed in turn with saturated aqueous sodium carbonate and brine. The dried (sodium sulfate) solution was evaporated and the residue chromatographed on silica gel. Elution of the desired product with 9:1 dichloromethane/methanol and crystallization from ethyl acetate/hexane provided 0.439 g (50% yield) of [4-amino-2-[[4-(4-methyl-1-piperazinyl)phenyl]amino]-5-thiazolyl](3-methylsulfanyl-phenyl)methanone. Mass spectrum (ES) MH⁺=440.

Example 71

(4-Amino-2-{4-[4-(3-hydroxy-propyl)-piperazin-1-yl]-phenylamino}-thiazol-5-yl)-(3-fluoro-phenyl)-methanone

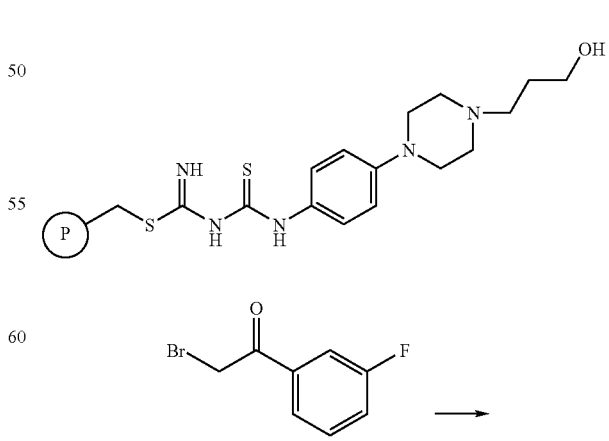

C₈H₆BrFO
Mol. Wt.: 217.04

-continued

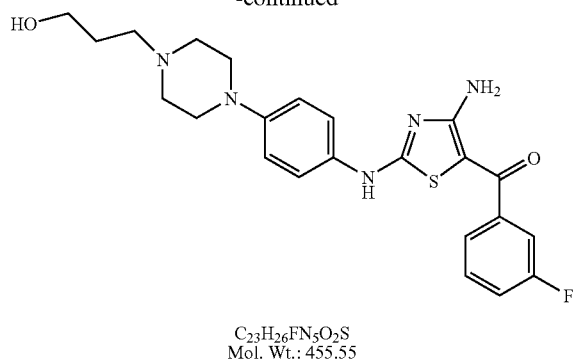

C₂₃H₂₆FN₅O₂S
Mol. Wt.: 455.55

This compound was prepared from the resin-bound thiourea of Example 23F and 2-bromo-1-(3-fluorophenyl)ethanone (Maybridge Chemical Company Ltd.) by the procedure used in Example 27. Mass spectrum (ES) MH⁺=456.

Example 72

(4-Amino-2-{4-[4-(3-hydroxy-propyl)-piperazin-1-yl]-phenylamino}-thiazol-5-yl)-(3-methoxy-phenyl)-methanone

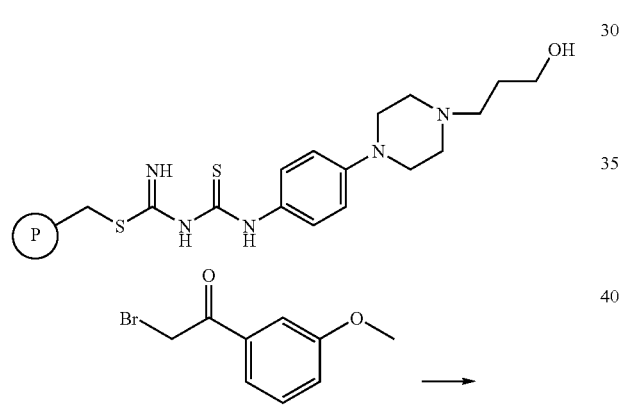

C₉H₉BrO₂
Mol. Wt.: 229.07

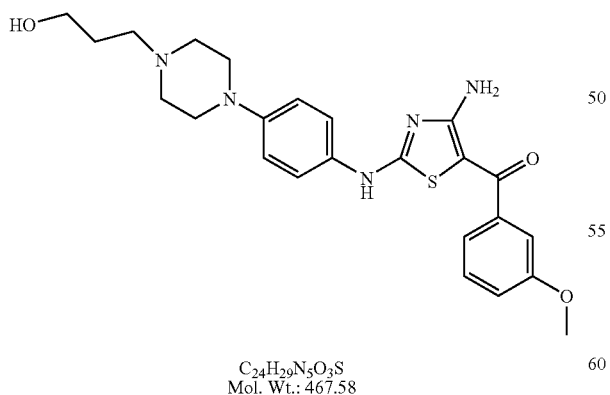

C₂₄H₂₉N₅O₃S
Mol. Wt.: 467.58

This compound was prepared from the resin-bound thiourea of Example 23F and 2-bromo-1-(3-methoxyphenyl)ethanone (Aldrich) by the procedure used in Example 27. Mass spectrum (ES) MH⁺=468.

Example 73

3-(4-Amino-2-{4-[4-(3-hydroxy-propyl)-piperazin-1-yl]-phenylamino}-thiazole-5-carbonyl)-benzonitrile

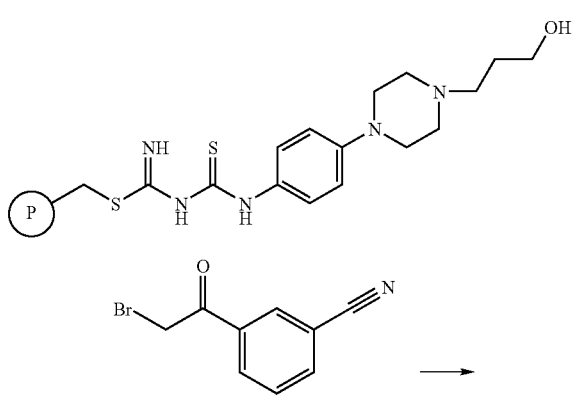

C₉H₆BrNO
Mol. Wt.: 224.05

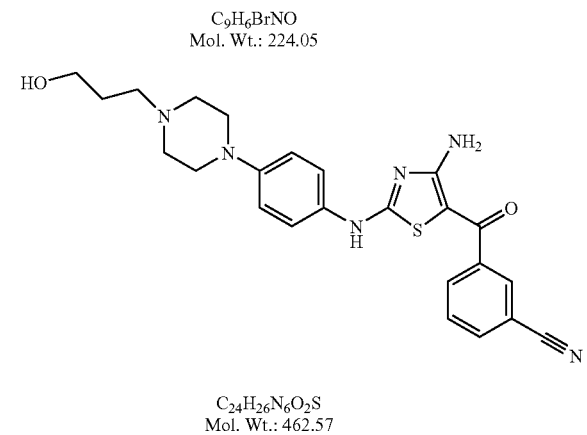

C₂₄H₂₆N₆O₂S
Mol. Wt.: 462.57

This compound was prepared from the resin-bound thiourea of Example 23F and 2-bromo-1-(3-cyanophenyl)ethanone (which can be prepared by the procedure of Aloup, J.-C. et al., WO 9512594 A1 19950511) by the procedure used in Example 27. Mass spectrum (ES) MH⁺=463.

Example 74

(4-Amino-2-{4-[4-(3-hydroxy-propyl)-piperazin-1-yl]-phenylamino}-thiazol-5-yl)-(3-nitro-phenyl)-methanone

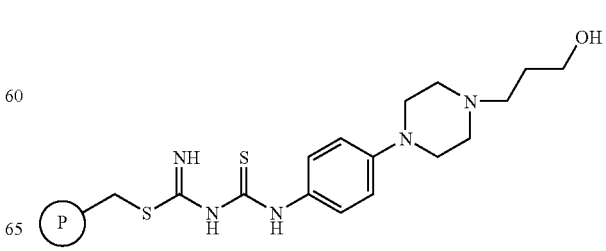

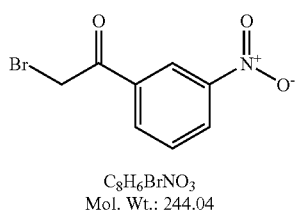

C₈H₆BrNO₃
Mol. Wt.: 244.04

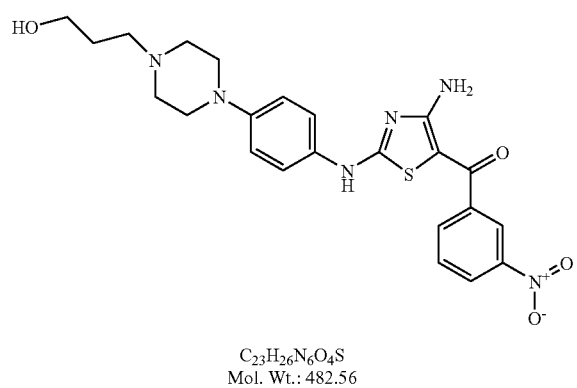

C₂₃H₂₆N₆O₄S
Mol. Wt.: 482.56

This compound was prepared from the resin-bound thiourea of Example 23F and 2-bromo-1-(3-nitrophenyl)ethanone (which is available from Aldrich) by the procedure used in Example 27. Mass spectrum (ES) MH⁺=483.

Example 75

(4-Amino-2-{4-[4-(3-hydroxy-propyl)-piperazin-1-yl]-phenylamino}-thiazol-5-yl)-m-tolyl-methanone

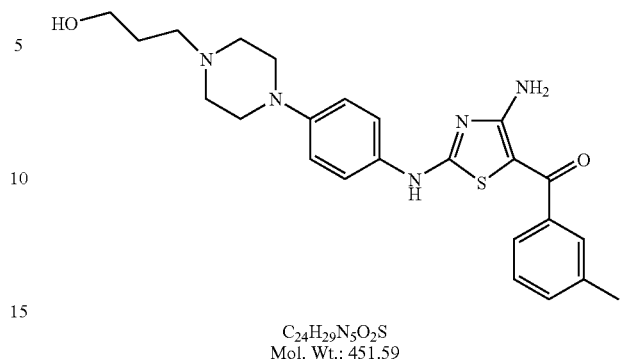

C₂₄H₂₉N₅O₂S
Mol. Wt.: 451.59

This compound was prepared from the resin-bound thiourea of Example 23F and 2-bromo-1-(3-methylphenyl)ethanone (which can be prepared by the procedure of Itoh, T. et al. EP 1020426) by the procedure used in Example 27. Mass spectrum (ES) MH⁺=452.

Example 76

(4-Amino-2-{4-[4-(3-hydroxy-propyl)-piperazin-1-yl]-phenylamino}-thiazol-5-yl)-(3-ethyl-phenyl)-methanone

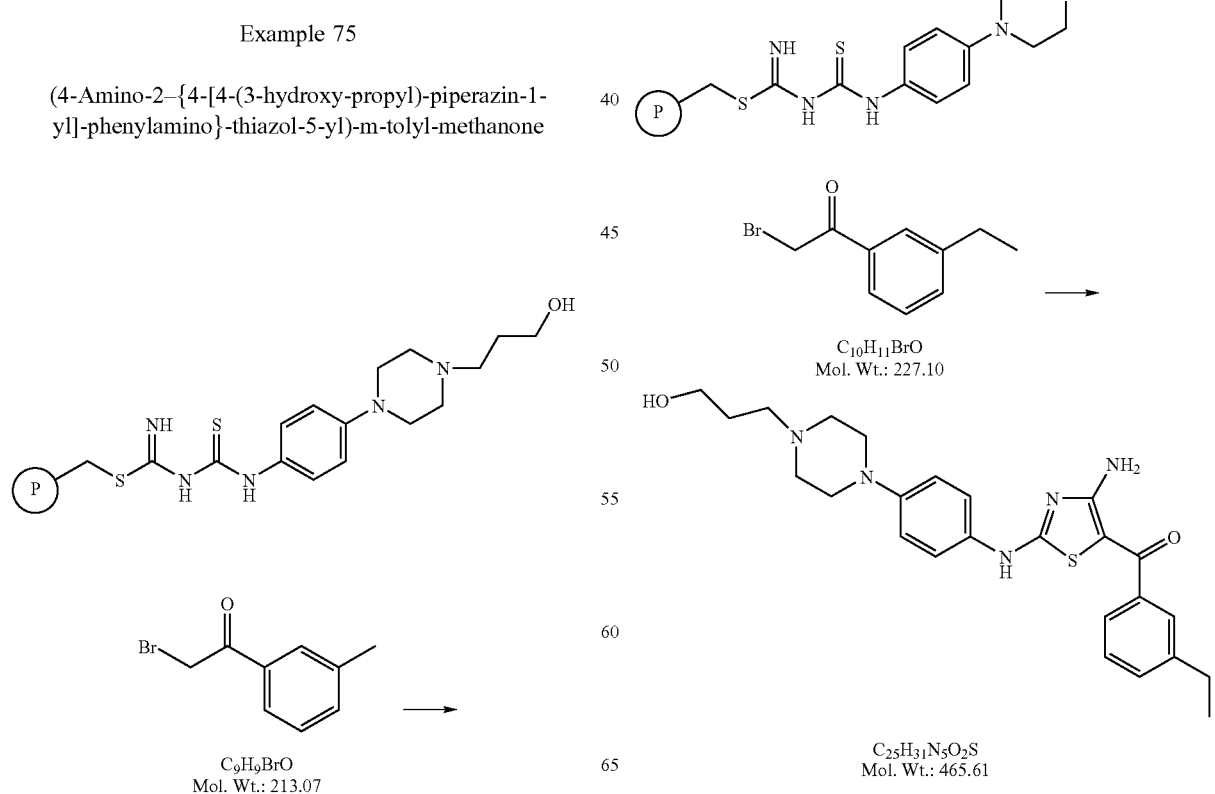

C₁₀H₁₁BrO
Mol. Wt.: 227.10

C₂₅H₃₁N₅O₂S
Mol. Wt.: 465.61

C₉H₉BrO
Mol. Wt.: 213.07

107

This compound was prepared from the resin-bound thiourea of Example 23F and 2-bromo-1-(3-ethylphenyl)ethanone (of Example 14O) by the procedure used in Example 27. Massspectrum (ES) MH⁺=466.

Example 77

{4-Amino-2-[4-(4-methyl-piperazin-1-yl)-phenylamino]-thiazol-5-yl}-(3-ethylphenyl)-methanone

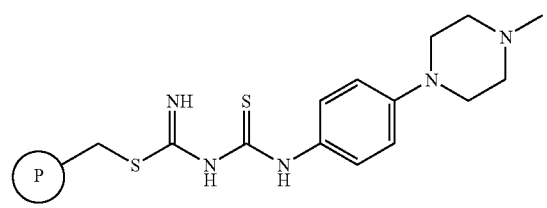

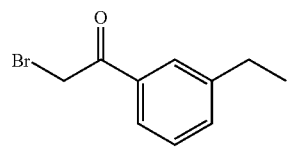

$C_{10}H_{11}BrO$
Mol. Wt.: 227.10

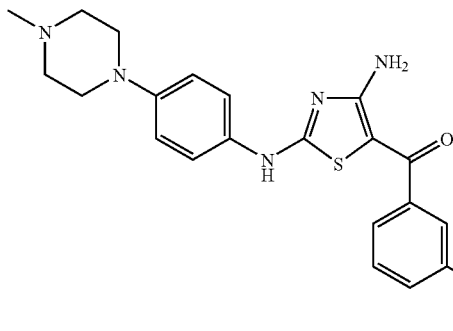

$C_{23}H_{27}N_5OS$
Mol. Wt.: 421.56

This compound was prepared from the resin-bound thiourea of Example 18 and 2-bromo-1-(3-ethylphenyl)ethanone (of Example 14O) by the procedure used in Example 27. Mass spectrum (ES) MH⁺=422.

Example 78

{4-Amino-2-[4-(4-methyl-piperazin-1-yl)-phenylamino]-thiazol-5-yl}-m-tolyl-methanone

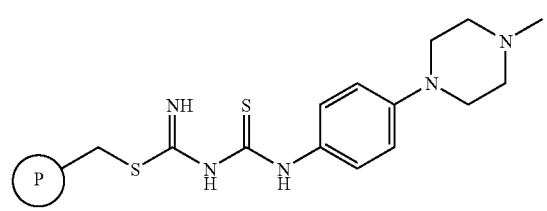

108

-continued

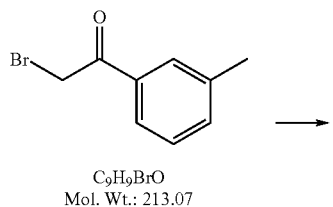

$C_9H_9BrO$
Mol. Wt.: 213.07

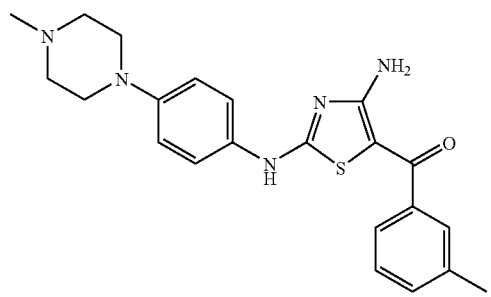

$C_{22}H_{25}N_5OS$
Mol. Wt.: 407.53

This compound was prepared from the resin-bound thiourea of Example 18 and 2-bromo-1-(3-methylphenyl)ethanone (which can be prepared by the procedure of Itoh, T. et al. EP 1020426) by the procedure used in Example 27. Mass spectrum (ES) MH⁺=408.

Example 79

3-{4-Amino-2-[4-(4-isopropyl-piperazin-1-yl)-phenylamino]-thiazole-5-carbonyl}-benzonitrile

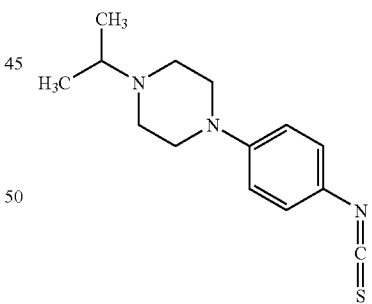

$C_{14}H_{19}N_3S$
MW 261.39

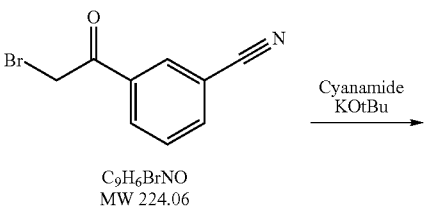

$C_9H_6BrNO$
MW 224.06

Cyanamide
KOtBu
→

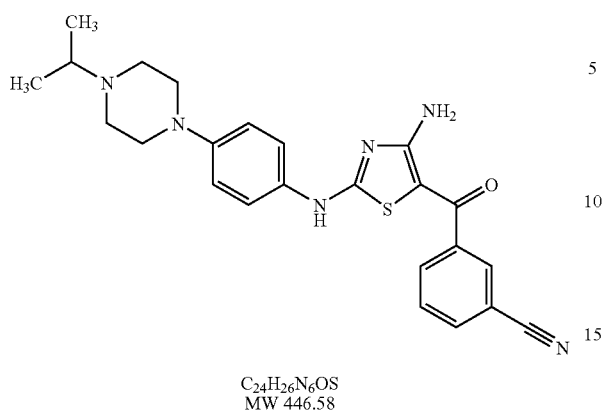

C₂₄H₂₆N₆OS
MW 446.58

This compound was prepared from cyanamide, 1-(4-isothiocyanatophenyl)-4-isopropypiperazine (of Example 3) and 3-cyanophenacyl bromide (Maybridge Chemical Co. Ltd.) following the procedure used in Example 24. Mass spectrum (ES) MH⁺=447.

Example 80

{4-Amino-2-[4-(4-isopropyl-piperazin-1-yl)-phenylamino]-thiazol-5-yl}-(3-fluoro-phenyl)-methanone (with hydrogen bromide)

This compound was prepared from the resin-bound thiourea of Example 20 and 2-bromo-1-(3-fluoro-phenyl)ethanone (Aldrich) by the procedure used in Example 27. Mass spectrum (ES) MH⁺=440.

Example 81

{4-Amino-2-[4-(4-isopropyl-piperazin-1-yl)-phenylamino]-thiazol-5-yl}-(3,4,5-trifluoro-phenyl)-methanone (with hydrogen bromide)

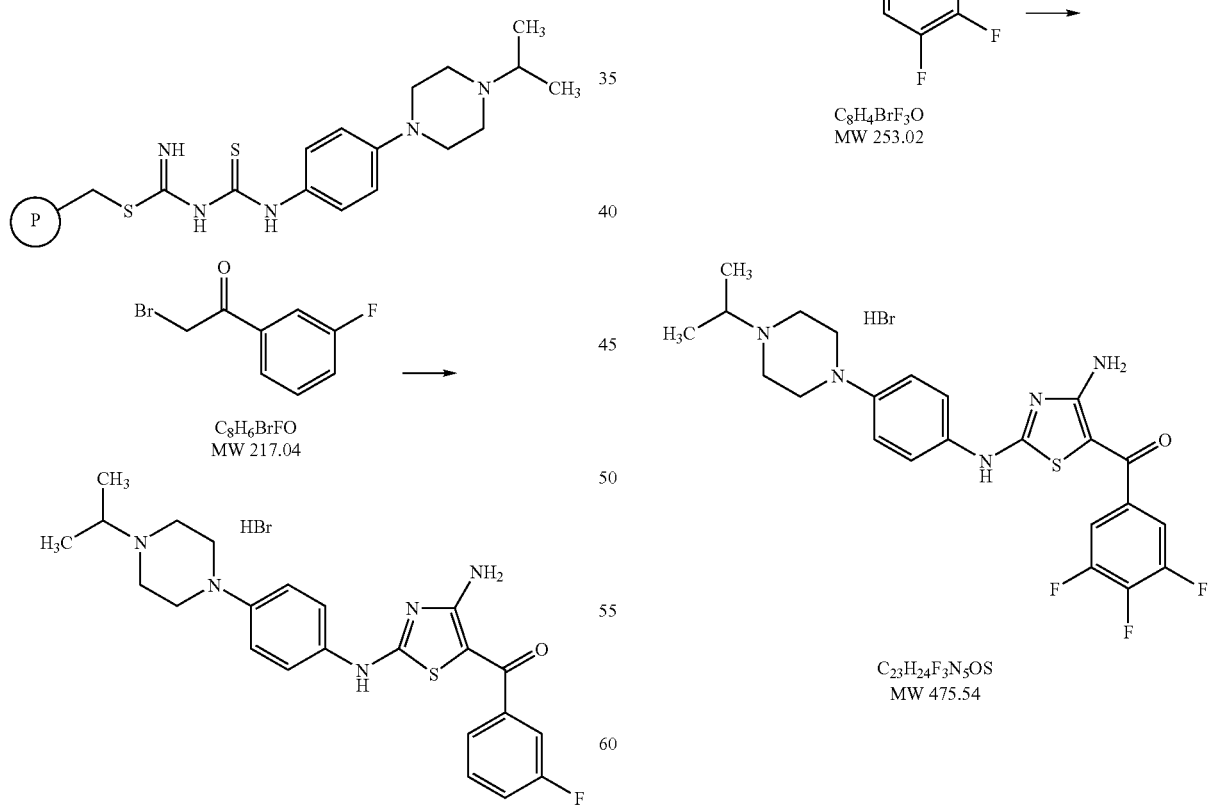

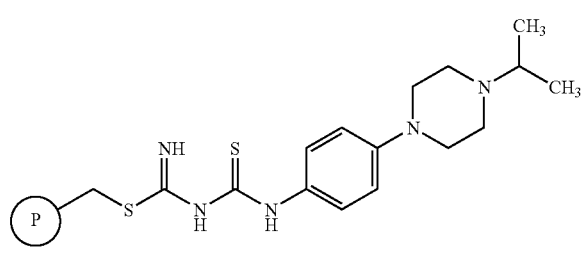

This compound was prepared from the resin-bound thiourea of Example 20 and 2-bromo-1-(3,4,5-trifluoro-phenyl)ethanone (of Example 14H) by the procedure used in Example 27. Mass spectrum (ES) MH⁺=476.

Example 82

{4-Amino-2-[4-(4-isopropyl-piperazin-1-yl)-phenylamino]-thiazol-5-yl}-(3,5-difluoro-phenyl)-methanone (with hydrogen bromide)

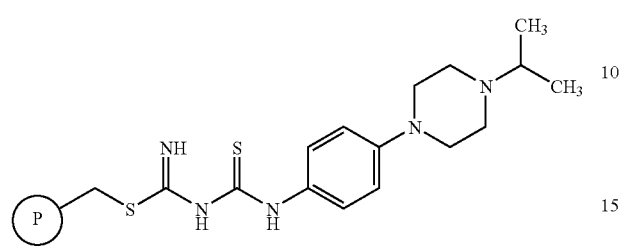

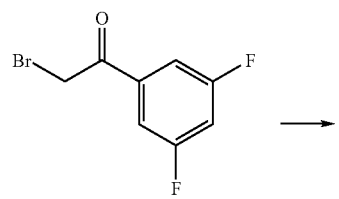

C$_8$H$_5$BrF$_2$O
MW 235.03

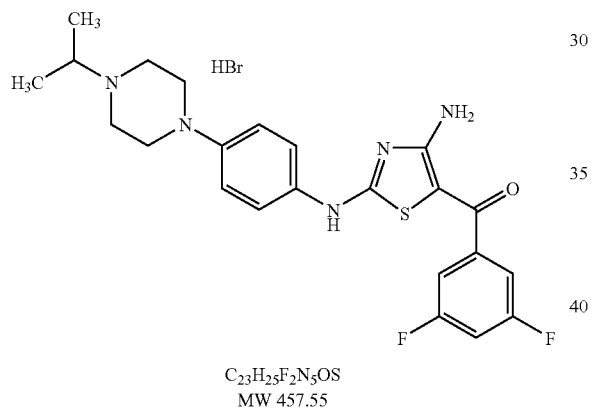

C$_{23}$H$_{25}$F$_2$N$_5$OS
MW 457.55

This compound was prepared from the resin-bound thiourea of Example 20 and 2-bromo-1-(3,5-difluorophenyl)ethanone (of Example 14A) by the procedure used in Example 27. Mass spectrum (ES) MH$^+$=458.

Example 83

4-Amino-2-{4-[4-(2-methoxy-ethyl)-piperazin-1-yl]-phenylamino}-thiazol-5-yl)-(3-fluoro-4-methoxy-phenyl)-methanone (with hydrogen bromide)

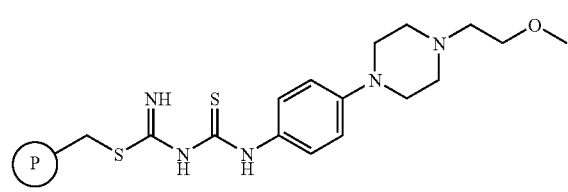

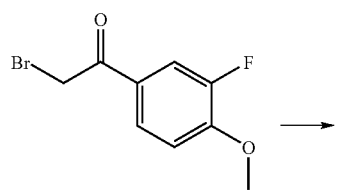

C$_9$H$_8$BrFO$_2$
MW 247.07

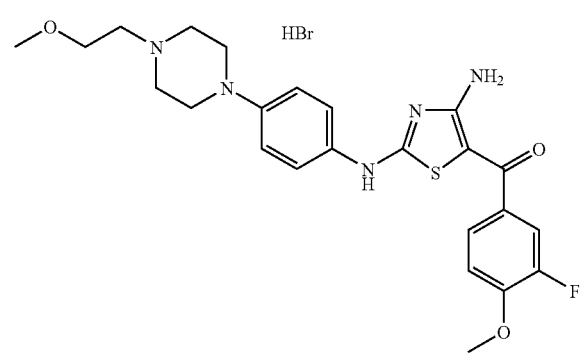

C$_{24}$H$_{28}$FN$_5$O$_3$S
MW 485.58

This compound was prepared from the resin-bound thiourea of Example 23B and 2-bromo-1-(3-fluoro-4-methoxyphenyl)ethanone (of Example 13) by the procedure used in Example 27. Mass spectrum (ES) MH$^+$=486.

Example 84

{4-Amino-2-[4-(4-isopropyl-piperazin-1-yl)-phenylamino]-thiazol-5-yl}-(4-fluoro-3-methoxy-phenyl)-methanone (with hydrogen bromide)

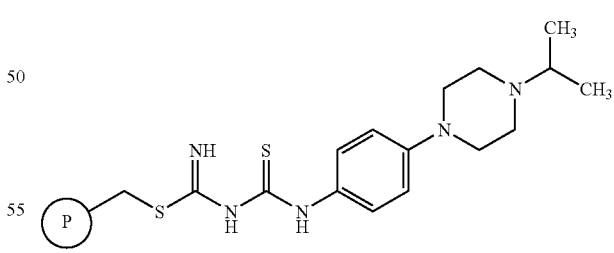

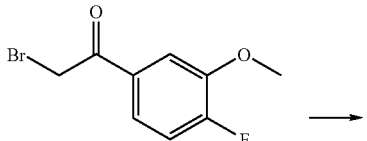

C$_9$H$_8$BrFO$_2$
MW 247.07

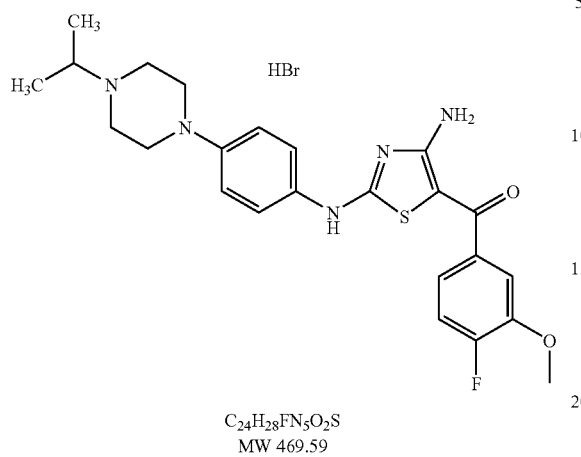

C₂₄H₂₈FN₅O₂S
MW 469.59

This compound was prepared from the resin-bound thiourea of Example 20 and 2-bromo-1-(4-fluoro-3-methoxyphenyl)ethanone (of Example 14I) by the procedure used in Example 27. Mass spectrum (ES) MH⁺=470.

Example 85

{4-Amino-2-[4-(4-isopropyl-piperazin-1-yl)-phenylamino]-thiazol-5-yl}-(3-fluoro-4-methoxy-phenyl)-methanone (with hydrogen bromide)

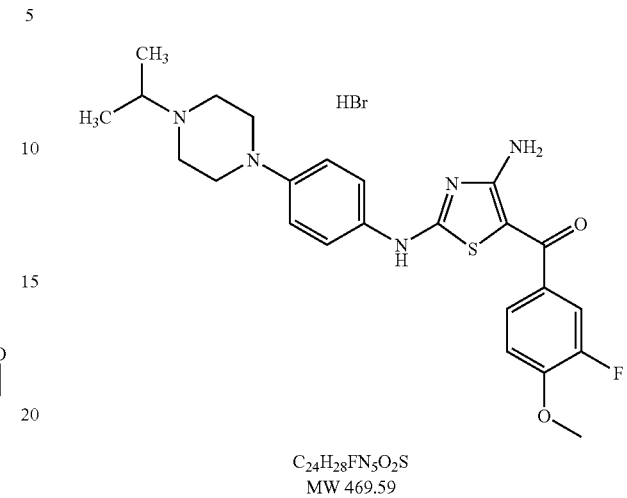

C₂₄H₂₈FN₅O₂S
MW 469.59

This compound was prepared from the resin-bound thiourea of Example 20 and 2-bromo-1-(3-fluoro-4-methoxyphenyl)ethanone (of Example 13) by the procedure used in Example 27. Mass spectrum (ES) MH⁺=470.

Example 86

{4-Amino-2-[4-(4-isopropyl-piperazin-1-yl)-phenylamino]-thiazol-5-yl}-(4-difluoromethoxy-phenyl)-methanone (with hydrogen bromide)

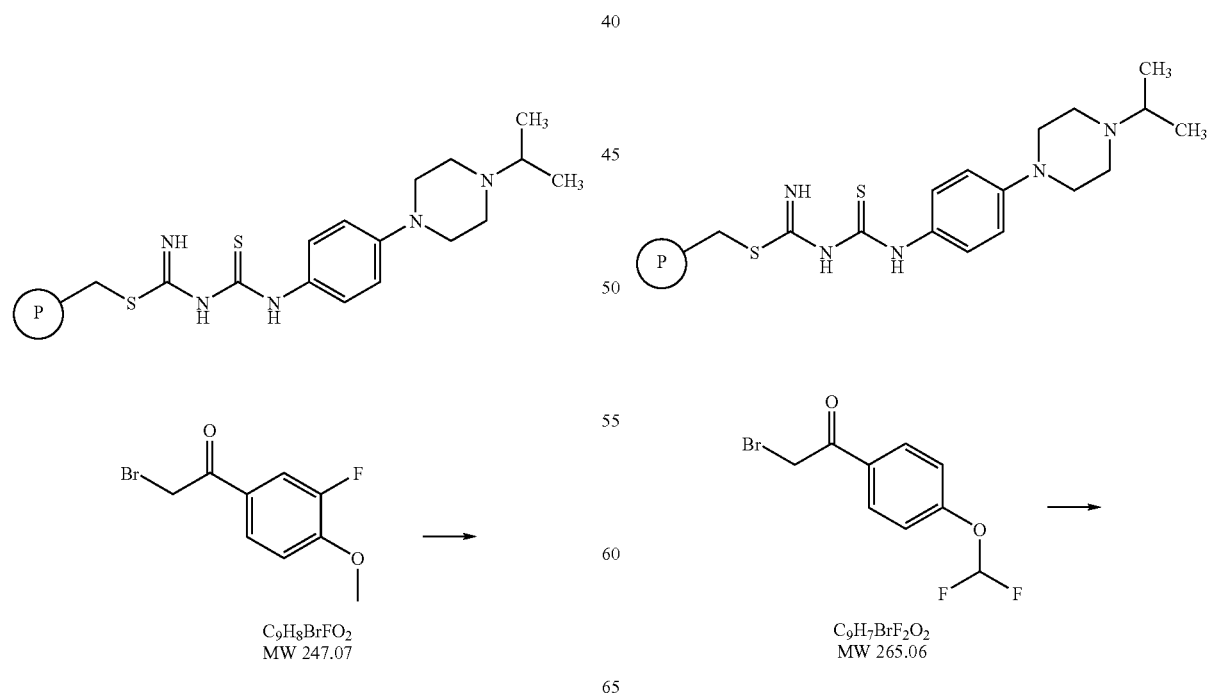

C₉H₈BrFO₂
MW 247.07

C₉H₇BrF₂O₂
MW 265.06

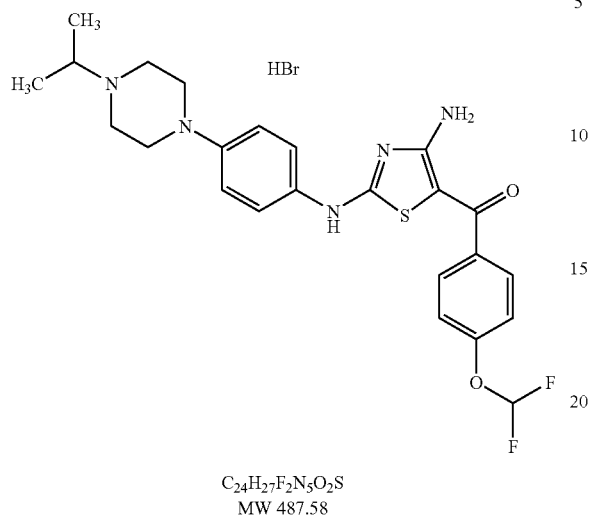

C₂₄H₂₇F₂N₅O₂S
MW 487.58

This compound was prepared from the resin-bound thiourea of Example 20 and 2-bromo-1-(4-difluoromethoxyphenyl)ethanone (Maybridge Chemical Company Ltd.) by the procedure used in Example 27. Mass spectrum (ES) MH⁺=488.

Example 87

{4-Amino-2-[4-(4-isopropyl-piperazin-1-yl)-phenylamino]-thiazol-5-yl}-(3-trifluoromethoxy-phenyl)-methanone (with hydrogen bromide)

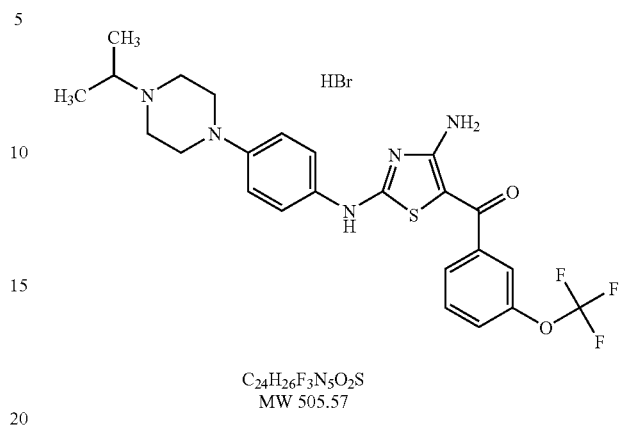

C₂₄H₂₆F₃N₅O₂S
MW 505.57

This compound was prepared from the resin-bound thiourea of Example 20 and 2-bromo-1-(3-trifluoromethoxyphenyl)ethanone (of Example 14J) by the procedure used in Example 27. Mass spectrum (ES) MH⁺=506.

Example 88

{4-Amino-2-[4-(4-isopropyl-piperazin-1-yl)-phenylamino]-thiazol-5-yl}-(4-piperidin-1-yl-phenyl)-methanone (with hydrogen bromide)

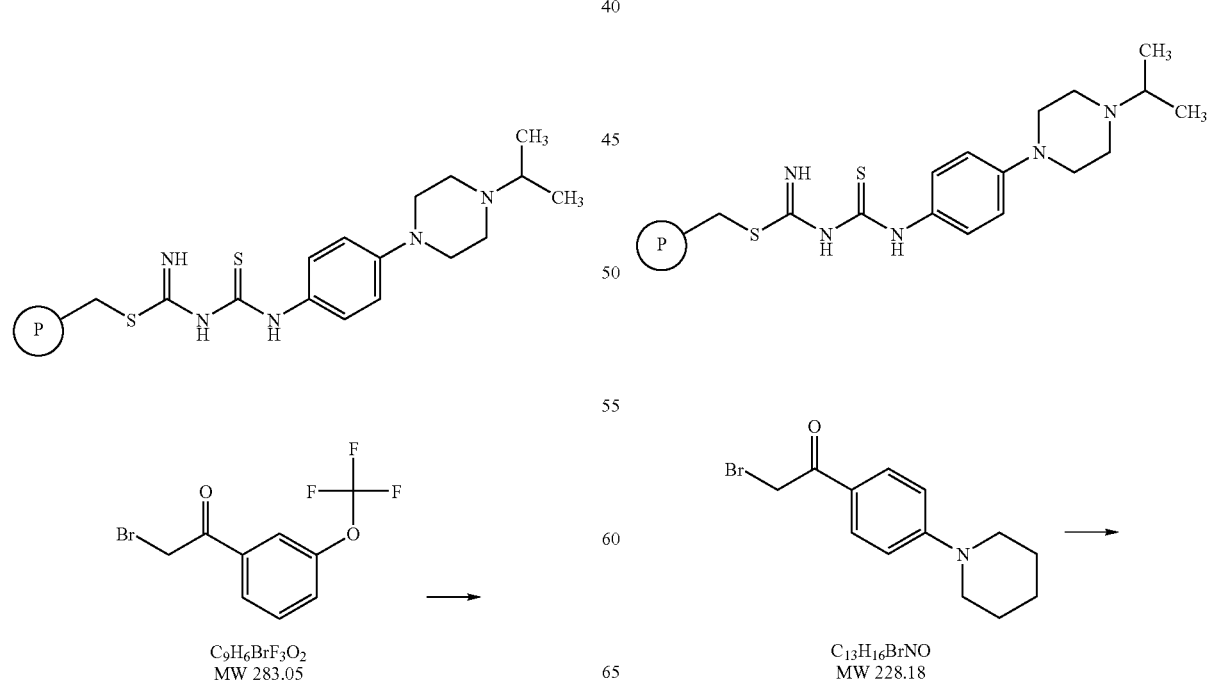

C₉H₆BrF₃O₂
MW 283.05

C₁₃H₁₆BrNO
MW 228.18

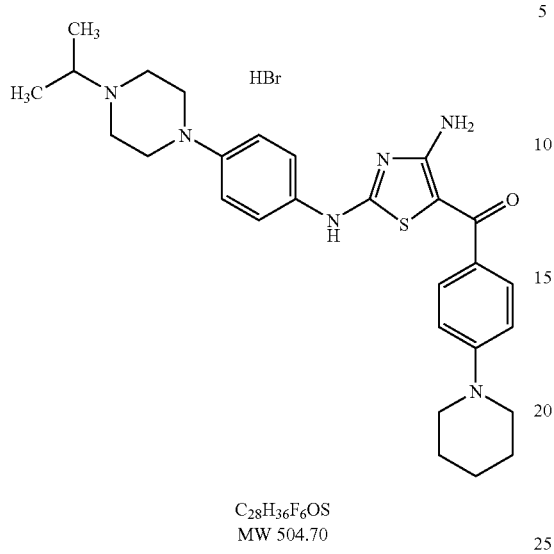

C₂₈H₃₆F₆OS
MW 504.70

This compound was prepared from the resin-bound thiourea of Example 20 and 2-bromo-1-(4-piperidin-1-yl-phenyl)ethanone (of Example 7) by the procedure used in Example 27. Mass spectrum (ES) MH⁺=505.

Example 89

{4-Amino-2-[4-(4-isopropyl-piperazin-1-yl)-phenylamino]-thiazol-5-yl}-(4-morpholin-4-yl-phenyl)-methanone (with hydrogen bromide)

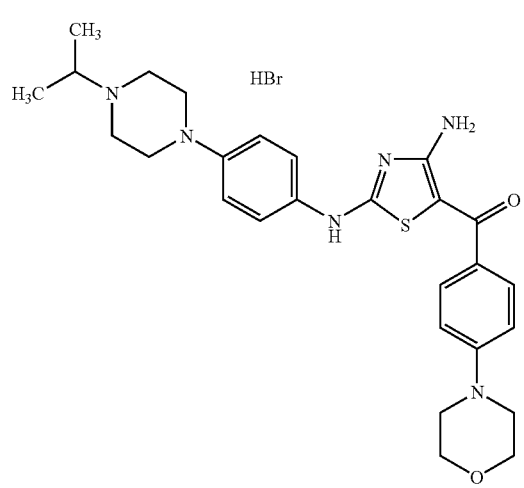

C₂₇H₃₄N₆O₂S
MW 506.68

This compound was prepared from the resin-bound thiourea of Example 20 and 2-bromo-1-(4-morpholin-4-phenyl)ethanone (of Example 8) by the procedure used in Example 27. Mass spectrum (ES) MH⁺=507.

Example 90

(4-Amino-2-{4-[4-(2-methoxy-ethyl)-piperazin-1-yl]-phenylamino}-thiazol-5-yl)-(3,5-difluoro-phenyl)-methanone (with hydrogen bromide)

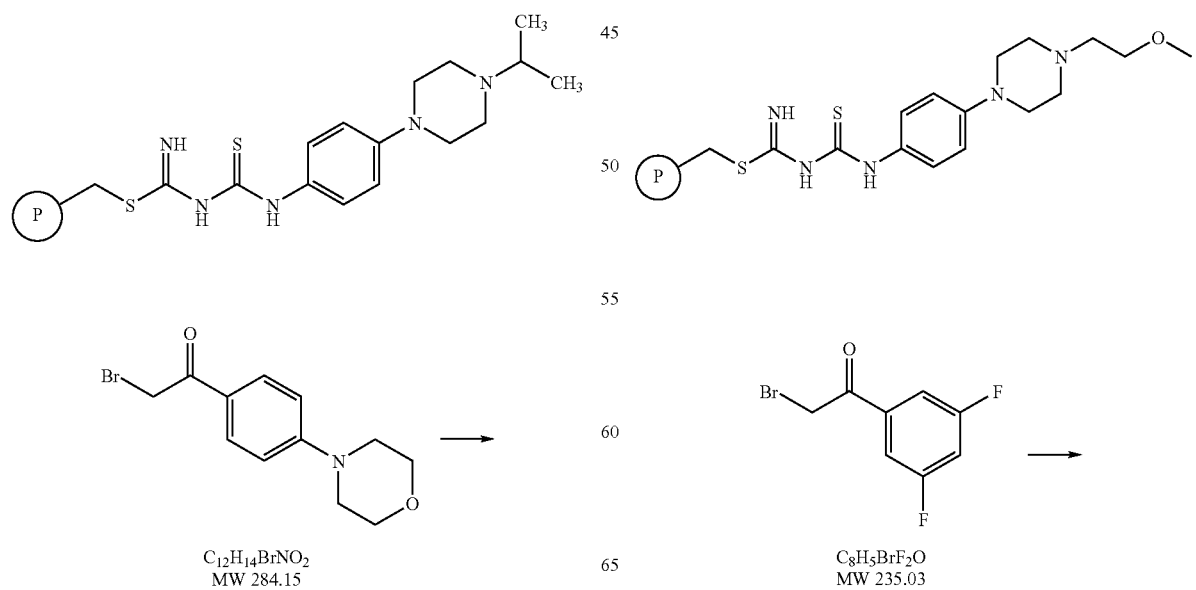

C₁₂H₁₄BrNO₂
MW 284.15

C₈H₅BrF₂O
MW 235.03

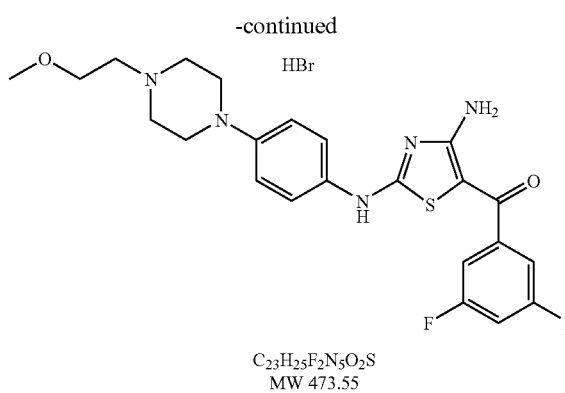

C₂₃H₂₅F₂N₅O₂S
MW 473.55

This compound was prepared from the resin-bound thiourea of Example 23B and 2-bromo-1-(3,5-difluorophenyl)ethanone (of Example 14A) by the procedure used in Example 27. Mass spectrum (ES) MH⁺=474.

Example 91

(4-Amino-2-{4-[4-(2-methoxy-ethyl)-piperazin-1-yl]-phenylamino}-thiazol-5-yl)-(3,4-difluoro-phenyl)-methanone (with hydrogen bromide)

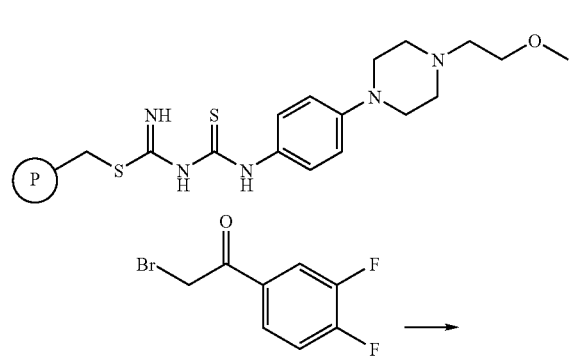

C₈H₅BrF₂O
MW 235.03

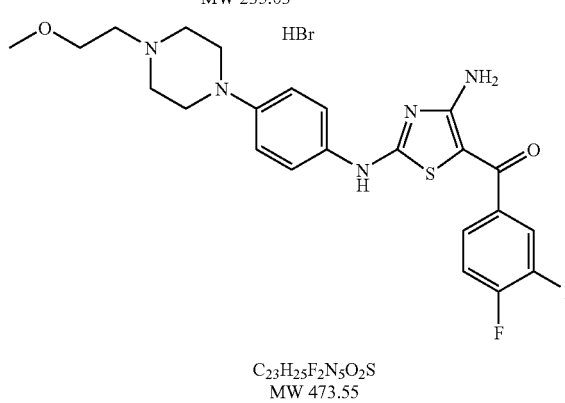

C₂₃H₂₅F₂N₅O₂S
MW 473.55

This compound was prepared from the resin-bound thiourea of Example 23B and 2-bromo-1-(3,4-difluorophenyl)ethanone (Maybridge Chem Co. Ltd.) by the procedure used in Example 27. Mass spectrum (ES) MH⁺=474.

Example 92

(4-Amino-2-{4-[4-(2-methoxy-ethyl)-piperazin-1-yl]-phenylamino}-thiazol-5-yl)-(3-methoxy-phenyl)-methanone (with hydrogen bromide)

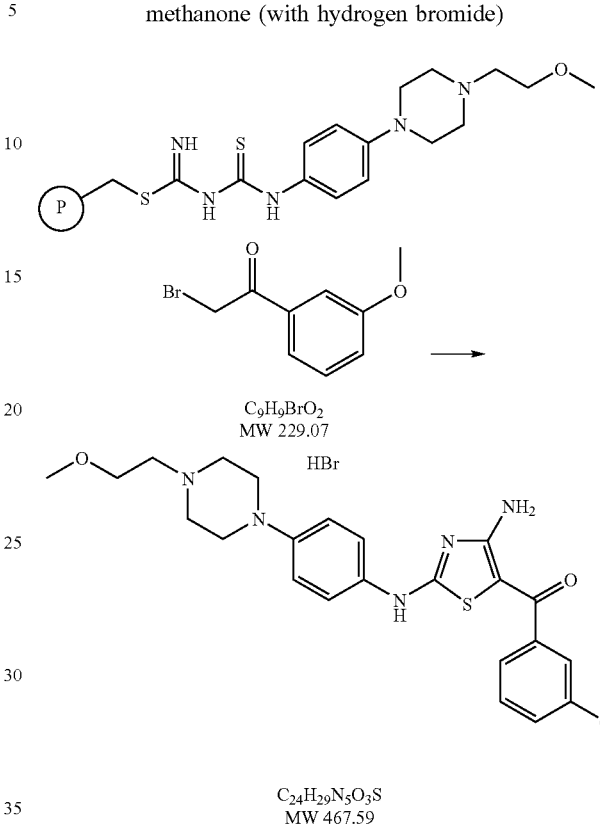

C₉H₉BrO₂
MW 229.07

C₂₄H₂₉N₅O₃S
MW 467.59

This compound was prepared from the resin-bound thiourea of Example 23B and 2-bromo-1-(3-methoxy)ethanone (Aldrich) by the procedure used in Example 27. Mass spectrum (ES) MH⁺=468.

Example 93

(4-Amino-2-{4-[4-(2-methoxy-ethyl)-piperazin-1-yl]-phenylamino}-thiazol-5-yl)-benzo[1,3]dioxol-5-yl-methanone (with hydrogen bromide)

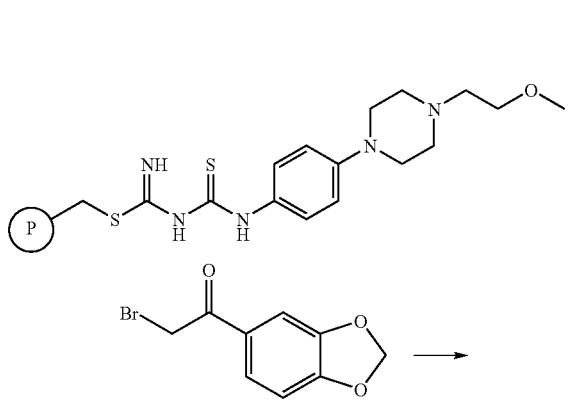

C₉H₇BrO₃
MW 243.06

-continued

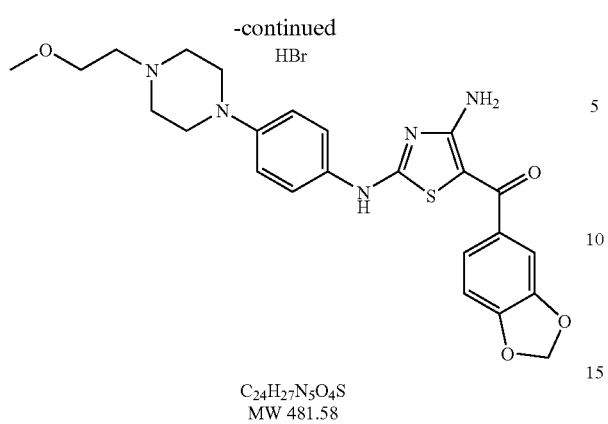

C₂₄H₂₇N₅O₄S
MW 481.58

This compound was prepared from the resin-bound thiourea of Example 23B and 2-bromo-1-(benzo[1,3]dioxol-5-yl)ethanone (of Example 11) by the procedure used in Example 27. Mass spectrum (ES) MH⁺=482.

Example 94

(4-Amino-2-{4-[4-(2-methoxy-ethyl)-piperazin-1-yl]-phenylamino}-thiazol-5-yl)-(2,3-dihydro-benzo[1,4]dioxin-6-yl)-methanone (with hydrogen bromide)

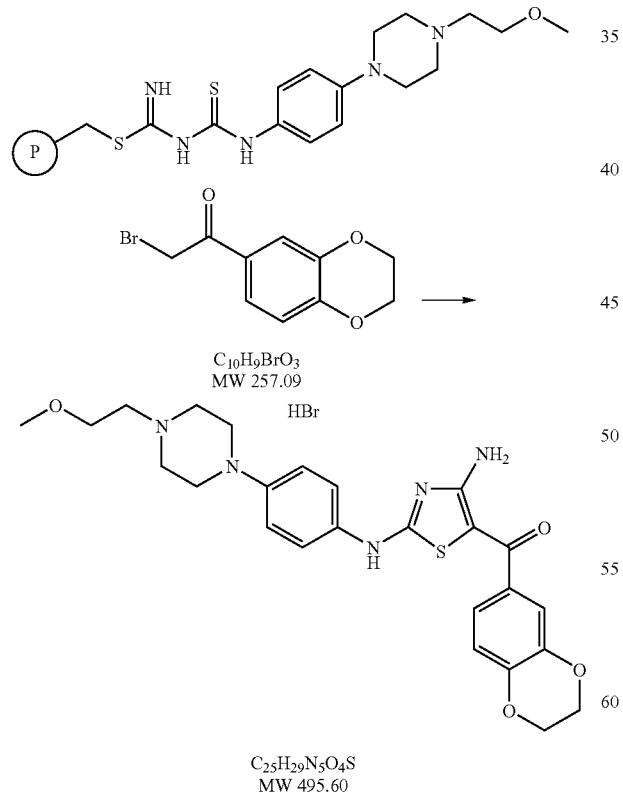

C₂₅H₂₉N₅O₄S
MW 495.60

This compound was prepared from the resin-bound thiourea of Example 23B and 2-bromo-1-(2,3-dihydro-benzo[1,4]dioxin-6-yl)ethanone (Maybridge Chem Co. Ltd.) by the procedure used in Example 27. Mass spectrum (ES) MH⁺=496.

Example 95

{4-Amino-2-[4-(4-methyl-piperazin-1-yl)-phenylamino]-thiazol-5-yl}-(3,5-difluoro-phenyl)-methanone (with hydrogen bromide)

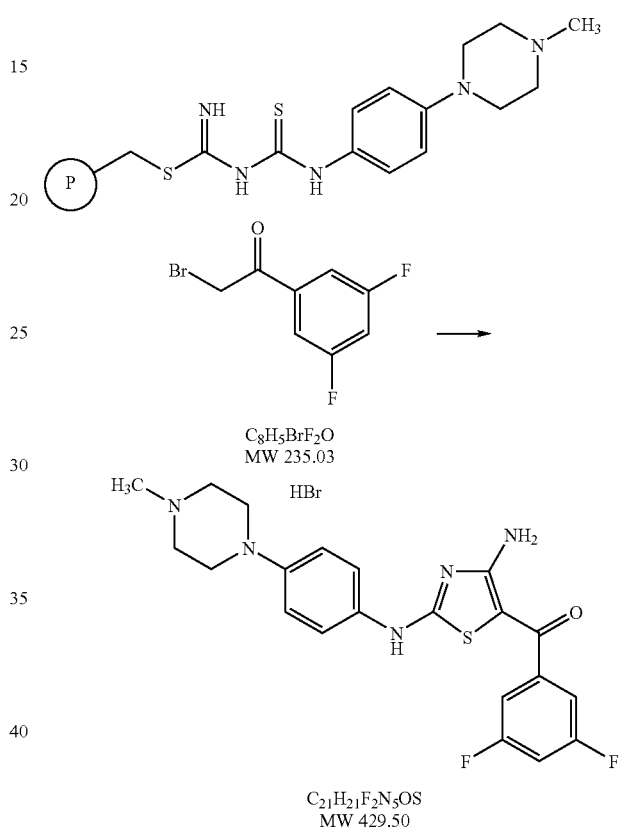

C₂₁H₂₁F₂N₅OS
MW 429.50

This compound was prepared from the resin-bound thiourea of Example 18 and 2-bromo-1-(3,5-difluorophenyl)ethanone (of Example 14A) by the procedure used in Example 27. Mass spectrum (ES) MH⁺=430.

Example 96

{4-Amino-2-[4-(4-methyl-piperazin-1-yl)-phenylamino]-thiazol-5-yl}-(3,5-difluoro-4-methoxy-phenyl)-methanone (with hydrogen bromide)

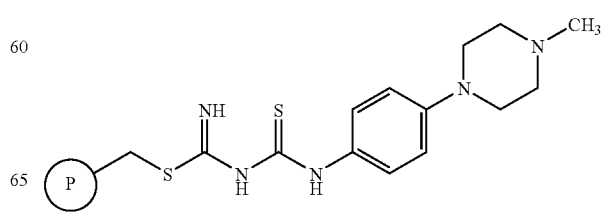

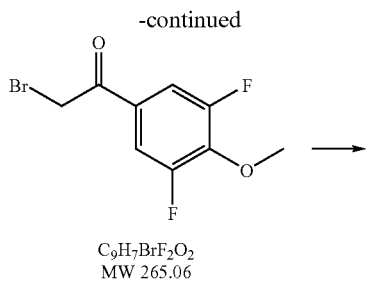

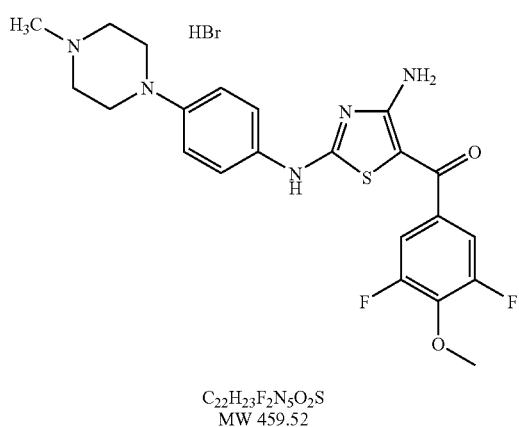

This compound was prepared from the resin-bound thiourea of Example 18 and 2-bromo-1-(3,5-difluoro-4-methoxy-phenyl)ethanone (of Example 14K) by the procedure used in Example 27. Mass spectrum (ES) MH+=460.

Example 97

{4-Amino-2-[4-(4-methyl-piperazin-1-yl)-phenylamino]-thiazol-5-yl}-(4-fluoro-3-methoxy-phenyl)-methanone (with hydrogen bromide)

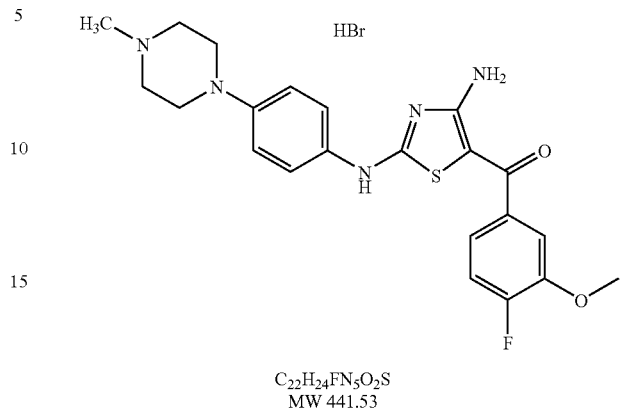

This compound was prepared from the resin-bound thiourea of Example 18 and 2-bromo-1-(4-fluoro-3-methoxy-phenyl)ethanone (of Example 14I) by the procedure used in Example 27. Mass spectrum (ES) MH+=442.

Example 98

{4-Amino-2-[4-(4-methyl-piperazin-1-yl)-phenylamino]-thiazol-5-yl}-(3-trifluoromethoxy-phenyl)-methanone (with hydrogen bromide)

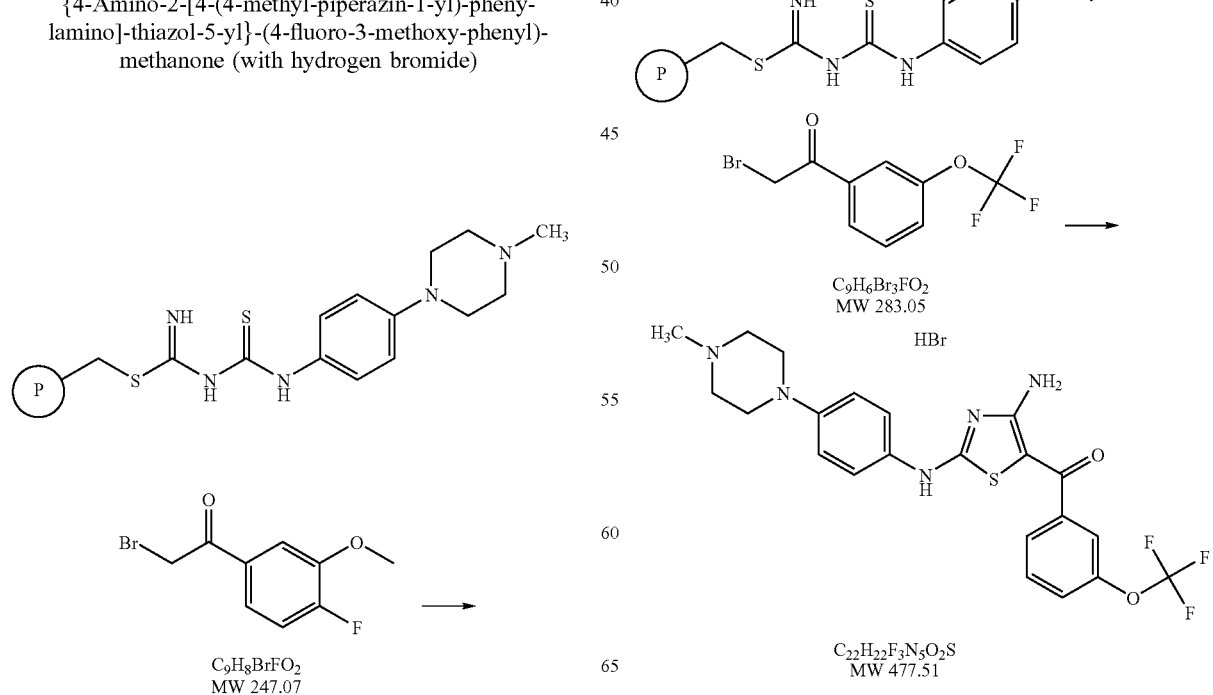

125

This compound was prepared from the resin-bound thiourea of Example 18 and 2-bromo-1-(3-trifluoromethoxyphenyl)ethanone (of Example 14J) by the procedure used in, Example 27. Mass spectrum (ES) MH+=478.

Example 99

(4-Amino-2-{4-[4-(2-hydroxy-ethyl)-piperazin-1-yl]-phenylamino}-thiazol-5-yl)-(3-fluoro-phenyl)-methanone (with acetic acid)

Example 100

[4-Amino-2-(4-piperazin-1-yl-phenylamino)-thiazol-5-yl]-(3,4,5-trifluorophenyl)-methanone (with acetic acid)

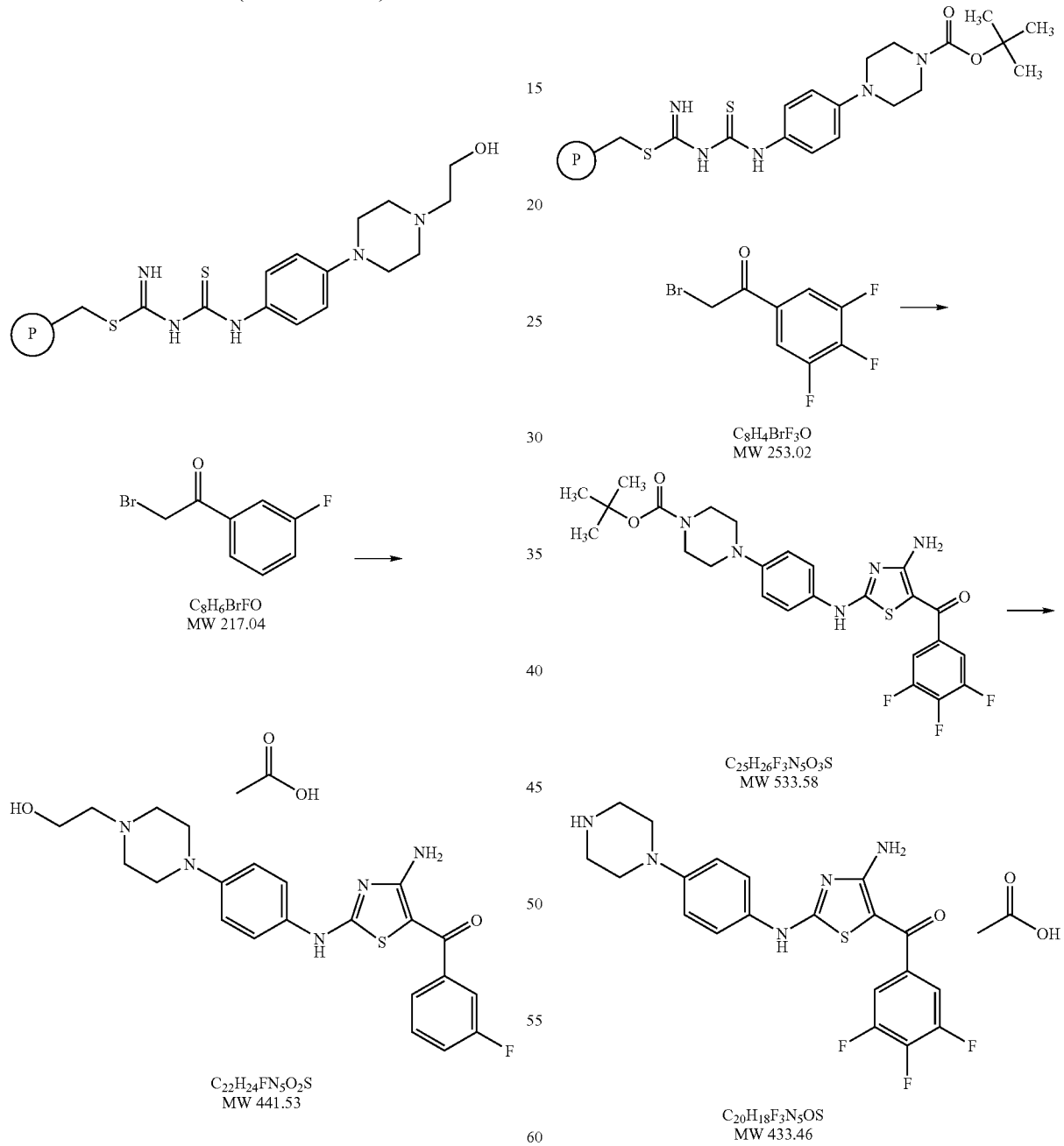

This compound was prepared from the resin-bound thiourea of Example 22 and 2-bromo-1-(3-fluoro-phenyl)ethanone (Aldrich) by the procedure used in Example 27. The crude product was purified by HPLC as described in Example 28. Mass spectrum (ES) MH+=442.

This compound was prepared from the resin-bound thiourea of Example 23A and 2-bromo-1-(3,4,5-trifluoro-phenyl)ethanone (of Example 14H) by the procedures used in Example 54. The crude product was purified by HPLC as described in Example 28. Mass spectrum (ES) MH+=434.

Example 101

[4-Amino-2-(4-piperazin-1-yl-phenylamino)-thiazol-5-yl]-(3,5-difluoro-4-methoxy-phenyl)-methanone (with acetic acid)

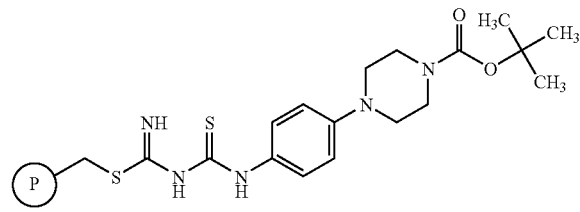

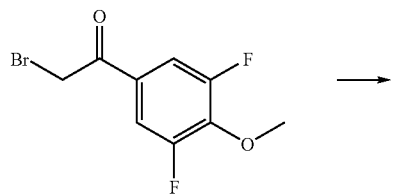

C₉H₇BrF₂O₂
MW 265.06

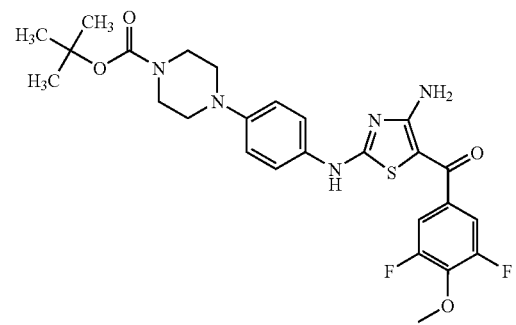

C₂₆H₂₉F₂N₅O₄S
MW 545.61

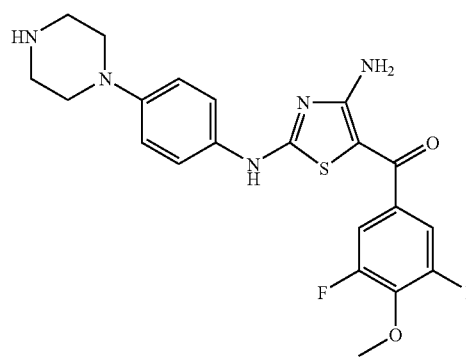

C₂₁H₂₁F₂N₅O₂S
MW 445.49

This compound was prepared from the resin-bound thiourea of Example 23A and 2-bromo-1-(3,5-difluoro-4-methoxy-phenyl)ethanone (of Example 14K) by the procedures used in Example 54. The crude product was purified by HPLC as described in Example 28. Mass spectrum (ES) MH⁺=446.

Example 102

[4-Amino-2-(4-piperazin-1-yl-phenylamino)-thiazol-5-yl]-(4-fluoro-3-methoxy-phenyl)-methanone (with acetic acid)

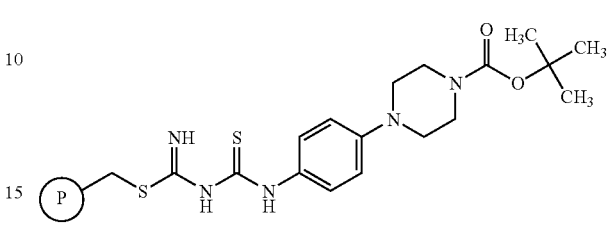

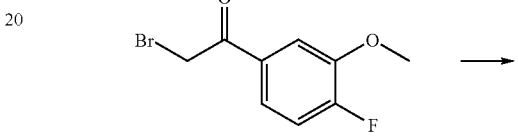

C₉H₈BrFO₂
MW 247.07

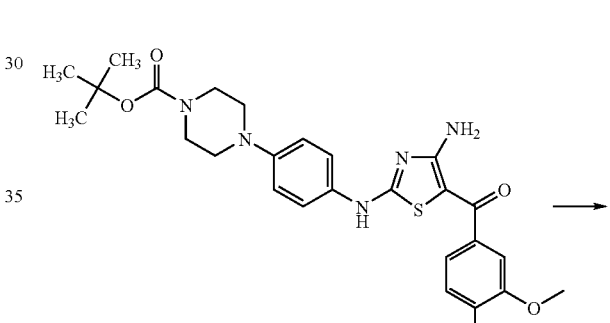

C₂₆H₃₀FN₅O₄S
MW 527.62

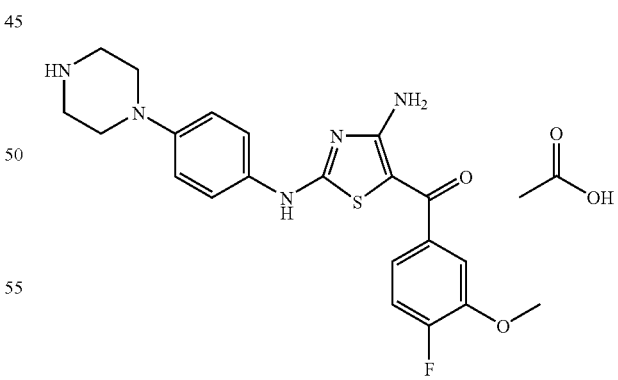

C₂₁H₂₂FN₅O₂S
MW 427.62

This compound was prepared from the resin-bound thiourea of Example 23A and 2-bromo-1-(4-fluoro-3-methoxy-phenyl)ethanone (of Example 14I) by the procedures used in Example 54. The crude product was purified by HPLC as described in Example 28. Mass spectrum (ES) MH⁺=428.

Example 103

[4-Amino-2-(4-piperazin-1-yl-phenylamino)-thiazol-5-yl]-(3-trifluoromethoxy-phenyl)-methanone (with acetic acid)

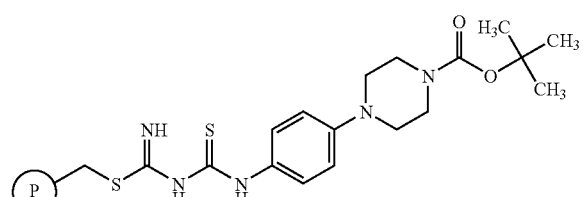

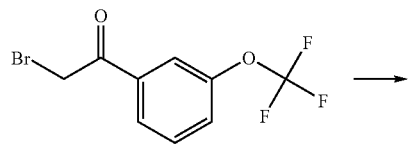

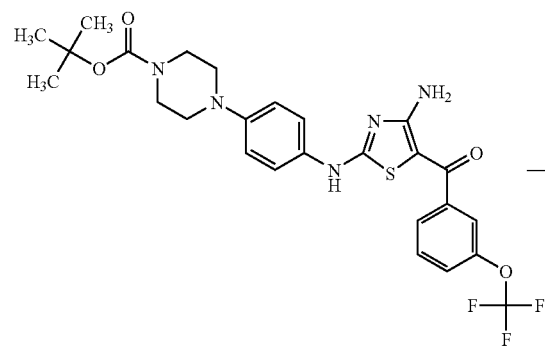

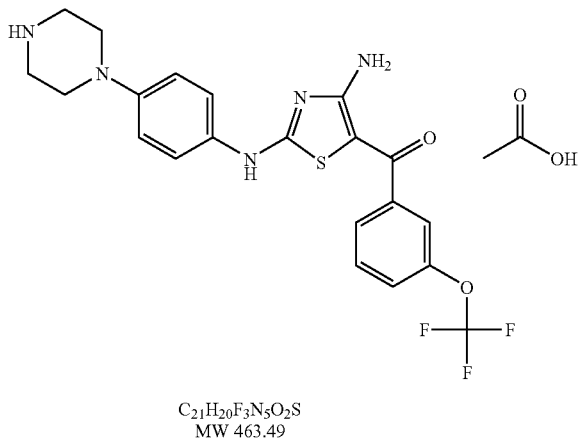

This compound was prepared from the resin-bound thiourea of Example 23A and 2-bromo-1-(3-trifluoromethoxy-phenyl)ethanone (of Example 14J) by the procedures used in Example 54. The crude product was purified by HPLC as described in Example 28. Mass spectrum (ES) MH$^+$=464.

Example 104

{4-Amino-2-[4-(4-sec-butyl-piperazin-1-yl)-phenylamino]-thiazol-5-yl}-(3-fluoro-phenyl)-methanone

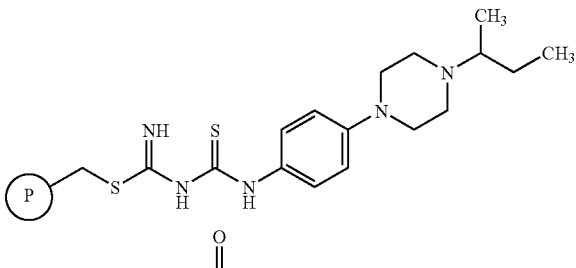

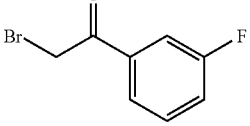

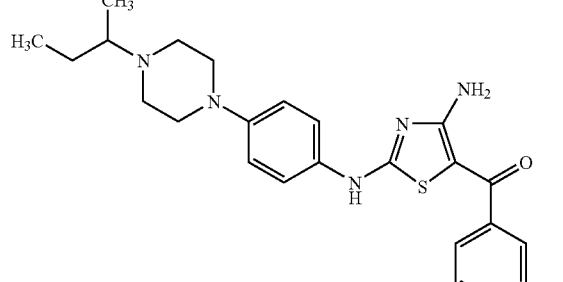

This compound was prepared from the resin-bound thiourea of Example 23C and 2-bromo-1-(3-fluoro-phenyl)ethanone (Aldrich) by the procedure used in Example 27. Mass spectrum (ES) MH$^+$=454.

Example 105

{4-Amino-2-[4-(4-sec-butyl-piperazin-1-yl)-phenylamino]-thiazol-5-yl}-benzo[1,3]dioxol-5-yl-methanone

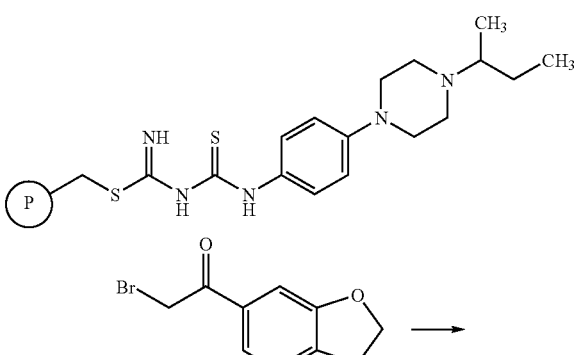

131

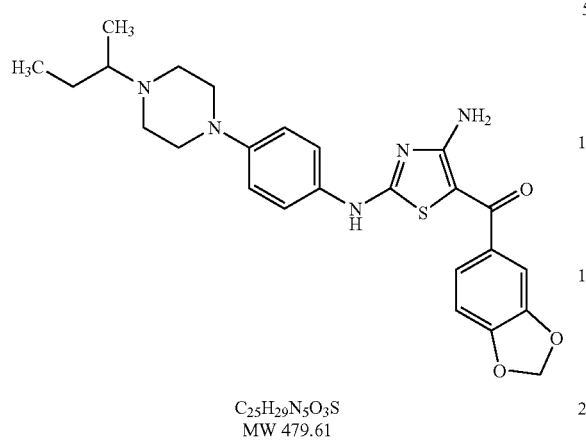

C₂₅H₂₉N₅O₃S
MW 479.61

This compound was prepared from the resin-bound thiourea of Example 23C and 2-bromo-1-(benzo[1,3]dioxol-5-yl)ethanone (of Example 11) by the procedure used in Example 27. Mass spectrum (ES) MH⁺=480.

Example 106

{4-Amino-2-[4-(4-sec-butyl-piperazin-1-yl)-phenylamino]-thiazol-5-yl}-(2,3-dihydro-benzo[1,4]dioxin-6-yl)-methanone

132

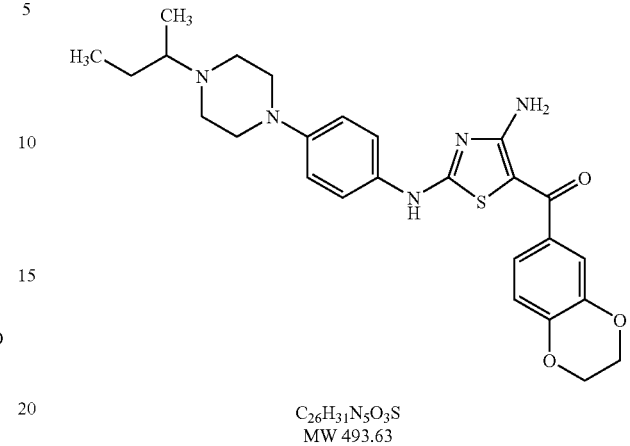

C₂₆H₃₁N₅O₃S
MW 493.63

This compound was prepared from the resin-bound thiourea of Example 23C and 2-bromo-1-(2,3-dihydro-benzo[1,4]dioxin-6-yl)ethanone (Maybridge Chem Co. Ltd.) by the procedure used in Example 27. Mass spectrum (ES). MH⁺=494.

Example 107

{4-Amino-2-[4-(4-cyclopentyl-piperazin-1-yl)-phenylamino]-thiazol-5-yl}-benzo[1,3]dioxol-5-yl-methanone

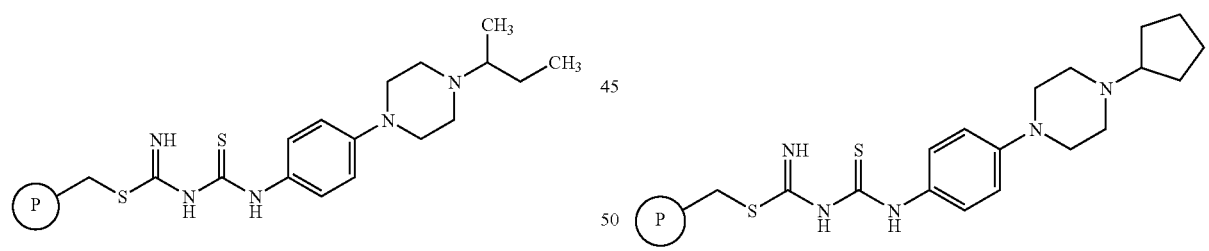

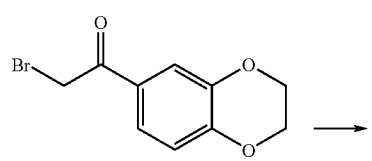

C₁₀H₉BrO₃
MW 257.09

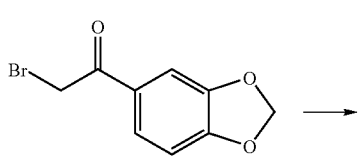

C₉H₇BrO₃
MW 243.06

-continued

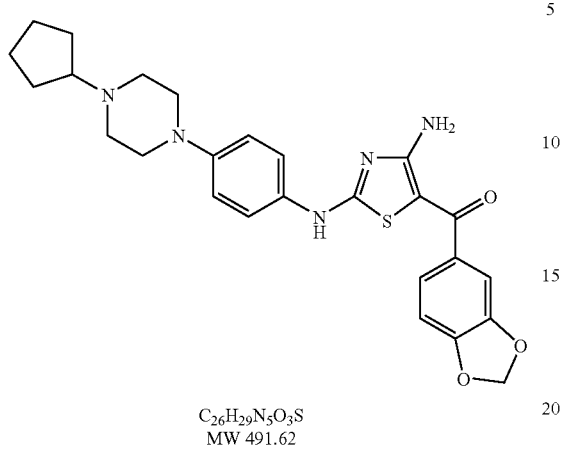

C$_{26}$H$_{29}$N$_5$O$_3$S
MW 491.62

This compound was prepared from the resin-bound thiourea of Example 23D and 2-bromo-1-(benzo[1,3]dioxol-5-yl)ethanone (of Example 11) by the procedure used in Example 27. Mass spectrum (ES) MH$^+$=492.

Example 108

{4-Amino-2-[4-(4-cyclopentyl-piperazin-1-yl)-phenylamino]-thiazol-5-yl}-(2,3-dihydro-benzo[1,4]dioxin-6-yl)-methanone

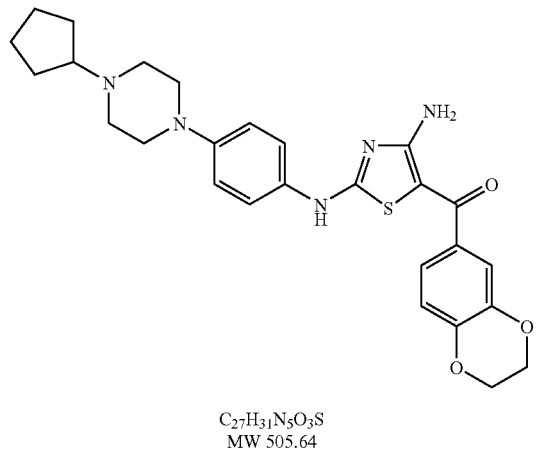

C$_{27}$H$_{31}$N$_5$O$_3$S
MW 505.64

This compound was prepared from the resin-bound thiourea of Example 23D and 2-bromo-1-(2,3-dihydro-benzo[1,4]dioxin-6-yl)ethanone (Maybridge Chem Co. Ltd) by the procedure used in Example 27. Mass spectrum (ES) MH$^+$=506.

Example 109

{4-Amino-2-[4-(4-isopropyl-piperazin-1-yl)-phenylamino]-thiazol-5-yl}-(3-trifluoromethoxy-phenyl)-methanone

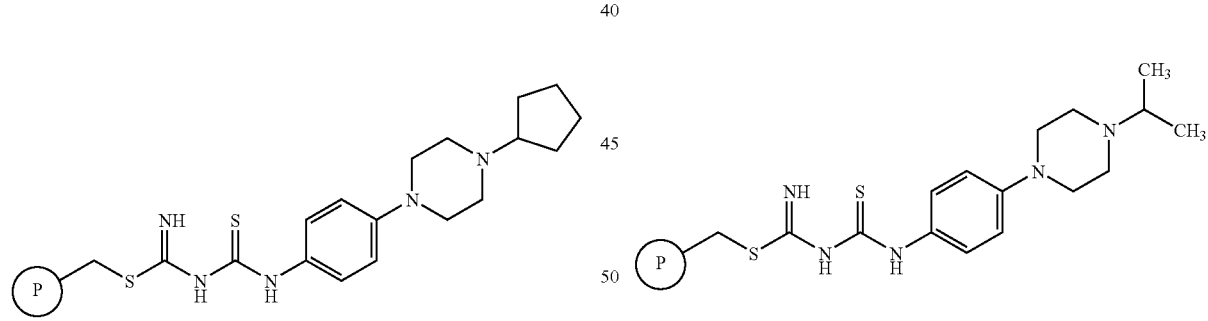

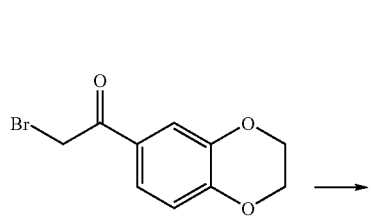

C$_{10}$H$_9$BrO$_3$
MW 257.09

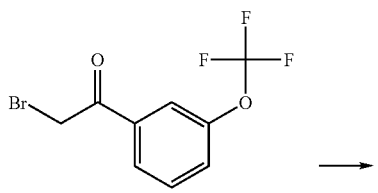

C$_9$H$_6$BrF$_3$O$_2$
MW 283.05

-continued

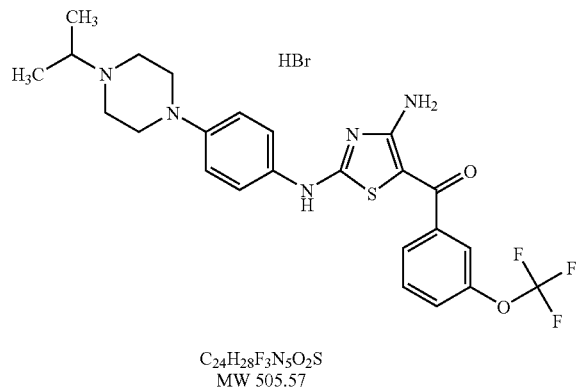

C$_{24}$H$_{28}$F$_3$N$_5$O$_2$S
MW 505.57

This compound was prepared from the resin-bound thiourea of Example 20 and 2-bromo-1-(3-trifluoromethoxyphenyl)ethanone (of Example 14J) by the procedure used in Example 27. Mass spectrum (ES) MH$^+$=506.

Example 110

{4-Amino-2-[4-(4-isopropyl-piperazin-1-yl)-phenylamino]-thiazol-5-yl}-(3-fluoro-phenyl)-methanone

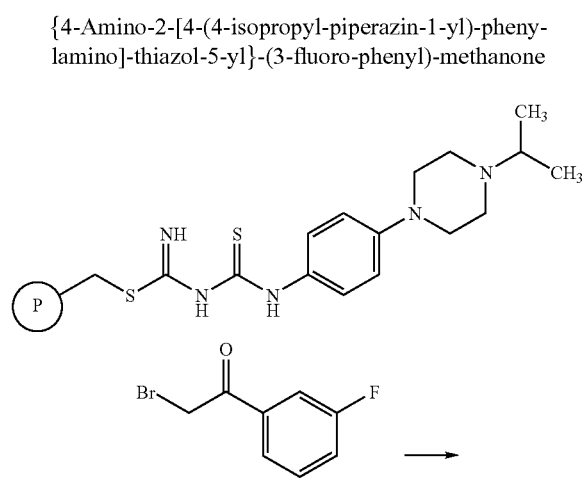

C$_8$H$_6$BrFO
MW 217.04

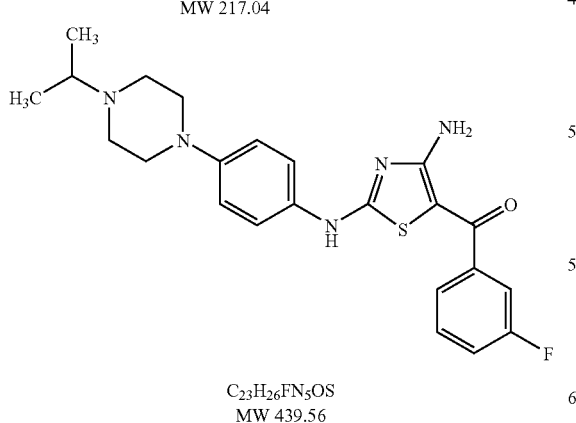

C$_{23}$H$_{26}$FN$_5$OS
MW 439.56

This compound was prepared from the resin-bound thiourea of Example 20 and 2-bromo-1-(3-fluoro-phenyl)ethanone (Aldrich) by the procedure used in Example 27. Mass spectrum (ES) MH$^+$=440.

Example 111

{4-Amino-2-[4-(4-isopropyl-piperazin-1-yl)-phenylamino]-thiazol-5-yl}-(3-difluoromethoxy-phenyl)-methanone

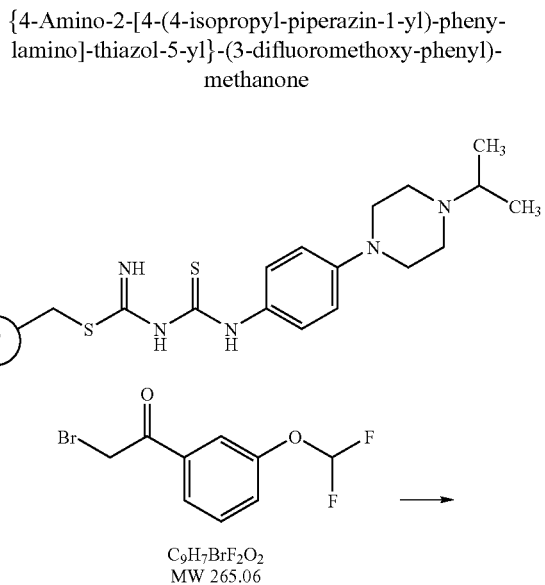

C$_9$H$_7$BrF$_2$O$_2$
MW 265.06

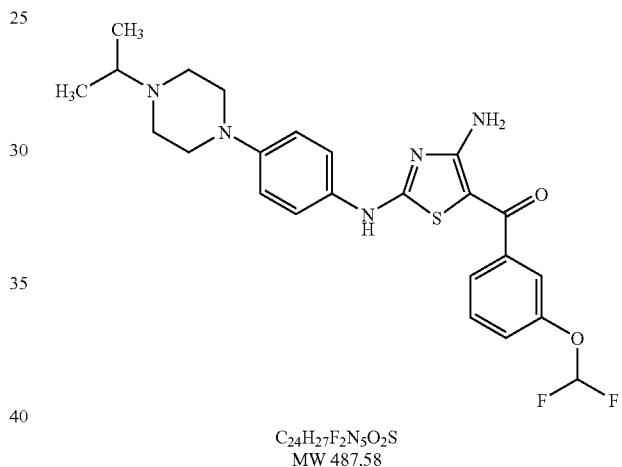

C$_{24}$H$_{27}$F$_2$N$_5$O$_2$S
MW 487.58

This compound was prepared from the resin-bound thiourea of Example 20 and 2-bromo-1-(3-difluoromethoxyphenyl)ethanone (of Example 14L) by the procedure used in Example 27. Mass spectrum (ES) MH$^+$=488.

Example 112

{4-Amino-2-[4-(4-isopropyl-piperazin-1-yl)-phenylamino]-thiazol-5-yl}-(3-hydroxy-phenyl)-methanone (with acetic acid)

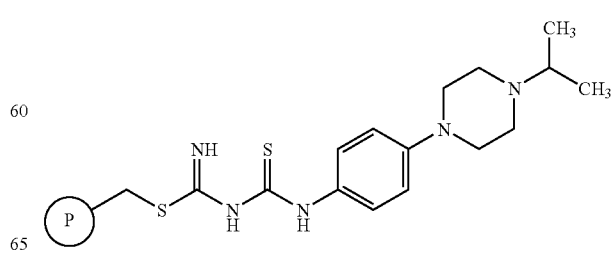

-continued

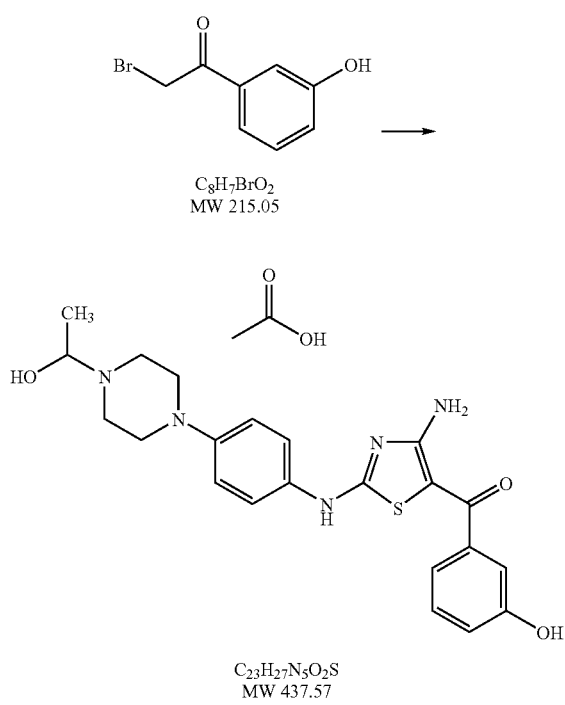

This compound was prepared from the resin-bound thiourea of Example 20 and 2-bromo-1-(3-hydroxy-phenyl)ethanone (of Example 14N) by the procedure used in Example 27. The crude product was purified by HPLC as described in Example 28. Mass spectrum (ES) MH+=438.

Example 113

{4-Amino-2-[4-(4-isobutyl-piperazin-1-yl)-phenylamino]-thiazol-5-yl}-(3-hydroxy-phenyl)-methanone (with acetic acid)

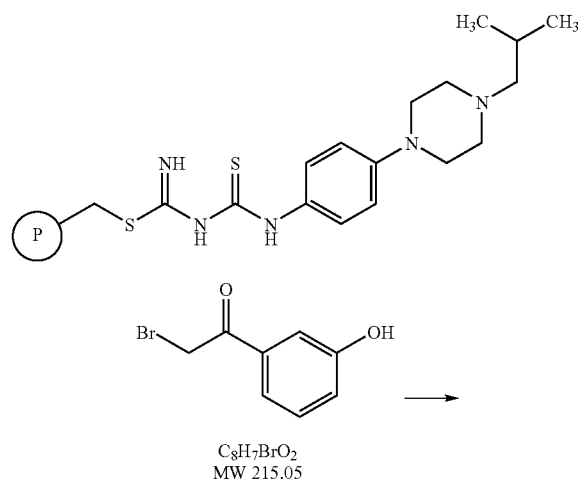

-continued

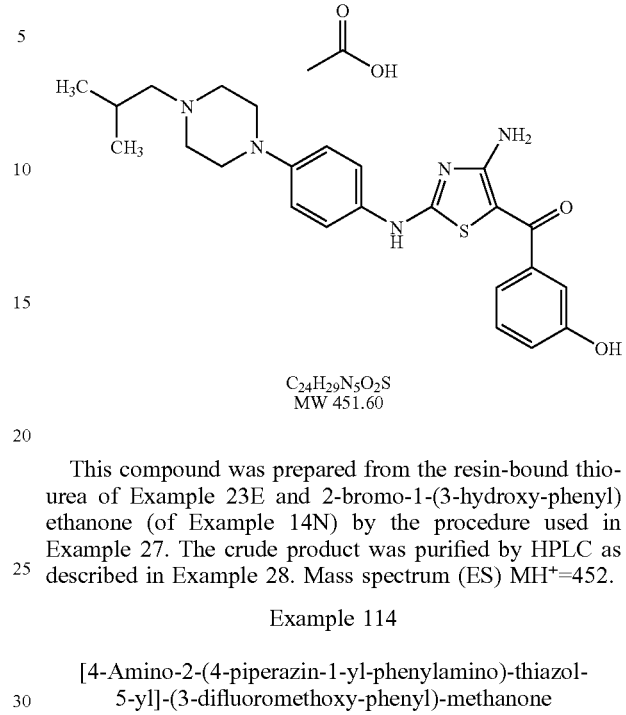

This compound was prepared from the resin-bound thiourea of Example 23E and 2-bromo-1-(3-hydroxy-phenyl)ethanone (of Example 14N) by the procedure used in Example 27. The crude product was purified by HPLC as described in Example 28. Mass spectrum (ES) MH+=452.

Example 114

[4-Amino-2-(4-piperazin-1-yl-phenylamino)-thiazol-5-yl]-(3-difluoromethoxy-phenyl)-methanone

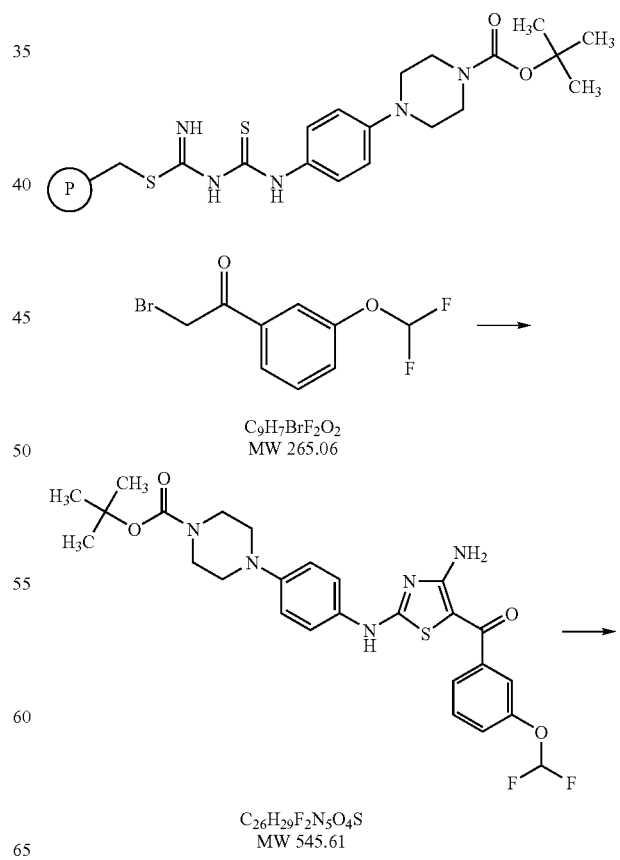

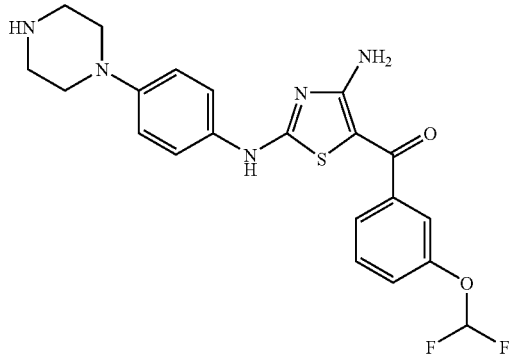

C₂₁H₂₁F₂N₅O₂S
MW 445.49

This compound was prepared from the resin-bound thio-urea of Example 23A and 2-bromo-1-(3-difluoromethoxy-phenyl)ethanone (of Example 14L) by the procedures used in Example 54. Mass spectrum (ES) MH⁺=446.

Example 115

{4-Amino-2-[4-(4-cyclopropylmethyl-piperazin-1-yl)-phenylamino]-thiazol-5-yl}-(3-difluoromethoxy-phenyl)-methanone

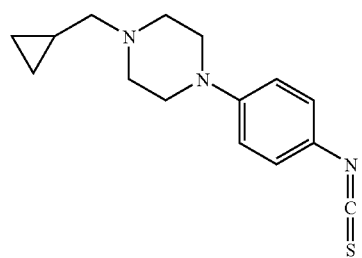

C₁₅H₁₉N₃S
MW 273.40

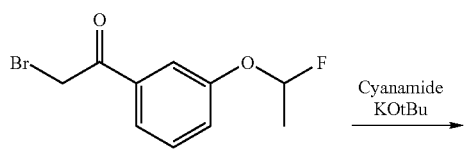

C₉H₇BrF₂O₂
MW 265.06

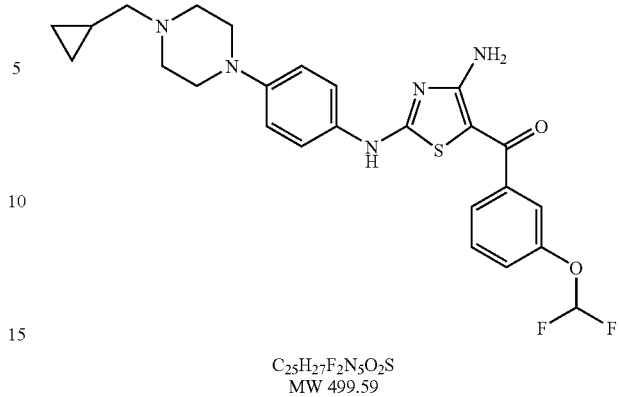

C₂₅H₂₇F₂N₅O₂S
MW 499.59

This compound was prepared from cyanamide, 1-(4-isothiocyanato-phenyl)-4-cyclopropylmethylpiperazine (of Example 14G) and 2-bromo-1-(3-difluoro-methoxyphenyl)ethanone (of Example 14L) following the procedure used in Example 24. Mass spectrum (ES) MH⁺=500.

Example 116

{4-Amino-2-[4-(4-cyclopropylmethyl-piperazin-1-yl)-phenylamino]-thiazol-5-yl}-(3-methoxy-phenyl)-methanone

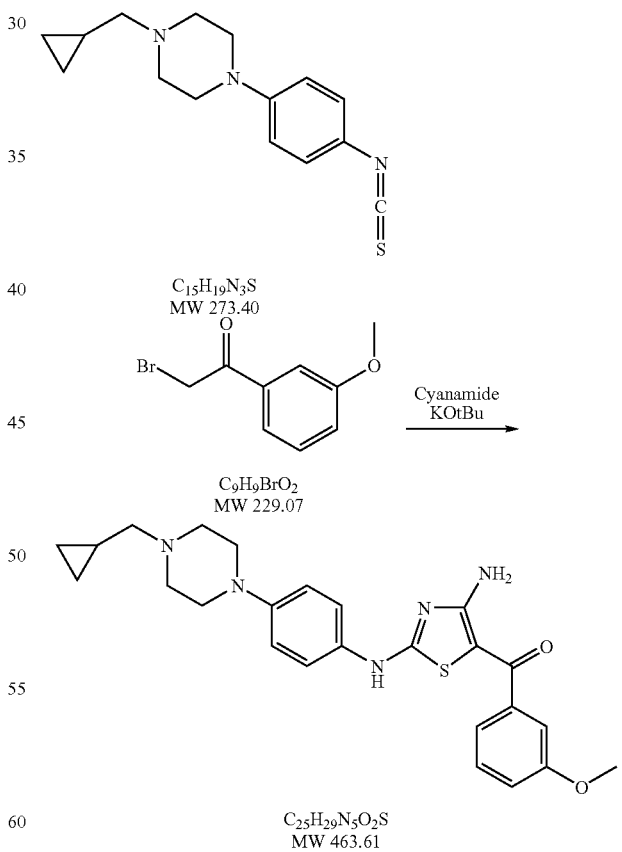

This compound was prepared from cyanamide, 1-(4-isothiocyanato-phenyl)-4-cyclopropylmethylpiperazine (of Example 14G), and 2-bromo-1-(3-methoxyphenyl)ethanone (Aldrich) following-the procedure used in Example 24 Mass spectrum (ES) MH⁺=464.

Example 117

{4-Amino-2-[4-(4-cyclopropylmethyl-piperazin-1-yl)-phenylamino]-thiazol-5-yl}-benzo[1,3]dioxol-5-yl-methanone

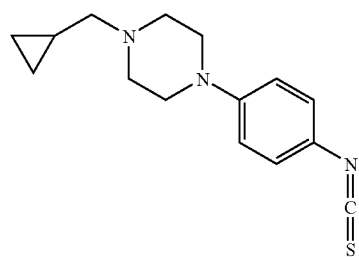

C₁₅H₁₉N₃S
MW 273.40

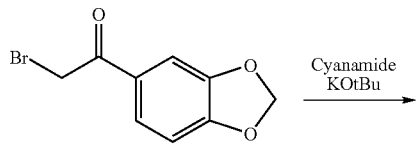

C₉H₇BrO₃
MW 243.06

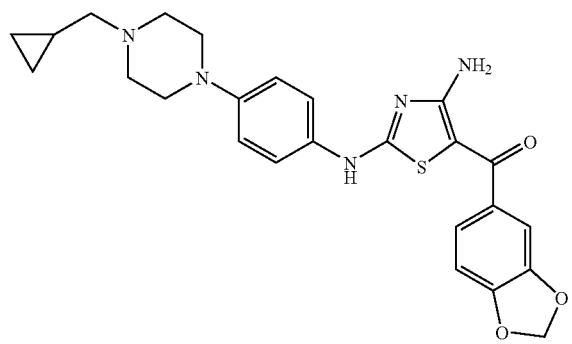

C₂₅H₂₇N₅O₃S
MW 477.59

This compound was prepared from cyanamide, 1-(4-isothiocyanato-phenyl)-4-cyclopropylmethylpiperazine (of Example 14G) and 2-bromo-1-(benzo[1,3]dioxol-5-yl)ethanone (of Example 11) following the procedure used in Example 24 Mass spectrum (ES) MH⁺=478.

Example 118

{4-Amino-2-[4-(4-cyclopropylmethyl-piperazin-1-yl)-phenylamino]-thiazol-5-yl}-(2,3-dihydro-benzo[1,4]dioxin-6-yl)-methanone

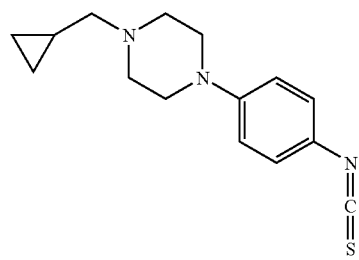

C₁₅H₁₉N₃S
MW 273.40

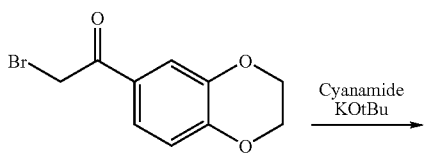

C₁₀H₉BrO₃
MW 257.09

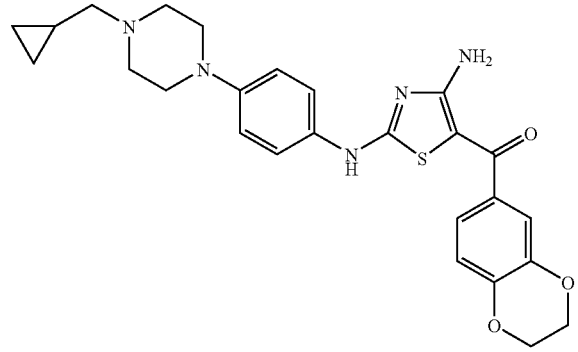

C₂₆H₂₉N₅O₃S
MW 491.62

This compound was prepared from cyanamide, 1-(4-isothiocyanato-phenyl)-4-cyclopropylmethylpiperazine (of Example 14G) and 2-bromo-1-(2,3-dihydro-benzo[1,4]dioxin-6-yl)ethanone (Maybridge Chemical Company Ltd.) following the procedure used in Example 24. Mass spectrum (ES) MH⁺=492.

Example 119

{4-Amino-2-[4-(4-cyclopropylmethyl-piperazin-1-yl)-phenylamino]-thiazol-5-yl}-(3-fluoro-4-hydroxy-phenyl)-methanone

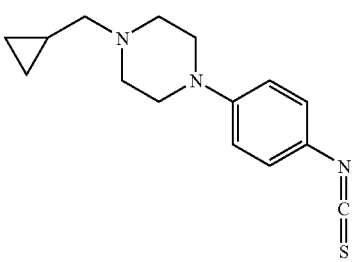

C₁₅H₁₉N₃S
MW 273.40

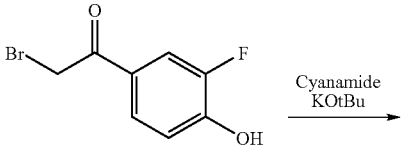

C₈H₆BrFO₂
MW 233.04

-continued

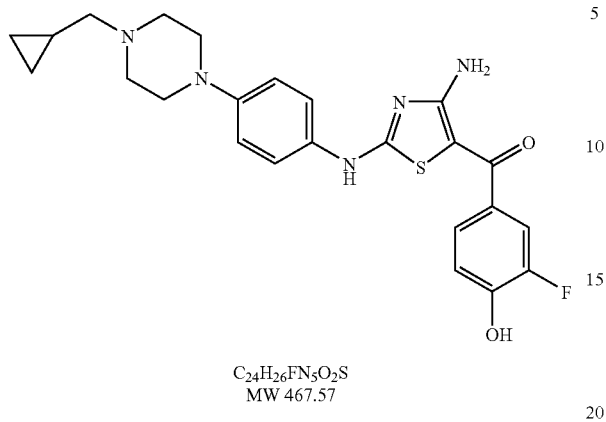

C₂₄H₂₆FN₅O₂S
MW 467.57

This compound was prepared from cyanamide, 1-(4-isothiocyanato-phenyl)-4-cyclopropylmethylpiperazine (of Example 14G) and 2-bromo-1-(3-fluoro-4-hydroxyphenyl)ethanone (of Example 14M) following the procedure used in Example 24. Mass spectrum (ES) MH⁺=468.

Example 120

{4-Amino-2-[4-(4-methyl-piperazin-1-yl)-phenylamino]-thiazol-5-yl}-(3-difluoromethoxy-phenyl)-methanone

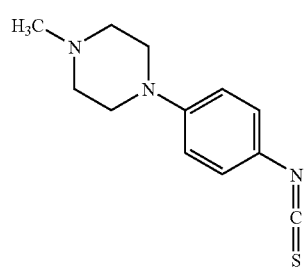

C₁₂H₁₅N₃S
MW 233.34

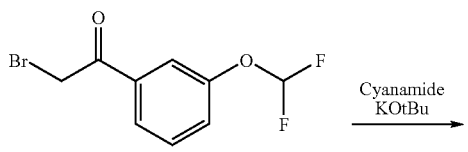

C₉H₇BrF₂O₂
MW 265.06

-continued

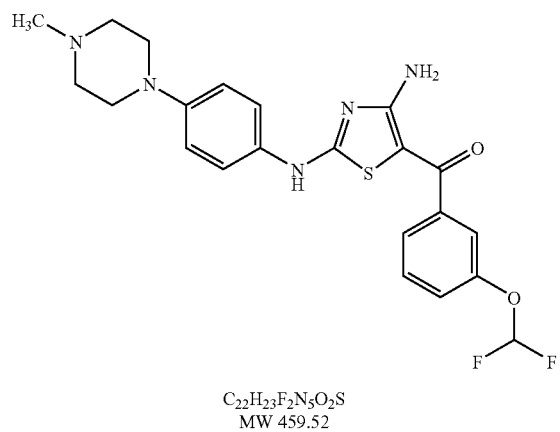

C₂₂H₂₃F₂N₅O₂S
MW 459.52

This compound was prepared from cyanamide, 1-(4-isothiocyanato-phenyl)-4-methylpiperazine (of Example 1, and 2-bromo-1-(3-difluoro-methoxy-phenyl)ethanone (of Example 14L) following the procedure used in Example 24. Mass spectrum (ES) MH⁺=460.

Example 121

{4-Amino-2-[4-(4-cyclopropylmethyl-piperazin-1-yl)-phenylamino]-thiazol-5-yl}-(3-fluoro-phenyl)-methanone

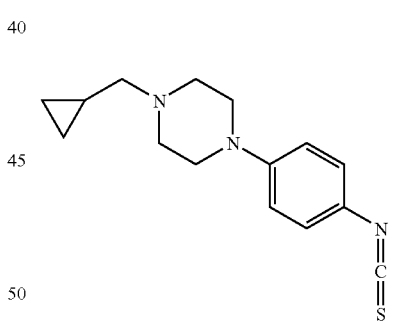

C₁₅H₁₉N₃S
MW 273.40

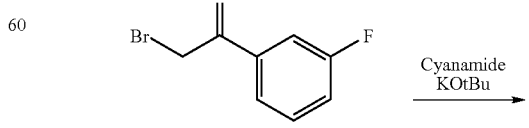

C₈H₆BrFO
MW 217.04

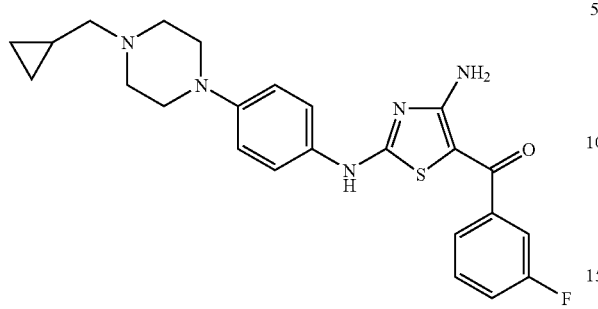

C<sub>24</sub>H<sub>26</sub>FN<sub>5</sub>OS
MW 451.57

This compound was prepared from cyanamide, 1-(4-isothiocyanatphenyl)-4-cyclopropylmethylpiperazine (of Example 14G) and 2-bromo-1-(3-fluoro-phenyl)ethanone (Aldrich) following the procedure used in Example 24 Mass spectrum (ES) MH$^+$=452.

Example 122

{4-Amino-2-[4-(4-cyclopropylmethyl-piperazin-1-yl)-phenylamino]-thiazol-5-yl}-(3-fluoro-4-methoxy-phenyl)-methanone

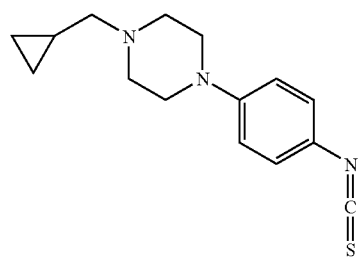

C<sub>15</sub>H<sub>19</sub>N<sub>3</sub>S
MW 273.40

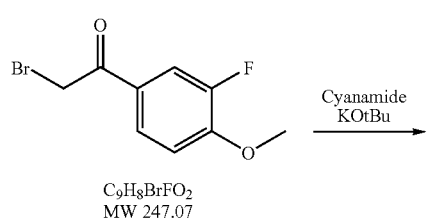

C<sub>9</sub>H<sub>8</sub>BrFO<sub>2</sub>
MW 247.07

Cyanamide
KOtBu
→

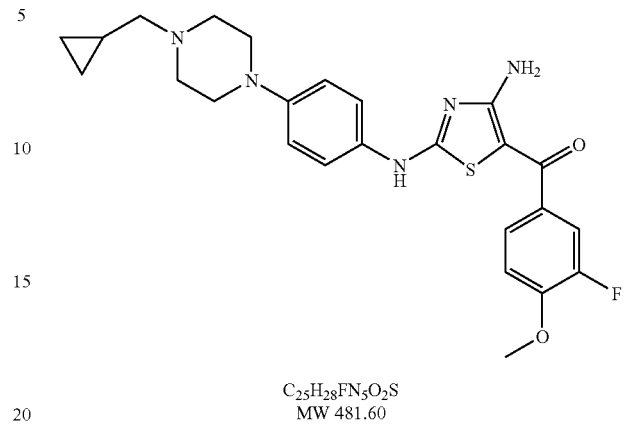

C<sub>25</sub>H<sub>28</sub>FN<sub>5</sub>O<sub>2</sub>S
MW 481.60

This compound was prepared from cyanamide, 1-(4-isothiocyanato-phenyl)-4-cyclopropylmethylpiperazine (of Example 14G) and 2-bromo-1-(3-fluoro-4-methoxyphenyl)ethanone (of Example 13) following the procedure used in Example 24. Mass spectrum (ES) MH$^+$=482.

Example 123

{4-Amino-2-[4-(4-methyl-piperazin-1-yl)-phenylamino]-thiazol-5-yl}-(3-hydroxy-phenyl)-methanone

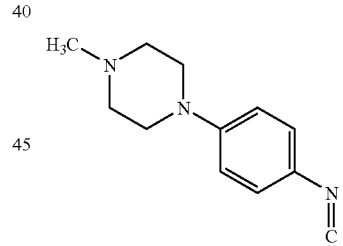

C<sub>12</sub>H<sub>15</sub>N<sub>3</sub>S
MW 233.34

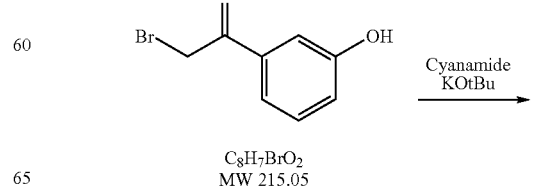

C<sub>8</sub>H<sub>7</sub>BrO<sub>2</sub>
MW 215.05

Cyanamide
KOtBu
→

-continued

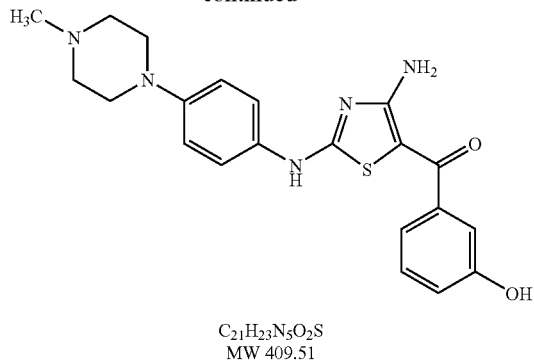

C₂₁H₂₃N₅O₂S
MW 409.51

This compound was prepared from cyanamide, 1-(4-isothiocyanato-phenyl)-4-cyclopropylmethylpiperazine (of Example 1) and 2-bromo-1-(3-hydroxyphenyl)ethanone (of Example 14N) following the procedure used in Example 24. Mass spectrum (ES) MH⁺=410.

Example 124

3-{4-Amino-2-[4-(4-methyl-piperazin-1-yl)-phenylamino]-thiazole-5-carbonyl}-benzonitrile

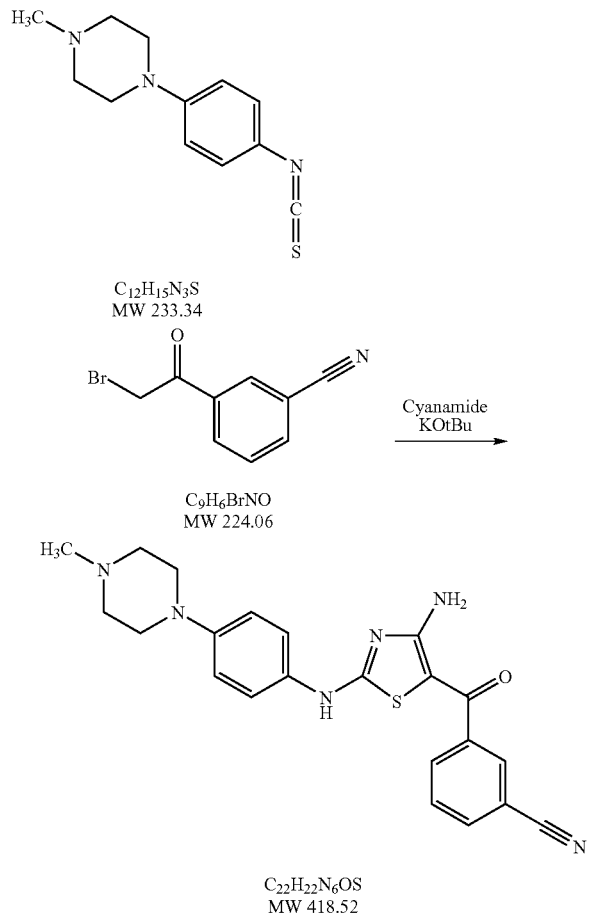

This compound was prepared from cyanamide, 1-(4-isothiocyanato-phenyl)-4-methylpiperazine (of Example 1) and 3-cyanophenacyl bromide (Maybridge Chemical Co. Ltd.) following the procedure used in Example 24. Mass spectrum (ES) MH⁺=419.

Example 125

Antiproliferative Activity

The antiproliferative activity of the compounds of the invention is demonstrated below. These activities indicate that the compounds of the present invention are useful in treating cancer, in particular solid tumors such as breast and colon tumors.

Kinase Assays

To determine inhibition of Cdk4, Cdk2 and Cdk1 activity, kinase assays were conducted using FlashPlate™ assays (NEN™-Life Science Products). FlashPlate assays were performed using recombinant human cyclin B-CDK1, human cyclin E-CDK2 or human cyclin D1-CDK4 complexes. GST-cyclinE (GST-cycE), CDK2, GST-cyclinB (GST-cycB), CDK1, GST-CDK4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. *Cell* 1993, 75, 805–816). A 6×-Histidine tagged truncated form of retinoblastoma (Rb) protein (amino acid 386–928) was used as the substrate for the cycD1-CDK4, cycB-CDK1 and the cycE-CDK2 assays (the expression plasmid was provided by Dr. Veronica Sullivan, Department of Molecular Virology, Roche Research Centre, Welwyn Garden City, United Kingdom). The Rb protein is a natural substrate for phosphorylation by CDK4, CDK2 and CDK1 (see Herwig and Strauss *Eur. J. Biochem. Vol.* 246 (1997) pp. 581–601 and the references cited therein).

The expression of the 62 Kd protein was under the control of an IPTG inducible promoter in an M15 *E. coli* strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For all three kinase assays reported herein, 96-well Flash-Plates were coated with Rb protein at 10 μg/ml, using 100 μl per well. Plates were incubated at 4° C. overnight or at room temperature for 3 hours on a shaker. To control for nonspecific phosphorylation, one row of wells was coated with 100 μl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 μl reaction mix (25 mM HEPES, 20 mM MgCl₂, 0.002% Tween 20, 2 mM DTT, 1 μM ATP, 4 nM ³³P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times \frac{1 - \text{test compound} - \text{nonspecific}}{\text{total} - \text{nonspecific}}$$

where "test compound" refers to the average counts per minute of the test duplicates, "nonspecific" refers to the average counts per minute when no CyclinD/Cdk4, etc., was added, and "total" refers to the average counts per minute when no compound was added. The $IC_{50}$ value is the concentration of test compound that reduces by 50% the protein-kinase induced incorporation of the radiolabel under the test conditions described.

The results of the foregoing in vitro experiments are set forth in Table 1 below.

The $IC_{50}$ values are summarized in the Table 1 below.

Cell Based Assays (Tetrazolium Dye Proliferation Assay)

Proliferation was evaluated by the tetrazolium dye assay according to the procedure of Denizot and Lang (Denizot, F. and Lang, R. *J Immunol Methods* 1986, 89, 271–277). The cell line used was HCT116, a colorectal carcinoma cell line obtained from the American Type Cell Culture Collection (ATCC; Rockville, Md.). The cells were grown in McCoy's 5A medium supplemented with 10% FCS and L-glutamine.

Cells were plated at the appropriate seeding density to give logarithmic growth over the course of the assay in a 96-well tissue culture plate. Plates were incubated overnight at 37° C. in a humidified incubator with 5% $CO_2$. The next day, test compounds were serially diluted to four times the final concentration in the appropriate medium containing 1.2% DMSO. One-fourth final volume of each dilution was added in duplicate to the plates containing cells. The same volume of 1.2% DMSO in medium was added to a row of "control wells" such that the final concentration of DMSO in each well was 0.3%. Wells to which no cells were added served as the "blank." Wells to which no inhibitor was added served as "no inhibitor control." The plates were) returned to the incubator, and at set time points (determined by their growth curves) plates were analyzed as described below.

3-(4,5-dimethylthiazole-2-yl)-2,5-diphenyl-2H-tetrazolium bromide (thiazolyl blue; MTT; Sigma) was added to each well to yield a final concentration of 1 mg/ml. Plates were returned to the incubator for 2.5–3 hours at 37° C. The MTT-containing medium was removed and the resulting formazan metabolite was solubilized in 100% ethanol with shaking for 15 minutes at room temperature. Absorbance readings were taken in a microtiter plate reader (Dynatech and Molecular Devices plate readers were used interchangeably) at a wavelength of 570 nm with a 650 nm reference. Percent inhibition (% INH) is calculated by subtracting the absorbance of the blank well from all wells, then subtracting the ratio of the average absorbance of each test duplicate ($S_{AVE}$) by the average of the controls ($C_{AVE}$) from 1.00. The final number is then multiplied by 100 (% INH=(1.00−$S_{AVE}$/$C_{AVE}$)×100). The concentration at which 50% inhibition of cell proliferation is obtained (the $IC_{50}$) is determined from the linear regression of a plot of the logarithm of the concentration versus percent inhibition. The $IC_{50}$ values are also shown in Table 1 below.

TABLE 1

This table shows the $IC_{50}$s of compounds of the instant Examples in CDK4, CDK2, and CDK1 kinase assays, and also the $IC_{50}$s in the cell-based assays ("MTT") assay.

| Example Number | CDK4 $IC_{50}(\mu M)$ | CDK2 $IC_{50}(\mu M)$ | CDK1 $IC_{50}(\mu M)$ | MTT $IC_{50}(\mu M)$ |
|---|---|---|---|---|
| Example 24 | 0.02 | 4.3 | 2.5 | 3.9 |
| Example 25 | 0.018 | 3.5 | 0.5 | 3.5 |
| Example 26 | 0.059 | 6.2 | 9 | 5.6 |
| Example 27 | 0.004 | 9.4 | 20.1 | 9.1 |
| Example 28 | 0.017 | 22.2 | 9.2 | 9.5 |
| Example 29 | 0.103 | 9.6 | 15.9 | 9.5 |
| Example 30 | 0.053 | 2.3 | 2.4 | 3.6 |
| Example 31 | 0.026 | 2.3 | 0.5 | 4.1 |
| Example 32 | 0.08 | 9.6 | 3.9 | 5.6 |
| Example 33 | 0.008 | 6.5 | 6.1 | 9.2 |
| Example 34 | 0.049 | 6.1 | 11.7 | 3.8 |
| Example 35 | 0.008 | 1.8 | 1.1 | 1.8 |
| Example 36 | 0.025 | 5.4 | 2.1 | 2.8 |
| Example 37 | 0.073 | 6.3 | 10 | 6.6 |
| Example 38 | 0.006 | 2.6 | 2.0 | 1.9 |
| Example 39 | 0.021 | 7.9 | 2.8 | 3.6 |
| Example 40 | 0.014 | 3.1 | 1.3 | 3.0 |
| Example 41 | 0.015 | 3.7 | 2.9 | 3.0 |
| Example 42 | 0.01 | 2.9 | 1.9 | 1.5 |
| Example 43 | 0.021 | 3.4 | 1.9 | 1.3 |
| Example 44 | 0.028 | 11.9 | 1.8 | 3.8 |
| Example 45 | 0.025 | 4.9 | 5.6 | 2.9 |
| Example 46 | 0.014 | 5.2 | 3.6 | 3.6 |
| Example 47 | 0.043 | 0.9 | 0.5 | 2.8 |
| Example 48 | 0.01 | 7.1 | 2.3 | 13.3 |
| Example 49 | 0.015 | 1.5 | 2.1 | 5.3 |
| Example 50 | 0.03 | 2.5 | 5.5 | 9.3 |
| Example 51 | 0.02 | 0.5 | 0.9 | 0.9 |
| Example 52 | 0.028 | 0.7 | 1.2 | 2.3 |
| Example 53 | 0.006 | 1.3 | 2.3 | 2.5 |
| Example 54 | 0.013 | 0.2 | 0.3 | 0.7 |
| Example 55 | 0.05 | 3.2 | 4.3 | 3.8 |
| Example 56 | 0.014 | 0.8 | 1.0 | 0.8 |
| Example 57 | 0.009 | 1.9 | 0.9 | 2.1 |
| Example 58 | 0.019 | 2.4 | 3.9 | 3.1 |

TABLE 1-continued

This table shows the IC$_{50}$s of compounds of the instant Examples in CDK4, CDK2, and CDK1 kinase assays, and also the IC$_{50}$s in the cell-based assays ("MTT") assay.

| Example Number | CDK4 IC$_{50}$(μM) | CDK2 IC$_{50}$(μM) | CDK1 IC$_{50}$(μM) | MTT IC$_{50}$(μM) |
|---|---|---|---|---|
| Example 59 | 0.024 | 4.4 | 4.3 | 3.9 |
| Example 60 | 0.017 | 7.9 | 5.9 | 4.9 |
| Example 61 | 0.012 | 2.3 | 3.5 | 3.9 |
| Example 62 | 0.044 | 5.9 | 10 | 4.4 |
| Example 63 | 0.025 | 5.3 | 5.2 | 1.3 |
| Example 64 | 0.009 | 4.8 | 3.5 | 8.0 |
| Example 65 | 0.026 | 7.4 | 2.2 | 1.2 |
| Example 66 | 0.02 | 3.8 | 9.6 | 10.8 |

Example 126

Tablet Formulation

| Item | Ingredients | Mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 127

Capsule Formulation

| Item | Ingredients | mg/Capsule | | | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Compound A represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 128

Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 129

Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. The compound 1-(4-isothiocyanatophenyl)-4-(1-methylethyl) piperazine.

2. The compound 4-(2-hydroxyethyl)-1-(4-isothiocyanatophenyl) piperazine.

3. A compound selected from the group consisting of:
1-(2-Fluoro-4-isothiocyanatophenyl)-4-methylpiperazine,
1-(1-Methylethyl)-4-(4-nitrophenylpiperazine), 4-[4-(1-Methylethyl)-1-piperazinyl]benzenamine,
1-(4-Isothiocyanatophenyl)-4-(1-methylethyl)piperazine,
4-(2-Hydroxyethyl)-1-(4-isothiocyanatophenyl)piperazine,
1-(4-Isothiocyanatophenyl)-4-(2-methoxy-ethyl)piperazine,
1-(4-Isothiocyanatophenyl)-4-(1-methylpropyl)piperazine,
4-Cyclopentyl-1-(4-isothiocyanatophenyl)piperazine,
1-(4-Isothiocyanatophenyl)-4-(2-methylpropyl)piperazine, and
4-(3-Hydroxypropyl)-1-(4-isothiocyanatophenyl)piperazine.

\* \* \* \* \*